US005866784A

United States Patent [19]
Van Mellaert et al.

[11] Patent Number: 5,866,784
[45] Date of Patent: Feb. 2, 1999

[54] RECOMBINANT PLANT EXPRESSING NON-COMPETITIVELY BINDING INSECTICIDAL CRYSTAL PROTEINS

[75] Inventors: Herman Van Mellaert, Leuvain; Johan Botterman, Zevergem-De Pinte; Jeroen Van Rie, Eeklo; Henk Joos, Aalter, all of Belgium

[73] Assignee: Plant Genetic Systems N.V., Brussels, Belgium

[21] Appl. No.: 465,609

[22] Filed: Jun. 5, 1995

Related U.S. Application Data

[63] Continuation of Ser. No. 173,274, Dec. 23, 1993, abandoned, which is a continuation of Ser. No. 640,400, Jan. 22, 1991, abandoned.

[30] Foreign Application Priority Data

May 31, 1989 [GB] United Kingdom ................. 89401499

[51] Int. Cl.$^6$ ............................... A01H 5/00; A01H 5/10; C12N 15/32; C12N 15/82
[52] U.S. Cl. .................. 800/205; 435/172.3; 435/320.1; 435/419; 435/430; 536/23.71; 800/250; 800/DIG. 13; 800/DIG. 15; 800/DIG. 27; 800/DIG. 42; 800/DIG. 43; 800/DIG. 44; 800/DIG. 63
[58] Field of Search ..................................... 800/205, 250, 800/DIG. 13, DIG. 15, DIG. 27, DIG. 42, DIG. 43, DIG. 44, DIG. 63; 435/240.4, 320.1, 172.3, 419, 430; 536/23.71

[56] References Cited

U.S. PATENT DOCUMENTS 5,500,365  3/1996  Fischhoff et al. .................... 435/240.4

FOREIGN PATENT DOCUMENTS

| A 0192319 | 8/1986 | European Pat. Off. . |
|---|---|---|
| A 0193259 | 9/1986 | European Pat. Off. . |
| A 0221024 | 5/1987 | European Pat. Off. . |
| A 0228838 | 7/1987 | European Pat. Off. . |
| 305275 | 3/1989 | European Pat. Off. . |
| WO-A 88/088880 | 11/1988 | WIPO . |

OTHER PUBLICATIONS

"Binding of Different Types of *Bacillus Thuringiensis* Delta–Endotoxins to Midgut Brush Border Membrane Vesicles is Correlated with the Insecticidal Spectrum", Van Mellaert et al., XXI Annual Meeting of the Society for Inveertebrate Pathology at the University of California, San Diego at La Jolla on Aug. 14–18, 1988.

A. Devonshire et al., A Carboxylesterase with Broad Substrate Specificity Causes Organophosphorus, Carbamate and Pyrethroid Resistance in Peach—Potato Aphids (*Myzus persicae*) *Pesticide Biochemistry and Physiology* (1982) 18:235–246.

C. Hofmann et al., "Specificity of *Bacillus thuringiensis* δ–endotoxins is Correlated With the Presence of High–Affinity Binding Sites in the Brush Border Membrance of Target Insect Midguts", Proc. Natl. Acad. Sci. USA (1988) 85:7844–7848.

"Current Uses and Future Prospects for Microbial Pest Control Agents", *Med. Fac. Landbouww. Rijksuniv.*, Gent, 52(2a), 1987, pp. 113–123, C. Payne.

"The binding of *Bacillus thuringiensis* delta–endotoxin to cultured insect cells and to brush border membrane vesicles", Diss. ETH No. 8498, Christina Hofmann.

"Evolution of Resistance in the Presence of Two Insecticides", *The Genetics Society of America*, G. Mani, Nov. 1984, pp. 761–783.

"Cloning and Nucleotide Sequence of the Gene Coding for a 135–KDAL Protein of *Bacillus Thuringiensis Aizawai*", J. Wong, et al. p. 27.

Van Mellaert, et al. ibid.

"Simultaneous expresson of two kinds of insecticidal proteins", *Patent Abstracts of Japan*, vol. 13, No. 326, (1989), C–620.

"A translation fusion product of two different insecticidal crystal protein genes of *Bacillus thuringiensis* exhibits an enlarged insecticidal spectrum", *Cheimical Abstracts*, vol. 112, No. 21, (1990), p. 262, 193742F.

"Binding of the delta endotoxin from *Bacillus thuringiensis* to brush border membrane vesicles of the cabbage butterfly (*Pieris brassiae*)", *Eur. J. Biochem.*, vol. 173, (1988), pp. 85–91.

"Specificity of *Bacillus thuringiensis* delta–endotoxins is correlated with the presence of high–affinity binding sites in the brush border membrane of target insect midgut", *Proc. Natl. Acad. Sci.* vol. 85, (1988), pp. 7844–7848.

Chimera insecticidal protein of *Bacillus thuringiensis*, *Patent Abstracts of Japan*, vol. 12, No. 391, (1988), (C–537).

Aronson et al., *Microbiol. Reviews*, Mar. 1986, vol. 50, No. 1, pp. 1–24.

Hofmann (1988) Ph.D. Thesis Swiss Federal Inst. of Technology, Zurich, Diss ETH No. 8498.

Mani (1985) Genetics 109: 761–783.

Voeck et al. (1987) Nature 328: 33–37.

*Primary Examiner*—Douglas W. Robinson
*Assistant Examiner*—Amy J. Nelson
*Attorney, Agent, or Firm*—Burns, Doane, Swecker & Mathis, L.L.P.

[57] ABSTRACT

Plants made resistant to insects by transforming their nuclear genome with two or more DNA sequences, each encoding a different non-competitively binding *B. thuringiensis* protoxin or insecticidal part thereof, preferably the toxin thereof.

17 Claims, 55 Drawing Sheets

% Max. Binding of $^{125}$I-Bt3-Toxin vs. [Competitor] (nM)

% Max. Binding of $^{125}$I-Bt2-Toxin vs. [Competitor] (nM)

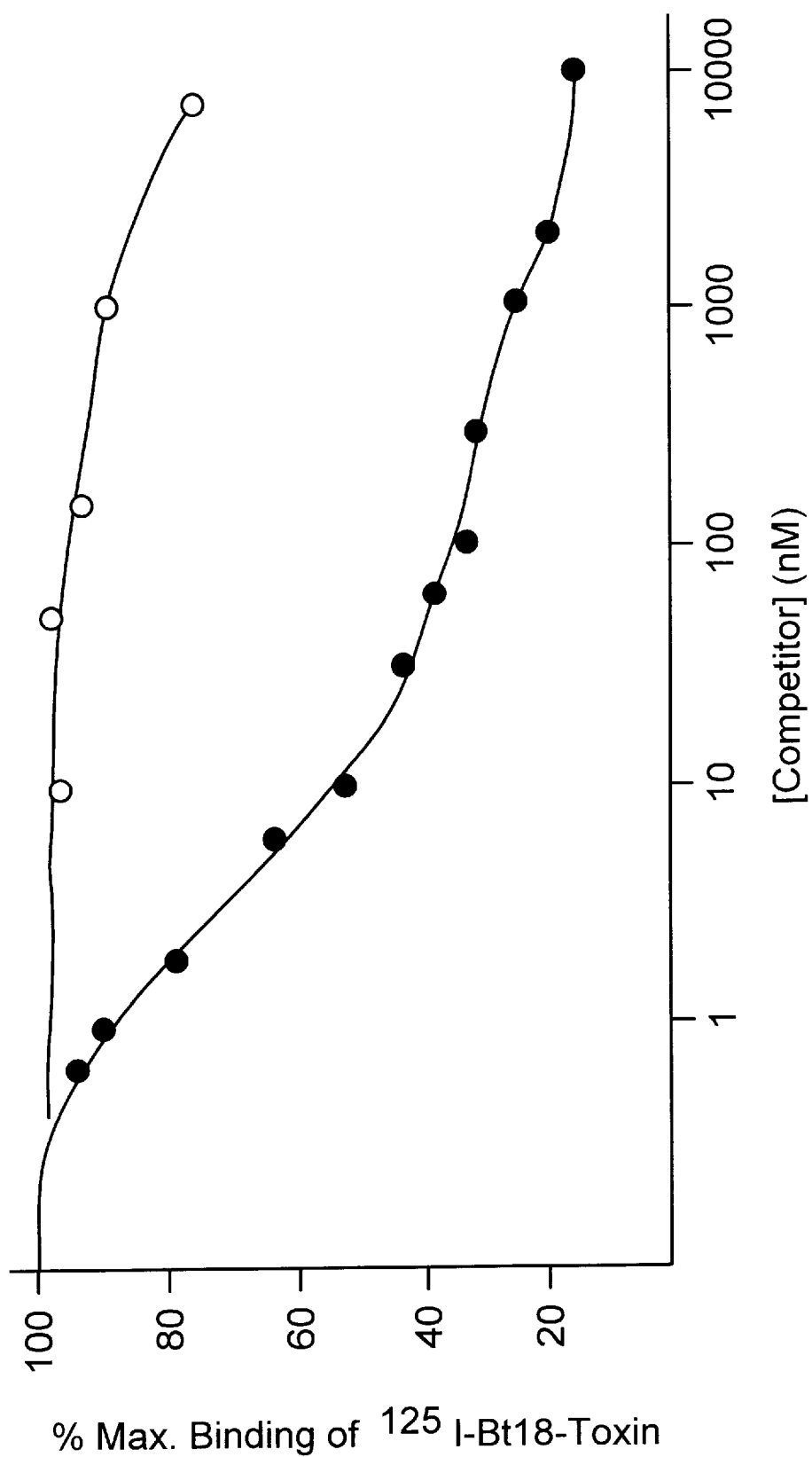

FIG. 13A

```
           10         20         30         40         50
GGATCTGTTT TAATATAAGG GATTTGTGCC CTTCTCGTTA TATTCTTTTA 60         70         80         90        100
TTAGCCCCAA AAACTAGTGC AACTAAATAT TTTTATAATT ACACTGATTA 110        120        130        140        150
AATACTTTAT TTTTGGGAGT AAGATTTATG CTGAAATGTA ATAAAATTCG 160        170        180        190        200
TTCCATTTTC TGTATTTTCT CATAAAATGT TTCATATGCT TTAAATTGTA 210        220        230        240        250
GTAAAGAAAA ACAGTACAAA CTTAAAAGGA CTTTAGTAAT TTAATAAAAA 260        269        278        287
AAGGGGATAG TTT ATG GAA ATA AAT AAT CAA AAC CAA TGT
            MET Glu Ile Asn Asn Gln Asn Gln Cys
```

FIG. 13B

```
         296                 305                 314                 323
     GTG CCT TAC AAT TGT TTA AGT AAT CCT AAG GAG ATA ATA
     Val Pro Tyr Asn Cys Leu Ser Asn Pro Lys Glu Ile Ile 332                 341                 350                 359             368
     TTA GGC GAG GAA AGG CTA GAA ACA GGG AAT ACT GTA GCA
     Leu Gly Glu Glu Arg Leu Glu Thr Gly Asn Thr Val Ala 377                 386                 395                 404
     GAC ATT TCA TTA GGG CTT ATT AAT TTT CTA TAT TCT AAT
     Asp Ile Ser Leu Gly Leu Ile Asn Phe Leu Tyr Ser Asn 413                 422                 431                 440
     TTT GTA CCA GGA GGA GGA TTT ATA GTA GGT TTA CTA GAA
     Phe Val Pro Gly Gly Gly Phe Ile Val Gly Leu Leu Glu 449                 458                 467                 476             485
     TTA ATA TGG GGA TTT ATA GGG CCT TCG CAA TGG GAT ATT
     Leu Ile Trp Gly Phe Ile Gly Pro Ser Gln Trp Asp Ile 494                 503                 512                 521
     TTT TTA GCT CAA ATT GAG CAA TTG ATT AGT CAA AGA ATA
     Phe Leu Ala Gln Ile Glu Gln Leu Ile Ser Gln Arg Ile
```

FIG. 13C

```
        530              539              548              557
GAA GAA TTT GCT AGG AAT CAG GCA ATT TCA AGA TTG GAG
Glu Glu Phe Ala Arg Asn Gln Ala Ile Ser Arg Leu Glu 566              575              584              593              602
GGG CTA AGC AAT CTT TAT AAG GTC TAT GTT AGA GCG TTT
Gly Leu Ser Asn Leu Tyr Lys Val Tyr Val Arg Ala Phe 611              620              629              638
AGC GAC TGG GAG AAA GAT CCT ACT AAT CCT GCT TTA AGG
Ser Asp Trp Glu Lys Asp Pro Thr Asn Pro Ala Leu Arg 647              656              665              674
GAA GAA ATG CGT ATA CAA TTT AAT GAC ATG AAT AGT GCT
Glu Glu MET Arg Ile Gln Phe Asn Asp MET Asn Ser Ala 683              692              701              710              719
CTC ATA ACG GCT ATT CCA CTT TTT AGA GTT CAA AAT TAT
Leu Ile Thr Ala Ile Pro Leu Phe Arg Val Gln Asn Tyr 728              737              746              755
GAA GTT GCT CTT TTA TCT GTA TAT GTT CAA GCC GCA AAC
Glu Val Ala Leu Leu Ser Val Tyr Val Gln Ala Ala Asn
```

FIG. 13D

```
      764              773              782              791
TTA  CAT  TTA  TCT  ATT  TTA  AGG  GAT  GTT  TCA  GTT  TTC  GGA
Leu  His  Leu  Ser  Ile  Leu  Arg  Asp  Val  Ser  Val  Phe  Gly 800              809              818              827              836
GAA  AGA  TGG  GGA  TAT  GAT  ACA  GCG  ACT  ATC  AAT  AAT  CGC
Glu  Arg  Trp  Gly  Tyr  Asp  Thr  Ala  Thr  Ile  Asn  Asn  Arg 845              854              863              872
TAT  AGT  GAT  CTG  ACT  AGC  CTT  ATT  CAT  GTT  TAT  ACT  AAC
Tyr  Ser  Asp  Leu  Thr  Ser  Leu  Ile  His  Val  Tyr  Thr  Asn 881              890              899              908
CAT  TGT  GTG  GAT  ACG  TAT  AAT  CAG  GGA  TTA  AGG  CGT  TTG
His  Cys  Val  Asp  Thr  Tyr  Asn  Gln  Gly  Leu  Arg  Arg  Leu 917              926              935              944              953
GAA  GGT  CGT  TTT  CTT  AGC  GAT  TGG  ATT  GTA  TAT  AAT  CGT
Glu  Gly  Arg  Phe  Leu  Ser  Asp  Trp  Ile  Val  Tyr  Asn  Arg 962              971              980              989
TTC  CGG  AGA  CAA  TTG  ACA  ATT  TCA  GTA  TTA  GAT  ATT  GTT
Phe  Arg  Arg  Gln  Leu  Thr  Ile  Ser  Val  Leu  Asp  Ile  Val
```

FIG. 13E

```
      998           1007          1016          1025
GCG TTT TTT CCA AAT TAT GAT ATT AGA ACA TAT CCA ATT
Ala Phe Phe Pro Asn Tyr Asp Ile Arg Thr Tyr Pro Ile 1034          1043          1052          1061          1070
CAA ACA GCT ACT CAG CTA ACG AGG GAA GTC TAT CTG GAT
Gln Thr Ala Thr Gln Leu Thr Arg Glu Val Tyr Leu Asp 1079          1088          1097          1106
TTA CCT TTT ATT AAT CAA AAT CTT TCT CCT GCA GCA AGC
Leu Pro Phe Ile Asn Gln Asn Leu Ser Pro Ala Ala Ser 1115          1124          1133          1142
TAT CCA ACC TTT TCA GCT GCT GAA AGT GCT ATA ATT AGA
Tyr Pro Thr Phe Ser Ala Ala Glu Ser Ala Ile Ile Arg 1151          1160          1169          1178          1187
AGT CCT CAT TTA GTA GAC TTT TTA AAT AGC TTT ACC ATT
Ser Pro His Leu Val Asp Phe Leu Asn Ser Phe Thr Ile 1196          1205          1214          1223
TAT ACA GAT AGT CTG GCA CGT TAT GCA TAT TGG GGA GGG
Tyr Thr Asp Ser Leu Ala Arg Tyr Ala Tyr Trp Gly Gly
```

FIG. 13F

|  | 1232 |  |  | 1241 |  |  | 1250 |  |  | 1259 |  |
|---|---|---|---|---|---|---|---|---|---|---|---|
| CAC | TTG | GTA | AAT | TCT | TTC | CGC | ACA | GGA | ACC | ACT | ACT | AAT |
| His | Leu | Val | Asn | Ser | Phe | Arg | Thr | Gly | Thr | Thr | Thr | Asn |

| 1268 |  |  | 1277 |  |  | 1286 |  |  | 1295 |  |  | 1304 |
|---|---|---|---|---|---|---|---|---|---|---|---|---|
| TTG | ATA | AGA | TCC | CCT | TTA | TAT | GGA | AGG | GAA | GGA | AAT | ACA |
| Leu | Ile | Arg | Ser | Pro | Leu | Tyr | Gly | Arg | Glu | Gly | Asn | Thr |

|  |  | 1313 |  |  | 1322 |  |  | 1331 |  |  | 1340 |  |
|---|---|---|---|---|---|---|---|---|---|---|---|---|
| GAG | CGC | CCC | GTA | ACT | ATT | ACC | GCA | TCA | CCT | AGC | GTA | CCA |
| Glu | Arg | Pro | Val | Thr | Ile | Thr | Ala | Ser | Pro | Ser | Val | Pro |

|  | 1349 |  |  | 1358 |  |  | 1367 |  |  | 1376 |  |  |
|---|---|---|---|---|---|---|---|---|---|---|---|---|
| ATA | TTT | AGA | ACA | CTT | TCA | TAT | ATT | ACA | GGC | CTT | GAC | AAT |
| Ile | Phe | Arg | Thr | Leu | Ser | Tyr | Ile | Thr | Gly | Leu | Asp | Asn |

| 1385 |  |  | 1394 |  |  | 1403 |  |  | 1412 |  |  | 1421 |
|---|---|---|---|---|---|---|---|---|---|---|---|---|
| TCA | AAT | CCT | GTA | GCT | GGA | ATC | GAG | GGA | GTG | GAA | TTC | CAA |
| Ser | Asn | Pro | Val | Ala | Gly | Ile | Glu | Gly | Val | Glu | Phe | Gln |

|  |  | 1430 |  |  | 1439 |  |  | 1448 |  |  | 1457 |  |
|---|---|---|---|---|---|---|---|---|---|---|---|---|
| AAT | ACT | ATA | AGT | AGA | AGT | ATC | TAT | CGT | AAA | AGC | GGT | CCA |
| Asn | Thr | Ile | Ser | Arg | Ser | Ile | Tyr | Arg | Lys | Ser | Gly | Pro |

FIG. 13G

```
     1466            1475            1484            1493
ATA GAT TCT TTT AGT GAA TTA CCA CCT CAA GAT GCC AGC
Ile Asp Ser Phe Ser Glu Leu Pro Pro Gln Asp Ala Ser 1502            1511            1520            1529            1538
GTA TCT CCT GCA ATT GGG TAT AGT CAC CGT TTA TGC CAT
Val Ser Pro Ala Ile Gly Tyr Ser His Arg Leu Cys His 1547            1556            1565            1574
GCA ACA TTT TTA GAA CGG ATT AGT GGA CCA AGA ATA GCA
Ala Thr Phe Leu Glu Arg Ile Ser Gly Pro Arg Ile Ala 1583            1592            1601            1610
GGC ACC GTA TTT TCT TGG ACA CAC CGT AGT GCC AGC CCT
Gly Thr Val Phe Ser Trp Thr His Arg Ser Ala Ser Pro 1619            1628            1637            1646            1655
ACT AAT GAA GTA AGT CCA TCT AGA ATT ACA CAA ATT CCA
Thr Asn Glu Val Ser Pro Ser Arg Ile Thr Gln Ile Pro 1664            1673            1682            1691
TGG GTA AAG GCG CAT ACT CTT GCA TCT GGT GCC TCC GTC
Trp Val Lys Ala His Thr Leu Ala Ser Gly Ala Ser Val
```

FIG. 13H

```
     1700            1709            1718            1727
ATT AAA GGT CCT GGA TTT ACA GGT GGA GAT ATT CTG ACT
Ile Lys Gly Pro Gly Phe Thr Gly Gly Asp Ile Leu Thr 1736            1745            1754            1763            1772
AGG AAT AGT ATG GGC GAG CTG GGG ACC TTA CGA GTA ACC
Arg Asn Ser MET Gly Glu Leu Gly Thr Leu Arg Val Thr 1781            1790            1799            1808
TTC ACA GGA AGA TTA CCA CAA AGT TAT TAT ATA CGT TTC
Phe Thr Gly Arg Leu Pro Gln Ser Tyr Tyr Ile Arg Phe 1817            1826            1835            1844
CGT TAT GCT TCG GTA GCA AAT AGG AGT GGT ACA TTT AGA
Arg Tyr Ala Ser Val Ala Asn Arg Ser Gly Thr Phe Arg 1853            1862            1871            1880            1889
TAT TCA CAG CCA CCT TCG TAT GGA ATT TCA TTT CCA AAA
Tyr Ser Gln Pro Pro Ser Tyr Gly Ile Ser Phe Pro Lys 1898            1907            1916            1925
ACT ATG GAC GCA GGT GAA CCA CTA ACA TCT CGT TCG TTC
Thr MET Asp Ala Gly Glu Pro Leu Thr Ser Arg Ser Phe
```

FIG. 13I

```
     1934         1943         1952         1961
GCT CAT ACA ACA CTC TTC ACT CCA ATA ACC TTT TCA CGA
Ala His Thr Thr Leu Phe Thr Pro Ile Thr Phe Ser Arg 1970         1979         1988         1997         2006
GCT CAA GAA GAA TTT GAT CTA TAC ATC CAA TCG GGT GTT
Ala Gln Glu Glu Phe Asp Leu Tyr Ile Gln Ser Gly Val
                                                 ---
            2015         2024         2033         2042
TAT ATA GAT CGA ATT GAA TTT ATA CCG GTT ACT GCA ACA
Tyr Ile Asp Arg Ile Glu Phe Ile Pro Val Thr Ala Thr
------------------------------------------------------->
     2051         2060         2069         2078
TTT GAG GCA GAA TAT GAT TTA GAA AGA GCG CAA AAG GTG
Phe Glu Ala Glu Tyr Asp Leu Glu Arg Ala Gln Lys Val 2087         2096         2105         2114         2123
GTG AAT GCC CTG TTT ACG TCT ACA AAC CAA CTA GGG CTA
Val Asn Ala Leu Phe Thr Ser Thr Asn Gln Leu Gly Leu 2132         2141         2150         2159
AAA ACA GAT GTG ACG GAT TAT CAT ATT GAT CAG GTA TCC
Lys Thr Asp Val Thr Asp Tyr His Ile Asp Gln Val Ser
```

FIG. 13J

```
      2168            2177            2186            2195
AAT  CTA  GTT  GCG  TGT  TTA  TCG  GAT  GAA  TTT  TGT  CTG  GAT
Asn  Leu  Val  Ala  Cys  Leu  Ser  Asp  Glu  Phe  Cys  Leu  Asp 2204            2213            2222            2231            2240
GAA  AAG  AGA  GAA  TTG  TCC  GAG  AAA  GTT  AAA  CAT  GCA  AAG
Glu  Lys  Arg  Glu  Leu  Ser  Glu  Lys  Val  Lys  His  Ala  Lys 2249            2258            2267            2276
CGA  CTC  AGT  GAT  GAG  CGG  AAT  TTA  CTT  CAA  GAT  CCA  AAC
Arg  Leu  Ser  Asp  Glu  Arg  Asn  Leu  Leu  Gln  Asp  Pro  Asn 2285            2294            2303            2312
TTC  AGA  GGG  ATC  AAT  AGG  CAA  CCA  GAC  CGT  GGC  TGG  AGA
Phe  Arg  Gly  Ile  Asn  Arg  Gln  Pro  Asp  Arg  Gly  Trp  Arg 2321            2330            2339            2348            2357
GGA  AGT  ACG  GAT  ATT  ACT  ATC  CAA  GGA  GGA  GAT  GAC  GTA
Gly  Ser  Thr  Asp  Ile  Thr  Ile  Gln  Gly  Gly  Asp  Asp  Val 2366            2375            2384            2393
TTC  AAA  GAG  AAT  TAC  GTT  ACG  CTA  CCG  GGT  ACC  TTT  GAT
Phe  Lys  Glu  Asn  Tyr  Val  Thr  Leu  Pro  Gly  Thr  Phe  Asp
```

FIG. 13K

|  | 2402 |  |  | 2411 |  |  | 2420 |  |  | 2429 |  |
|---|---|---|---|---|---|---|---|---|---|---|---|
| GAG | TGC | TAT | CCA | ACG | TAT | TTA | TAT | CAA | AAA | ATA | GAT | GAG |
| Glu | Cys | Tyr | Pro | Thr | Tyr | Leu | Tyr | Gln | Lys | Ile | Asp | Glu |

| 2438 |  |  | 2447 |  |  | 2456 |  |  | 2465 |  |  | 2474 |
|---|---|---|---|---|---|---|---|---|---|---|---|---|
| TCG | AAA | TTA | AAA | GCC | TAT | ACC | CGT | TAT | CAA | TTA | AGA | GGG |
| Ser | Lys | Leu | Lys | Ala | Tyr | Thr | Arg | Tyr | Gln | Leu | Arg | Gly |

|  | 2483 |  |  | 2492 |  |  | 2501 |  |  | 2510 |  |
|---|---|---|---|---|---|---|---|---|---|---|---|
| TAT | ATC | GAA | GAT | AGT | CAA | GAC | TTA | GAA | ATC | TAT | TTA | ATT |
| Tyr | Ile | Glu | Asp | Ser | Gln | Asp | Leu | Glu | Ile | Tyr | Leu | Ile |

|  | 2519 |  |  | 2528 |  |  | 2537 |  |  | 2546 |  |
|---|---|---|---|---|---|---|---|---|---|---|---|
| CGT | TAC | AAT | GCA | AAA | CAC | GAA | ATA | GTA | AAT | GTA | CCA | GGT |
| Arg | Tyr | Asn | Ala | Lys | His | Glu | Ile | Val | Asn | Val | Pro | Gly |

| 2555 |  |  | 2564 |  |  | 2573 |  |  | 2582 |  |  | 2591 |
|---|---|---|---|---|---|---|---|---|---|---|---|---|
| ACA | GGA | AGT | TTA | TGG | CCT | CTT | TCT | GTA | GAA | AAT | CAA | ATT |
| Thr | Gly | Ser | Leu | Trp | Pro | Leu | Ser | Val | Glu | Asn | Gln | Ile |

|  | 2600 |  |  | 2609 |  |  | 2618 |  |  | 2627 |  |
|---|---|---|---|---|---|---|---|---|---|---|---|
| GGA | CCT | TGT | GGA | GAA | CCG | AAT | CGA | TGC | GCG | CCA | CAC | CTT |
| Gly | Pro | Cys | Gly | Glu | Pro | Asn | Arg | Cys | Ala | Pro | His | Leu |

FIG. 13L

```
      2636            2645            2654            2663
GAA TGG AAT CCT GAT TTA CAC TGT TCC TGC AGA GAC GGG
Glu Trp Asn Pro Asp Leu His Cys Ser Cys Arg Asp Gly 2672            2681            2690            2699            2708
GAA AAA TGT GCA CAT CAT TCT CAT CAT TTC TCT TTG GAC
Glu Lys Cys Ala His His Ser His His Phe Ser Leu Asp 2717            2726            2735            2744
ATT GAT GTT GGA TGT ACA GAC TTA AAT GAG GAC TTA GGT
Ile Asp Val Gly Cys Thr Asp Leu Asn Glu Asp Leu Gly 2753            2762            2771            2780
GTA TGG GTG ATA TTC AAG ATT AAG ACG CAA GAT GGC CAC
Val Trp Val Ile Phe Lys Ile Lys Thr Gln Asp Gly His 2789            2798            2807            2816            2825
GCA CGA CTA GGG AAT CTA GAG TTT CTC GAA GAG AAA CCA
Ala Arg Leu Gly Asn Leu Glu Phe Leu Glu Glu Lys Pro 2834            2843            2852            2861
TTA TTA GGA GAA GCA CTA GCT CGT GTG AAA AGA GCG GAG
Leu Leu Gly Glu Ala Leu Ala Arg Val Lys Arg Ala Glu
```

FIG. 13M

```
        2870            2879            2888            2897
AAA AAA TGG AGA GAC AAA CGC GAA ACA TTA CAA TTG GAA
Lys Lys Trp Arg Asp Lys Arg Glu Thr Leu Gln Leu Glu 2906            2915            2924            2933            2942
ACA ACT ATC GTT TAT AAA GAG GCA AAA GAA TCT GTA GAT
Thr Thr Ile Val Tyr Lys Glu Ala Lys Glu Ser Val Asp 2951            2960            2969            2978
GCT TTA TTT GTA AAC TCT CAA TAT GAT AGA TTA CAA GCG
Ala Leu Phe Val Asn Ser Gln Tyr Asp Arg Leu Gln Ala 2987            2996            3005            3014
GAT ACG AAC ATC GCG ATG ATT CAT GCG GCA GAT AAA CGC
Asp Thr Ash Ile Ala MET Ile His Ala Ala Asp Lys Arg 3023            3032            3041            3050            3059
GTT CAT AGA ATT CGA GAA GCG TAT CTG CCG GAG CTG TCT
Val His Arg Ile Arg Glu Ala Tyr Leu Pro Glu Leu Ser 3068            3077            3086            3095
GTG ATT CCG GGT GTC AAT GCG GCT ATT TTT GAA GAA TTA
Val Ile Pro Gly Val Asn Ala Ala Ile Phe Glu Glu Leu
```

FIG. 13N

```
     3104            3113            3122            3131
GAA GAG CGT ATT TTC ACT GCA TTT TCC CTA TAT GAT GCG
Glu Glu Arg Ile Phe Thr Ala Phe Ser Leu Tyr Asp Ala 3140            3149            3158            3167            3176
AGA AAT ATT ATT AAA AAT GGC GAT TTC AAT AAT GGC TTA
Arg Asn Ile Ile Lys Asn Gly Asp Phe Asn Asn Gly Leu 3185            3194            3203            3212
TTA TGC TGG AAC GTG AAA GGG CAT GTA GAG GTA GAA GAA
Leu Cys Trp Asn Val Lys Gly His Val Glu Val Glu Glu 3221            3230            3239            3248
CAA AAC AAT CAC CGT TCA GTC CTG GTT ATC CCA GAA TGG
Gln Asn Asn His Arg Ser Val Leu Val Ile Pro Glu Trp 3257            3266            3275            3284            3293
GAG GCA GAA GTG TCA CAA GAG GTT CGT GTC TGT CCA GGT
Glu Ala Glu Val Ser Gln Glu Val Arg Val Cys Pro Gly 3302            3311            3320            3329
CGT GGC TAT ATC CTT CGT GTT ACA GCG TAC AAA GAG GGA
Arg Gly Tyr Ile Leu Arg Val Thr Ala Tyr Lys Glu Gly
```

FIG. 13P

|  | 3338 |  |  | 3347 |  |  | 3356 |  |  | 3365 |  |
|---|---|---|---|---|---|---|---|---|---|---|---|
| TAT | GGA | GAA | GGT | TGC | GTA | ACG | ATC | CAT | GAG | ATC | GAG | AAC |
| Tyr | Gly | Glu | Gly | Cys | Val | Thr | Ile | His | Glu | Ile | Glu | Asn |

| 3374 |  |  | 3383 |  |  | 3392 |  |  | 3401 |  | 3410 |
|---|---|---|---|---|---|---|---|---|---|---|---|
| AAT | ACA | GAC | GAA | CTG | AAA | TTC | AAC | AAC | TGT | GTA | GAA | GAG |
| Asn | Thr | Asp | Glu | Leu | Lys | Phe | Asn | Asn | Cys | Val | Glu | Glu |

|  | 3419 |  |  | 3428 |  |  | 3437 |  |  | 3446 |  |
|---|---|---|---|---|---|---|---|---|---|---|---|
| GAA | GTA | TAT | CCA | AAC | AAC | ACG | GTA | ACG | TGT | ATT | AAT | TAT |
| Glu | Val | Tyr | Pro | Asn | Asn | Thr | Val | Thr | Cys | Ile | Asn | Tyr |

|  | 3455 |  |  | 3464 |  |  | 3473 |  |  | 3482 |  |
|---|---|---|---|---|---|---|---|---|---|---|---|
| ACT | GCG | ACT | CAA | GAA | GAA | TAT | GAG | GGT | ACG | TAC | ACT | TCT |
| Thr | Ala | Thr | Gln | Glu | Glu | Tyr | Glu | Gly | Thr | Tyr | Thr | Ser |

| 3491 |  |  | 3500 |  |  | 3509 |  |  | 3518 |  | 3527 |
|---|---|---|---|---|---|---|---|---|---|---|---|
| CGT | AAT | CGA | GGA | TAT | GAC | GAA | GCC | TAT | GGT | AAT | AAC | CCT |
| Arg | Asn | Arg | Gly | Tyr | Asp | Glu | Ala | Tyr | Gly | Asn | Asn | Pro |

|  | 3536 |  |  | 3545 |  |  | 3554 |  |  | 3563 |  |
|---|---|---|---|---|---|---|---|---|---|---|---|
| TCC | GTA | CCA | GCT | GAT | TAT | GCG | TCA | GTC | TAT | GAA | GAA | AAA |
| Ser | Val | Pro | Ala | Asp | Tyr | Ala | Ser | Val | Tyr | Glu | Glu | Lys |

FIG. 13Q

```
     3572              3581              3590              3599
TCG TAT ACA GAT AGA CGA AGA GAG AAT CCT TGT GAA TCT
Ser Tyr Thr Asp Arg Arg Arg Glu Asn Pro Cys Glu Ser 3608              3617              3626              3635              3644
AAC AGA GGA TAT GGA GAT TAC ACA CCA CTA CCA GCT GGT
Asn Arg Gly Tyr Gly Asp Tyr Thr Pro Leu Pro Ala Gly 3653              3662              3671              3680
TAT GTA ACA AAG GAA TTA GAG TAC TTC CCA GAG ACC GAT
Tyr Val Thr Lys Glu Leu Glu Tyr Phe Pro Glu Thr Asp 3689              3698              3707              3716
AAG GTA TGG ATT GAG ATT GGA GAA ACA GAA GGA ACA TTC
Lys Val Trp Ile Glu Ile Gly Glu Thr Glu Gly Thr Phe 3725              3734              3743              3752              3761
ATC GTG GAC AGC GTG GAA TTA CTC CTT ATG GAG GAA TAG
Ile Val Asp Ser Val Glu Leu Leu Leu MET Glu Glu  •
```

FIG. 13R

```
     3771        3781        3791        3801        3811
GACCATCCGA GTATAGCAGT TTAATAAATA TTAATTAAAA TAGTAGTCTA 3821        3831        3841        3851        3861
ACTTCCGTTC CAATTAAATA AGTAAATTAC AGTTGTAAAA AAAAACGAAC 3871        3881        3891        3901
ATTACTCTTC AAAGAGCGAT GTCCGTTTTT TATATGGTGT GT
```

FIG. 14A

```
          10         20         30         40         50
AATAGAATCT CAAATCTCGA TGACTGCTTA GTCTTTTTAA TACTGTCTAC 60         70         80         90        100
TTGACAGGGG TAGGAACATA ATCGGTCAAT TTTAAATATG GGCATATAT 110        120        130        140        150
TGATATTTTA TAAAATTTGT TACGTTTTTT GTATTTTTTC ATAAGATGTG 160        170        180        190        200
TCATATGTAT TAAATCGTGG TAATGAAAAA CAGTATCAAA CTATCAGAAC 210        220        230        239
TTTGGTAGTT TAATAAAAAA ACGGAGGTAT TTT ATG GAG GAA
                                 ----- MET Glu Glu
```

```
   248         257         266         275
AAT AAT CAA AAT CAA TGC ATA CCT TAC AAT TGT TTA AGT
Asn Asn Gln Asn Gln Cys Ile Pro Tyr Asn Cys Leu Ser 284         293         302         311         320
AAT CCT GAA GAA GTA CTT TTG GAT GGA GAA CGG ATA TCA
Asn Pro Glu Glu Val Leu Leu Asp Gly Glu Arg Ile Ser
```

FIG. 14B

```
     329              338              347              356
ACT GGT AAT TCA TCA ATT GAT ATT TCT CTG TCA CTT GTT
Thr Gly Asn Ser Ser Ile Asp Ile Ser Leu Ser Leu Val 365              374              383              392
CAG TTT ATG GTA TCT AAC TTT GTA CCA GGG GGA GGA TTT
Gln Phe Leu Val Ser Asn Phe Val Pro Gly Gly Gly Phe 401              410              419              428              437
TTA GTT GGA TTA ATA GAT TTT GTA TGG GGA ATA GTT GGC
Leu Val Gly Leu Ile Asp Phe Val Trp Gly Ile Val Gly 446              455              464              473
CCT TCT CAA TGG GAT GCA TTT CTA GTA CAA ATT GAA CAA
Pro Ser Gln Trp Asp Ala Phe Leu Val Gln Ile Glu Gln 482              491              500              509
TTA ATT AAT GAA AGA ATA GCT GAA TTT GCT AGG AAT GCT
Leu Ile Asn Glu Arg Ile Ala Glu Phe Ala Arg Asn Ala 518              527              536              545              554
GCT ATT GCT AAT TTA GAA GGA TTA GGA AAC AAT TTA AAT
Ala Ile Ala Asn Leu Glu Gly Leu Gly Asn Asn Phe Asn
```

FIG. 14C

```
         563              572              581              590
ATA TAT GTG GAA GCA TTT AAA GAA TGG GAA GAA GAT CCT
Ile Tyr Val Glu Ala Phe Lys Glu Trp Glu Glu Asp Pro 599              608              617              626
AAT AAT CCA GAA ACC AGG ACC AGA GTA ATT GAT CGC TTT
Asn Asn Pro Glu Thr Arg Thr Arg Val Ile Asp Arg Phe 635              644              653              662              671
CGT ATA CTT GAT GGG CTA CTT GAA AGG GAC ATT CCT TCG
Arg Ile Leu Asp Gly Leu Leu Glu Arg Asp Ile Pro Ser 680              689              698              707
TTT CGA ATT TCT GGA TTT GAA GTA CCC CTT TTA TCC GTT
Phe Arg Ile Ser Gly Phe Glu Val Pro Leu Leu Ser Val 716              725              734              743
TAT GCT CAA GCG GCC AAT CTG CAT CTA GCT ATA TTA AGA
Tyr Ala Gln Ala Ala Asn Leu His Leu Ala Ile Leu Arg 752              761              770              779              788
GAT TCT GTA ATT TTT GGA GAA AGA TGG GGA TTG ACA ACG
Asp Ser Val Ile Phe Gly Glu Arg Trp Gly Leu Thr Thr
```

FIG. 14D

```
      797             806             815             824
ATA AAT GTC AAT GAA AAC TAT AAT AGA CTA ATT AGG CAT
Ile Asn Val Asn Glu Asn Tyr Asn Arg Leu Ile Arg His 833             842             851             860
ATT GAT GAA TAT GCT GAT CAC TGT GCA AAT ACG TAT AAT
Ile Asp Glu Tyr Ala Asp His Cys Ala Asn Thr Tyr Asn 869             878             887             896             905
CGG GGA TTA AAT AAT TTA CCG AAA TCT ACG TAT CAA GAT
Arg Gly Leu Asn Asn Leu Pro Lys Ser Thr Tyr Gln Asp 914             923             932             941
TGG ATA ACA TAT AAT CGA TTA CGG AGA GAC TTA ACA TTG
Trp Ile Thr Tyr Asn Arg Leu Arg Arg Asp Leu Thr Leu 950             959             968             977
ACT GTA TTA GAT ATC GCC GCT TTC TTT CCA AAC TAT GAC
Thr Val Leu Asp Ile Ala Ala Phe Phe Pro Asn Tyr Asp 986             995            1004            1013            1022
AAT AGG AGA TAT CCA ATT CAG CCA GTT GGT CAA CTA ACA
Asn Arg Arg Tyr Pro Ile Gln Pro Val Gly Gln Leu Thr
```

FIG. 14E

```
        1031              1040             1049            1058
AGG  GAA  GTT  TAT  ACG  GAC  CCA  TTA  ATT  AAT  TTT  AAT  CCA
Arg  Glu  Val  Tyr  Thr  Asp  Pro  Leu  Ile  Asn  Phe  Asn  Pro 1067              1076             1085            1094
CAG  TTA  CAG  TCT  GTA  GCT  CAA  TTA  CCT  ACT  TTT  AAC  GTT
Gln  Leu  Gln  Ser  Val  Ala  Gln  Leu  Pro  Thr  Phe  Asn  Val 1103              1112             1121            1130            1139
ATG  GAG  AGC  AGC  GCA  ATT  AGA  AAT  CCT  CAT  TTA  TTT  GAT
MET  Glu  Ser  Ser  Ala  Ile  Arg  Asn  Pro  His  Leu  Phe  Asp 1148              1157             1166            1175
ATA  TTG  AAT  AAT  CTT  ACA  ATC  TTT  ACG  GAT  TGG  TTT  AGT
Ile  Leu  Asn  Asn  Leu  Thr  Ile  Phe  Thr  Asp  Trp  Phe  Ser 1184              1193             1202            1211
GTT  GGA  CGC  AAT  TTT  TAT  TGG  GGA  GGA  CAT  CGA  GTA  ATA
Val  Gly  Arg  Asn  Phe  Tyr  Trp  Gly  Gly  His  Arg  Val  Ile 1220              1229             1238            1247            1256
TCT  AGC  CTT  ATA  GGA  GGT  GGT  AAC  ATA  ACA  TCT  CCT  ATA
Ser  Ser  Leu  Ile  Gly  Gly  Gly  Asn  Ile  Thr  Ser  Pro  Ile
```

FIG. 14F

```
        1265            1274            1283            1292
TAT GGA AGA GAG GCG AAC CAG GAG CCT CCA AGA TCC TTT
Tyr Gly Arg Glu Ala Asn Gln Glu Pro Pro Arg Ser Phe 1301            1310            1319            1328
ACT TTT AAT GGA CCG GTA TTT AGG ACT TTA TCA AAT CCT
Thr Phe Asn Gly Pro Val Phe Arg Thr Leu Ser Asn Pro 1337            1346            1355            1364            1373
ACT TTA CGA TTA TTA CAG CAA CCT TGG CCA GCG CCA CCA
Thr Leu Arg Leu Leu Gln Gln Pro Trp Pro Ala Pro Pro 1382            1391            1400            1409
TTT AAT TTA CGT GGT GTT GAA GGA GTA GAA TTT TCT ACA
Phe Ash Leu Arg Gly Val Glu Gly Val Glu Phe Ser Thr 1418            1427            1436            1445
CCT ACA AAT AGC TTT ACG TAT CGA GGA AGA GGT ACG GTT
Pro Thr Asn Ser Phe Thr Tyr Arg Gly Arg Gly Thr Val 1454            1463            1472            1481            1490
GAT TCT TTA ACT GAA TTA CCG CCT GAG GAT AAT AGT GTG
Asp Ser Leu Thr Glu Leu Pro Pro Glu Asp Asn Ser Val
```

FIG. 14G

```
        1499            1508            1517            1526
CCA CCT CGC GAA GGA TAT AGT CAT CGT TTA TGT CAT GCA
Pro Pro Arg Glu Gly Tyr Ser His Arg Leu Cys His Ala 1535            1544            1553            1562
ACT TTT GTT CAA AGA TCT GGA ACA CCT TTT TTA ACA ACT
Thr Phe Val Gln Arg Ser Gly Thr Pro Phe Leu Thr Thr 1571            1580            1589            1598            1607
GGT GTA GTA TTT TCT TGG ACG CAT CGT AGT GCA ACT CTT
Gly Val Val Phe Ser Trp Thr His Arg Ser Ala Thr Leu 1616            1625            1634            1643
ACA AAT ACA ATT GAT CCA GAG AGA ATT AAT CAA ATA CCT
Thr Asn Thr Ile Asp Pro Glu Arg Ile Asn Gln Ile Pro 1652            1661            1670            1679
TTA GTG AAA GGA TTT AGA GTT TGG GGG GGC ACC TCT GTC
Leu Val Lys Gly Phe Arg Val Trp Gly Gly Thr Ser Val 1688            1697            1706            1715            1724
ATT ACA GGA CCA GGA TTT ACA GGA GGG GAT ATC CTT CGA
Ile Thr Gly Pro Gly Phe Thr Gly Gly Asp Ile Leu Arg
```

FIG. 14H

```
         1733            1742           1751           1760
AGA AAT ACC TTT GGT GAT TTT GTA TCT CTA CAA GTC AAT
Arg Asn Thr Phe Gly Asp Phe Val Ser Leu Gln Val Asn 1769            1778           1787           1796
ATT AAT TCA CCA ATT ACC CAA AGA TAC CGT TTA AGA TTT
Ile Asn Ser Pro Ile Thr Gln Arg Tyr Arg Leu Arg Phe 1805            1814           1823           1832           1841
CGT TAC GCT TCC AGT AGG GAT GCA CGA GTT ATA GTA TTA
Arg Tyr Ala Ser Ser Arg Asp Ala Arg Val Ile Val Leu 1850            1859           1868           1877
ACA GGA GCG GCA TCC ACA GGA GTG GGA GGC CAA GTT AGT
Thr Gly Ala Ala Ser Thr Gly Val Gly Gly Gln Val Ser 1886            1895           1904           1913
GTA AAT ATG CCT CTT CAG AAA ACT ATG GAA ATA GGG GAG
Val Asn MET Pro Leu Gln Lys Thr MET Glu Ile Gly Glu 1922            1931           1940           1949           1958
AAC TTA ACA TCT AGA ACA TTT AGA TAT ACC GAT TTT AGT
Asn Leu Thr Ser Arg Thr Phe Arg Tyr Thr Asp Phe Ser
```

FIG. 14I

```
        1967            1976            1985            1994
AAT CCT TTT TCA TTT AGA GCT AAT CCA GAT ATA ATT GGG
Asn Pro Phe Ser Phe Arg Ala Asn Pro Asp Ile Ile Gly 2003            2012            2021            2030
ATA AGT GAA CAA CCT CTA TTT GGT GCA GGT TCT ATT AGT
Ile Ser Glu Gln Pro Leu Phe Gly Ala Gly Ser Ile Ser 2039            2048            2057            2066            2075
AGC GGT GAA CTT TAT ATA GAT AAA ATT GAA ATT ATT CTA
Ser Gly Glu Leu Tyr Ile Asp Lys Ile Glu Ile Ile Leu 2084            2093            2102            2111
GCA GAT GCA ACA TTT GAA GCA GAA TCT GAT TTA GAA AGA
Ala Asp Ala Thr Phe Glu Ala Glu Ser Asp Leu Glu Arg 2120            2129            2138            2147
GCA CAA AAG GCG GTG AAT GCC CTG TTT ACT TCT TCC AAT
Ala Gln Lya Ala Val Asn Ala Leu Phe Thr Ser Ser Asn 2156            2165            2174            2183            2192
CAA ATC GGG TTA AAA ACC GAT GTG ACG GAT TAT CAT ATT
Gln Ile Gly Leu Lys Thr Asp Val Thr Asp Tyr His Ile
```

FIG. 14J

```
       2201            2210            2219            2228
GAT CAA GTA TCC AAT TTA GTG GAT TGT TTA TCA GAT GAA
Asp Gln Val Ser Asn Leu Val Asp Cys Leu Ser Asp Glu 2237            2246            2255            2264
TTT TGT CTG GAT GAA AAG CGA GAA TTG TCC GAG AAA GTC
Phe Cys Leu Asp Glu Lys Arg Glu Leu Ser Glu Lys Val 2273            2282            2291            2300            2309
AAA CAT GCG AAG CGA CTC AGT GAT GAG CGG AAT TTA CTT
Lys His Ala Lys Arg Leu Ser Asp Glu Arg Asn Leu Leu 2318            2327            2336            2345
CAA GAT CCA AAC TTC AGA GGG ATC AAT AGA CAA CCA GAC
Gln Asp Pro Asn Phe Arg Gly Ile Asn Arg Gln Pro Asp 2354            2363            2372            2381
CGT GGC TGG AGA GGA AGT ACA GAT ATT ACC ATC CAA GGA
Arg Gly Trp Arg Gly Ser Thr Asp Ile Thr Ile Gln Gly 2390            2399            2408            2417            2426
GGA GAT GAC GTA TTC AAA GAG AAT TAC GTC ACA CTA CCG
Gly Asp Asp Val Phe Lys Glu Asn Tyr Val Thr Leu Pro
```

FIG. 14K

```
     2435            2444            2453            2462
GGT ACC GTT GAT GAG TGC TAT CCA ACG TAT TTA TAT CAG
Gly Thr Val Asp Glu Cys Tyr Pro Thr Tyr Leu Tyr Gln 2471            2480            2489            2498
AAA ATA GAT GAG TCG AAA TTA AAA GCT TAT ACC CGT TAT
Lys Ile Asp Glu Ser Lys Leu Lys Ala Tyr Thr Arg Tyr 2507            2516            2525            2534            2543
GAA TTA AGA GGG TAT ATC GAA GAT AGT CAA GAC TTA GAA
Glu Leu Arg Gly Tyr Ile Glu Asp Ser Gln Asp Leu Glu 2552            2561            2570            2579
ATC TAT TTG ATC CGT TAC AAT GCA AAA CAC GAA ATA GTA
Ile Tyr Leu Ile Arg Tyr Asn Ala Lys His Glu Ile Val 2588            2597            2606            2615
AAT GTG CCA GGC ACG GGT TCC TTA TGG CCG CTT TCA GCC
Asn Val Pro Gly Thr Gly Ser Leu Trp Pro Leu Ser Ala 2624            2633            2642            2651            2660
CAA AGT CCA ATC GGA AAG TGT GGA GAA CCG AAT CGA TGC
Gln Ser Pro Ile Gly Lys Cys Gly Glu Pro Asn Arg Cys
```

FIG. 14L

```
       2669            2678             2687           2696
GCG CCA CAC CTT GAA TGG AAT CCT GAT CTA GAT TGT TCC
Ala Pro His Leu Glu Trp Asn Pro Asp Leu Asp Cys Ser 2705            2714            2723           2732
TGC AGA GAC GGG GAA AAA TGT GCA CAT CAT TCC CAT CAT
Cys Arg Asp Gly Glu Lys Cys Ala His His Ser His His 2741           2750            2759            2768           2777
TTC ACC TTG GAT ATT GAT GTT GGA TGT ACA GAC TTA AAT
Phe Thr Leu Asp Ile Asp Val Gly Cys Thr Asp Leu Asn 2786            2795            2804           2813
GAG GAC TTA GGT GTA TGG GTG ATA TTC AAG ATT AAG ACG
Glu Asp Leu Gly Val Trp Val Ile Phe Lys Ile Lys Thr 2822            2831            2840           2849
CAA GAT GGC CAT GCA AGA CTA GGG AAT CTA GAG TTT CTC
Gln Asp Gly His Ala Arg Leu Gly Asn Leu Glu Phe Leu 2858           2867            2876            2885           2894
GAA GAG AAA CCA TTA TTA GGG GAA GCA CTA GCT CGT GTG
Glu Glu Lys Pro Leu Leu Gly Glu Ala Leu Ala Arg Val
```

FIG. 14M

```
       2903            2912            2921            2930
AAA AGA GCG GAG AAG AAG TGG AGA GAC AAA CGA GAG AAA
Lys Arg Ala Glu Lys Lys Trp Arg Asp Lys Arg Glu Lys 2939            2948            2957            2966
CTG CAG TTG GAA ACA AAT ATT GTT TAT AAA GAG GCA AAA
Leu Gln Leu Glu Thr Asn Ile Val Tyr Lys Glu Ala Lys 2975           2984            2993            3002            3011
GAA TCT GTA GAT GCT TTA TTT GTA AAC TCT CAA TAT GAT
Glu Ser Val Asp Ala Leu Phe Val Asn Ser Gln Tyr Asp 3020            3029            3038            3047
AGA TTA CAA GTG GAT ACG AAC ATC GCG ATG ATT CAT GCG
Arg Leu Gln Val Asp Thr Asn Ile Ala MET Ile His Ala 3056            3065            3074            3083
GCA GAT AAA CGC GTT CAT AGA ATC CGG GAA GCG TAT CTG
Ala Asp Lys Arg Val His Arg Ile Arg Glu Ala Tyr Leu 3092           3101            3110            3119            3128
CCA GAG TTG TCT GTG ATT CCA GGT GTC AAT GCG GCC ATT
Pro Glu Leu Ser Val Ile Pro Gly Val Asn Ala Ala Ile
```

FIG. 14N

```
      3137              3146              3155              3164
TTC GAA GAA TTA GAG GGA CGT ATT TTT ACA GCG TAT TCC
Phe Glu Glu Leu Glu Gly Arg Ile Phe Thr Ala Tyr Ser 3173              3182              3191              3200
TTA TAT GAT GCG AGA AAT GTC ATT AAA AAT GGC GAT TTC
Leu Tyr Asp Ala Arg Asn Val Ile Lys Asn Gly Asp Phe 3209              3218              3227              3236              3245
AAT AAT GGC TTA TTA TGC TGG AAC GTG AAA GGT CAT GTA
Asn Asn Gly Leu Leu Cys Trp Asn Val Lys Gly His Val 3254              3263              3272              3281
GAT GTA GAA GAG CAA AAC AAC CAC CGT TCG GTC CTT GTT
Asp Val Glu Glu Gln Asn Asn His Arg Ser Val Leu Val 3290              3299              3308              3317
ATC CCA GAA TGG GAG GCA GAA GTG TCA CAA GAG GTT CGT
Ile Pro Glu Trp Glu Ala Glu Val Ser Gln Glu Val Arg 3326              3335              3344              3353              3362
GTC TGT CCA GGT CGT GGC TAT ATC CTT CGT GTC ACA GCA
Val Cys Pro Gly Arg Gly Tyr Ile Leu Arg Val Thr Ala
```

FIG. 14P

|  | 3371 |  |  | 3380 |  |  | 3389 |  |  | 3398 |  |
|---|---|---|---|---|---|---|---|---|---|---|---|
| TAT | AAA | GAG | GGA | TAT | GGA | GAG | GGC | TGC | GTA | ACG | ATC | CAT |
| Tyr | Lys | Glu | Gly | Tyr | Gly | Glu | Gly | Cys | Val | Thr | Ile | His |

|  | 3407 |  |  | 3416 |  |  | 3425 |  |  | 3434 |  |
|---|---|---|---|---|---|---|---|---|---|---|---|
| GAG | ATC | GAA | GAC | AAT | ACA | GAC | GAA | CTG | AAA | TTC | AGC | AAC |
| Glu | Ile | Glu | Asp | Asn | Thr | Asp | Glu | Leu | Lys | Phe | Ser | Asn |

| 3443 |  |  | 3452 |  |  | 3461 |  |  | 3470 |  |  | 3479 |
|---|---|---|---|---|---|---|---|---|---|---|---|---|
| TGT | GTA | GAA | GAG | GAA | GTA | TAT | CCA | AAC | AAC | ACA | GTA | ACG |
| Cys | Val | Glu | Glu | Glu | Val | Tyr | Pro | Asn | Asn | Thr | Val | Thr |

|  | 3488 |  |  | 3497 |  |  | 3506 |  |  | 3515 |  |
|---|---|---|---|---|---|---|---|---|---|---|---|
| TGT | AAT | AAT | TAT | ACT | GGG | ACT | CAA | GAA | GAA | TAT | GAG | GGT |
| Cys | Asn | Asn | Tyr | Thr | Gly | Thr | Gln | Glu | Glu | Tyr | Glu | Gly |

|  | 3524 |  |  | 3533 |  |  | 3542 |  |  | 3551 |  |
|---|---|---|---|---|---|---|---|---|---|---|---|
| ACG | TAC | ACT | TCT | CGT | AAT | CAA | GGA | TAT | GAC | GAA | GCC | TAT |
| Thr | Tyr | Thr | Ser | Arg | Asn | Gln | Gly | Tyr | Asp | Glu | Ala | Tyr |

| 3560 |  |  | 3569 |  |  | 3578 |  |  | 3587 |  |  | 3596 |
|---|---|---|---|---|---|---|---|---|---|---|---|---|
| GGT | AAT | AAC | CCT | TCC | GTA | CCA | GCT | GAT | TAC | GCT | TCA | GTC |
| Gly | Asn | Asn | Pro | Ser | Val | Pro | Ala | Asp | Tyr | Ala | Ser | Val |

FIG. 14Q

```
         3605           3614           3623           3632
TAT GAA GAA AAA TCG TAT ACA GAT GGA CGA AGA GAG AAT
Tyr Glu Glu Lys Ser Tyr Thr Asp Gly Arg Arg Glu Asn 3641           3650           3659           3668
CCT TGT GAA TCT AAC AGA GGC TAT GGG GAT TAC ACA CCA
Pro Cys Glu Ser Asn Arg Gly Tyr Gly Asp Tyr Thr Pro 3677           3686           3695           3704           3713
CTA CCG GCT GGT TAT GTA ACA AAG GAT TTA GAG TAC TTC
Leu Pro Ala Gly Tyr Val Thr Lys Asp Leu Glu Tyr Phe 3722           3731           3740           3749
CCA GAG ACC GAT AAG GTA TGG ATT GAG ATC GGA GAA ACA
Pro Glu Thr Asp Lys Val Trp Ile Glu Ile Gly Glu Thr 3758           3767           3776           3785
GAA GGA ACA TTC ATC GTG GAT AGC GTG GAA TTA CTC CTT
Glu Gly Thr Phe Ile Val Asp Ser Val Glu Leu Leu Leu 3794           3803           3813           3823           3833
ATG GAG GAA TAA GATACGTTAT AAAATGTAAC GTATGCAAAT
MET Glu Glu  •
```

FIG. 14R

```
     3843        3853        3863        3873        3883
AAAGAATGAT TACTGACCTA TATTAACAGA TAAATAAGAA AATTTTTATA 3893        3903        3913        3923
CGAATAAAAA ACGGACATCA CTCTTAAGAG AATGATGTCC
```

RECOMBINANT PLANT EXPRESSING NON-COMPETITIVELY BINDING INSECTICIDAL CRYSTAL PROTEINS

This application is a continuation, of application Ser. No. 08/173,274, filed Dec. 23, 1993, now abandoned, which is a continuation of application Ser. No. 07/640,400, filed Jan. 22, 1991, now abandoned.

This invention relates to plant cells and plants, the genomes of which are transformed to contain at least two genes, each coding for a different non-competitively binding *Bacillus thuringiensis* ("*B.thuringiensis*" or "Bt") insecticidal crystal protein ("ICP") for a specific target insect species, preferably belonging to the order of Lepidoptera or Coleoptera. Such transformed plants have advantages over plants transformed with a single *B. thuringiensis* ICP gene, especially with respect to the prevention of resistance development in the target insect species against the at least two *B. thuringiensis* ICPs, expressed in such plants.

This invention also relates to a process for the production of such transgenic plants, taking into account the competitive and non-competitive binding properties of the at least two *B. thuringiensis* ICPs in the target insect species' midgut. Simultaneous expression in plants of the at least two genes, each coding for a different non-competitively binding *B. thuringiensis* ICP in plants, is particularly useful to prevent or delay resistance development of insects against the at least two *B. thuringiensis* ICPs expressed in the plants.

This invention further relates to a process for the construction of novel plant expression vectors and to the novel plant expression vectors themselves, which contain the at least two *B. thuringiensis* ICP genes encoding the at least two non-competitively binding *B. thuringiensis* ICPs. Such vectors allow integration and coordinate expression of the at least two *B. thuringiensis* ICP genes in plants.

BACKGROUND OF THE INVENTION

Since the development and the widespread use of chemical insecticides, the occurrence of resistant insect strains has been an important problem. Development of insecticide resistance is a phenomenon dependent on biochemical, physiological, genetic and ecological mechanisms. Currently, insect resistance has been reported against all major classes of chemical insecticides including chlorinated hydrocarbons, organophosphates, carbamates, and pyrethroid compounds (Brattsten et al., 1986).

In contrast to the rapid development of insect resistance to synthetic insecticides, development of insect resistance to bacterial insecticides such as *B. thuringiensis* sprays has evolved slowly despite many years of use (Brattsten et al., 1986). The spore forming gram-positive bacterium *B. thuringiensis* produces a parasporal crystal which is composed of crystal proteins (ICPs) having insecticidal activity. Important factors decreasing the probability of emergence of resistant insect strains in the field against *B. thuringiensis* sprays are: firstly the short half-life of *B. thuringiensis* sprays after foliar application; secondly the fact that commercial *B. thuringiensis* preparations often consist of a mixture of several insecticidal factors including spores, ICPs and eventually beta-exotoxins (Shields, 1987); and thirdly the transitory nature of plant-pest interactions. Many successful field trials have shown that commercial preparations of a *B. thuringiensis* containing its spore-crystal complex, effectively control lepidopterous pests in agriculture and forestry (Krieg and Langenbruch, 1981). *B. thuringiensis* is at present the most widely used pathogen for microbial control of insect pests.

Various laboratory studies, in which selection against *B. thuringiensis* was applied over several generations of insects, have confirmed that resistance against *B. thuringiensis* is seldom obtained. However, it should be emphasized that the laboratory conditions represented rather low selection pressure conditions.

For example, Goldman et al. (1986) have applied selection with *B. thuringiensis israelensis* toxin over 14 generations of *Aedes aegypti* and found only a marginal decrease in sensitivity. The lack of any observable trend toward decreasing susceptibility in the selected strains may be a reflection of the low selection pressure ($LC_{50}$) carried out over a limited number of generations. However, it should be pointed out that Georghiou et al. (In: Insecticide Resistance in Mosquitoes: Research on new chemicals and techniques for management. In "Mosquito Control Research, Annual Report 1983, University of California.") with *Culex quinquefasciatus* obtained an 11-fold increase in resistance to *B. thuringiensis israelensis* after 32 generations at $LC_{95}$ selection presssure.

McGaughey (1985) reported that the grain storage pest *Plodia interpunctella* developed resistance to the spore-crystal complex of *B. thuringiensis*; after 15 generations of selection with the Indian meal moth, *Plodia interpunctella*, using a commercial *B. thuringiensis* HD-1 preparation ("Dipel", Abbott Laboratories, North Chicago, Ill. 60064, USA), a 100-fold decrease in *B. thuringiensis* sensitivity was reported. Each of the colonies was cultured for several generations on a diet treated with a constant *B. thuringiensis* dosage which was expected to produce 70–90% larval mortality. Under these high selection presssure conditions, insect resistance to *B. thuringiensis* increased rapidly. More recently, development of resistance against *B. thuringiensis* is also reported for the almond moth, *Cadra cautella* (McGaughey and Beeman, 1988). Resistance was stable when selection was discontinued and was inherited as a recessive trait (McGaughey and Beeman, 1988). The mechanism of insect resistance to *B. thuringiensis* toxins of *Plodia interpunctella* and *Cadra cautella* has not been elucidated.

The main cause of *B. thuringiensis* resistance development in both reported cases involving grain storage was the environmental conditions prevailing during the grain storage. Under the conditions in both cases, the environment was relatively stable, so *B. thuringiensis* degradation was slow and permitted successive generations of the pest to breed in the continuous presence of the microbial insecticide. The speed at which Plodia developed resistance to *B. thuringiensis* in one study suggests that it could do so within one single storage season in the bins of treated grain.

Although insect resistance development against *B. thuringiensis* has mostly been observed in laboratory and pilot scale studies, very recent indications of *B. thuringiensis* resistance development in *Plutella xylostella* populations in the (cabbage) field have been reported (Kirsch and Schmutterer, 1988). A number of factors have led to a continuous exposure of *P. xylostella* to *B. thuringiensis* in a relatively small geographic area. This and the short generation cycle of *P. xylostella* have seemingly led to an enormous selection pressure resulting in decreased susceptibility and increased resistance to *B. thuringiensis*.

A procedure for expressing a *B. thuringiensis* ICP gene in plants in order to render the plants insect-resistant (European patent publication ("EP") 0193259 [which is incorporated herein by reference]; Vaeck et al., 1987; Barton et al., 1987; Fischhoff et al., 1987) provides an entirely new approach to insect control in agriculture which is at the same time safe, environmentally attractive and cost-effective. An important determinant for the success of this approach will be whether insects will be able to develop resistance to *B. thuringiensis* ICPs expressed in transgenic plants (Vaeck et al., 1987; Barton et al., 1987; Fischhoff et al., 1987). In contrast with a foliar application, after which *B. thuringiensis* ICPs are rapidly degraded, the transgenic plants will exert a continuous selection pressure. It is clear from laboratory selection experiments that a continuous selection pressure has led to adaptation to *B. thuringiensis* and its components in several insect species. In this regard, it should be pointed out that the conditions in the laboratory which resulted in the development of insect-resistance to *B. thuringiensis* are very similar to the situation with transgenic plants which produce *B. thuringiensis* ICPs and provide a continuous selection pressure on insect populations feeding on the plants. Mathematical models of selection pressure predict that, if engineered insect-resistant plants become a permanent part of their environment, resistance development in insects will emerge rapidly (Gould, 1988). Thus, the chances for the development of insect resistance to *B. thuringiensis* in transgenic plants may be considerably increased as compared to the field application of *B. thurinqiensis* sprays. A *Heliothis virescens* strain has been reported that is 20 times more resistant to *B. thuringiensis* HD-1 ICP produced by transgenic *Pseudomonas fluorescens* and 6 times more resistant to the pure ICP (Stone et al., 1989). Furthermore, the monetary and human costs of resistance are difficult to assess, but loss of pesticide effectiveness invariably entails increased application frequencies and dosages and, finally, more expensive replacement compounds as new pesticides become more difficult to discover and develop.

Therefore, it would be desirable to develop means for delaying or even preventing the evolution of resistance to *B. thuringiensis*.

*B. thuringiensis* strains, active against Lepidoptera (Dulmage et al., 1981), Diptera (Goldberg and Margalit, 1977) and Coleoptera (Krieg et al., 1983), have been described. It has become clear that there is a substantial heterogeneity among ICPs from different strains active against Lepidoptera, as well as among ICPs from strains active against Coleoptera (Hofte and Whiteley, 1989). An overview of the different *B. thuringiensis* ICP genes, that have been characterized, is given in Table 2 (which follows the Examples herein).

Most of the anti-Lepidopteran *B. thuringiensis* (e.g., Bt3, Bt2, Bt73, Bt14, Bt15, Bt4, Bt18) ICP genes encode 130 to 140 kDa protoxins which dissolve in the alkaline environment of an insect's midgut and are proteolytically activated into an active toxin of 60–65 kDa. These ICPs are related and can be recognized as members of the same family based on sequence homologies. The sequence divergence however is substantial, and the insecticidal spectrum, among the order Lepidoptera, may be substantially different (Höfte et al., 1988).

The P2 toxin gene and the cry B2 gene are different from the above-mentioned genes in that they do not encode high molecular weight protoxins but rather toxins of around 70 kDa (Donovan et al., 1988 and Widner and Whiteley, 1989, respectively).

It has recently become clear that heterogeneity exists also in the anti-Coleopteran toxin gene family. Whereas several previously reported toxin gene sequences from different *B. thuringiensis* isolates with anti-Coleopteran activity were identical (EP 0149162 and 0202739), the sequences and structure of bt21and bt22 are substantially divergent (European patent application ("EPA") 89400428.2).

While the insecticidal spectra of *B. thuringiensis* ICPs are different, the major pathway of their toxic action is believed to be common. All *B. thuringiensis* ICPs, for which the mechanism of action has been studied in any detail, interact with the midgut epithelium of sensitive species and cause lysis of the epithelial cells (Knowles and Ellar, 1986) due to the fact that the permeability characteristics of the brush border membrane and the osmotic balance over this membrane are perturbed. In the pathway of toxic action of *B. thuringiensis* ICPs, the binding of the toxin to receptor sites on the brush border membrane of these cells is an important feature (Hofmann et al., 1988b). The toxin binding sites in the midgut can be regarded as an ICP-receptor since toxin is bound in a saturable way and with high affinity (Hofmann et al., 1988a).

Although this outline of the mode of action of *B. thuringiensis* ICPs is generally accepted, it remains a matter of discussion what the essential determinant(s) are for the differences in their insecticidal spectra. Haider et al. (1986) emphasize the importance of specific proteases in the insect midgut. Hofmann et al. (1988b) indicate that receptor binding is a prerequisite for toxic activity and describe that *Pieris brassicae* has two distinct receptor populations for two toxins. Other authors have suggested that differences in the environment of the midgut (e.g., pH of the midgut) might be crucial.

SUMMARY OF THE INVENTION

In accordance with this invention, a plant is provided having, stably integrated into its genome, at least two *B. thuringiensis* ICP genes encoding at least two non-competitively binding insecticidal *B. thuringiensis* ICPs, preferably the active toxins thereof, against a specific target insect, preferably against a Lepidoptera or Coleoptera. Such a plant is characterized by the simultaneous expression of the at least two non-competitively binding *B. thuringiensis* ICPs.

Also in accordance with this invention, at least two ICP genes, particularly two genes or parts thereof coding for two non-competitively binding anti-Lepidopteran or anti-Coleopteran *B. thuringiensis* ICPs, are cloned into a plant expression vector. Plant cells transformed with this vector are characterized by the simultaneous expression of the at least two *B. thuringiensis* ICP genes. The resulting transformed plant cell can be used to produce a transformed plant in which the plant cells: 1. contain the at least two *B. thuringiensis* ICP genes or parts thereof encoding at least two non-competitively binding anti-Lepidopteran or anti-Coleopteran *B. thuringiensis* ICPs as a stable insert into their genome; and 2. express the genes simultaneously, thereby conferring on the plant improved resistance to at least one target species of insect, so as to prevent or delay development of resistance to *B. thuringiensis* of the at least one target species of insect feeding on the transformed plant.

Further in accordance with this invention, plant expression vectors are provided which allow integration and simultaneous expression of at least two *B. thuringiensis* ICP genes in a plant cell and which comprise one or more chimeric genes, each containing in the same transcriptional unit: a promoter which functions in the plant cell to direct the synthesis of mRNA encoded by one of the ICP genes; one or more different ICP genes, each encoding a non-competitively binding *B. thuringiensis* ICP; preferably a marker gene; a 3' non-translated DNA sequence which functions in the plant cell for 3' end formation and the addition of polyadenylate nucleotides to the 3' end of the mRNA; and optionally a DNA sequence encoding a protease-sensitive protein part between any two ICP genes.

BRIEF DESCRIPTION OF THE DRAWINGS

FIG. 2 is a graph showing the binding of $^{125}$I-labeled Bt3 toxin to M. sexta BBMV in the presence of increasing concentrations of Bt2 toxin (★), Bt3 toxin (●) or Bt73 toxin (▲).

FIG. 4 is a graph showing the binding of $^{125}$I-labeled Bt2 toxin to H. virescens BBMV in the presence of increasing concentrations of Bt2 toxin (★), Bt3 toxin (●) or Bt73 toxin (▲).

FIG. 5 is a graph showing the binding of $^{125}$I-labeled Bt3 toxin to H. virescens BBMV in the presence of increasing concentrations of Bt2 toxin (★), Bt3 toxin (●) or Bt73 toxin (▲).

FIG. 7 is a graph showing the binding of $^{125}$I-labeled Bt2 toxin to P. brassicae BBMV in the presence of increasing concentrations of Bt2 toxin (○) or Bt14 toxin (●).

FIG. 8 is a graph showing the binding of $^{125}$I-labeled Bt14 toxin to P. brassicae BBMV in the presence of increasing concentrations of Bt2 toxin (○) or Bt14 toxin (●).

FIG. 11 is a graph showing the binding of $^{125}$I-labeled Bt2 toxin to M. sexta BBMV in the presence of increasing concentrations of Bt2 toxin (○) or Bt18 toxin (●).

FIG. 12 is a graph showing the binding of $^{125}$I-labeled Bt18 toxin to M. sexta BBMV in the presence of increasing concentrations of Bt2 toxin (○) or Bt18 toxin (●).

FIGS. 13A–13Q depict the nucleotide sequence and deduced amino acid sequence of the open reading frame of the bt4 gene extending from nucleotide 264 to nucleotide 3761.

FIGS. 14A–14Q depict the nucleotide sequence and deduced amino acid sequence of the open reading frame of the bt15 gene extending from nucleotide 234 to nucleotide 3803.

DETAILED DESCRIPTION OF THE INVENTION

Definitions

Figure 1:
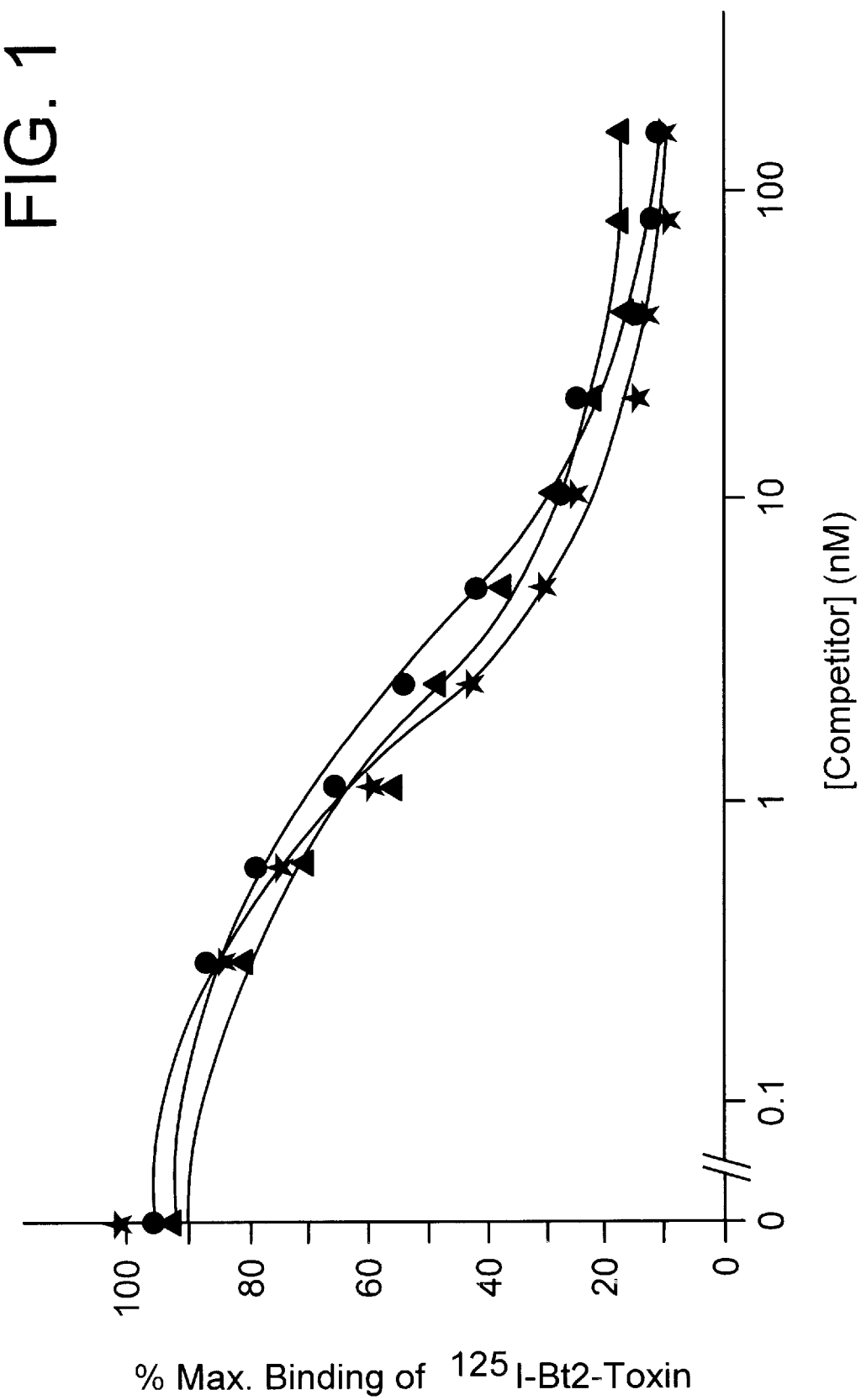
FIG. 1 is a graph showing the binding of $^{125}$I-labeled Bt2 toxin to M. sexta BBMV in the presence of increasing concentrations of Bt2 toxin (★), Bt3 toxin (●) or Bt73 toxin (▲).

As used herein, "B. thuringiensis ICP" (or "ICP") should be understood as an intact protein or a part thereof which has insecticidal activity and which can be produced in nature by B. thuringiensis. An ICP can be a protoxin, as well as an active toxin or another insecticidal truncated part of a protoxin which need not be crystalline and which need not be a naturally occurring protein. In this regard, an ICP can be a chimaeric toxin encoded by the combination of two variable regions of two different ICP genes as disclosed in EP 0228838.

As used herein, "protoxin" should be understood as the primary translation product of a full-length gene encoding an ICP.

As used herein, "toxin", "toxic core" or "active toxin" should all be understood as a part of a protoxin which can be obtained by protease (e.g., by trypsin) cleavage and has insecticidal activity.

As used herein, "gene" should be understood as a full-length DNA sequence encoding a protein (e.g., such as is found in nature), as well as a truncated fragment thereof encoding at least the active part (i.e., toxin) of the protein encoded by the full-length DNA sequence, preferably encoding just the active part of the protein encoded by the full-length DNA sequence. A gene can be naturally occurring or synthetic.

As used herein, "truncated B. thuringiensis gene" should be understood as a fragment of a full-length B. thuringiensis gene which still encodes at least the toxic part of the B. thuringiensis ICP, preferentially the toxin.

As used herein, "marker gene" should be understood as a gene encoding a selectable marker (e.g., encoding antibiotic resistance) or a screenable marker (e.g., encoding a gene product which allows the quantitative analysis of transgenic plants).

Two ICPs are said to be "competitively binding ICPs" for a target insect species when one ICP competes for all ICP receptors of the other ICP, which receptors are present in the brush border membrane of the midgut of the target insect species.

Two ICPs are said to be "non-competitively binding ICPs" when, for at least one target insect species, the first ICP has at least one receptor for which the second ICP does not compete and the second ICP has at least one receptor for which the first ICP does not compete, which receptors are present in the brush border membrane of the midgut of the target insect species.

A "receptor" should be understood as a molecule, to which a ligand (here a B. thuringiensis ICP, preferably a toxin) can bind with high affinity (typically a dissociation constant (Kd) between $10^{-11}$ and $10^{-6}$M) and saturability. A determination of whether two ICPs are competitively or non-competitively binding ICPs can be made by determining whether: 1. a first ICP competes for all of the receptors of a second ICP when all the binding sites of the second ICP with an affinity in the range of about $10^{-11}$ to $10^{-6}$M can be saturated with the first ICP in concentrations of the first ICP of about $10^{-5}$M or less (e.g., down to about $10^{-11}$M); and 2. the second ICP competes for the all of the receptors of the first ICP when all the binding sites of the first ICP with an affinity in the range of about $10^{-11}$ to $10^{-6}$M can be saturated with the second ICP in concentrations of the second ICP of about $10^{-5}$M or less.

General Procedures

This section describes in broad terms general procedures for the evaluation and exploitation of at least two B. thuringiensis ICP genes for prevention of the development, in a target insect, of a resistance to the *B. thuringiensis* ICPs expressed in transgenic plants of this invention. A non-exhaustive list of consecutive steps in the general procedure follows, after which are described particular Examples that are based on this methodology and that illustrate this invention.

In accordance with this invention, specific *B. thuringiensis* ICPs can be isolated in a conventional manner from the respective strains such as are listed in Table 2 (which follows the Examples). The ICPs can be used to prepare monoclonal or polyclonal antibodies specific for these ICPs in a conventional manner (Höfte et al., 1988).

The ICP genes can each be isolated from their respective strains in a conventional manner. Preferably, the ICP genes are each identified by: digesting total DNA from their respective strains with suitable restriction enzyme(s); size fractionating the DNA fragments, so produced, into DNA fractions of 5 to 10 Kb; ligating such fractions to suitable cloning vectors (e.g., pEcoR251, deposited at the Deutsche Sammlung von Mikroorganismen und Zellculturen ("DSM"), Braunschweig, Federal Republic of Germany, under accession number no. 4711 on Jul. 13, 1988); transforming *E.coli* with the cloning vectors; and screening the clones with a suitable DNA probe. The DNA probe can be constructed from a highly conserved region which is commonly present in different *B. thuringiensis* genes which encode crystal protoxins against Coleoptera or Lepidoptera, such as on the basis of an N-terminal amino acid sequence determined by gas-phase sequencing of the purified proteins (EPA 88402115.5).

Alternatively, the desired fragments, prepared from total DNA of the respective strains, can be ligated in suitable expression vectors (e.g., a pUC vector (Yanisch-Perron et al., 1985) with the insert under the control of the lac promoter) and transformed in *E. coli*, and the clones can then be screened by conventional colony immunoprobing methods (French et al., 1986) for expression of the toxins with monoclonal or polyclonal antibodies raised against the toxins produced by the strains.

The isolated *B. thuringiensis* ICP genes can then be sequenced in a conventional manner using well-known procedures (e.g., Maxam and Gilbert, 1980).

At present, several ICP genes have been cloned from different subspecies of *B. thuringiensis* (Table 2). The nucleotide sequences from several of these *B. thuringiensis* ICP genes have been reported. Whereas several sequences are identical or nearly identical and represent the same gene or slight variants of the same gene, several sequences display substantial heterogeneity and show the existence of different *B. thuringiensis* ICP gene classes. Several lines of evidence suggest that all these genes specify a family of related insecticidal proteins. Analysis of the distribution of *B. thuringiensis* ICPs in different *B. thuringiensis* strains by determining the protein composition of their crystals, by immunodetection using polyclonal antisera or monoclonals against purified crystals, or by using gene-specific probes, shows that subspecies of *B. thuringiensis* might contain up to three related *B. thuringiensis* ICP genes belonging to different classes (Kronstad et al., 1983).

To express the isolated and characterized gene in a heterologous host for purification and characterization of the recombinant protein, the preferred organism is *Escherichia coli*. A number of expression vectors for enhanced expression of heterologous genes in *E. coli* have been described (e.g., Remaut et al., 1981). Usually the gene is cloned under control of a strong regulatable promoter, such as the lambda pL or pR promoters (e.g., Botterman and Zabeau, 1987), the lac promoter (e.g., Fuller, 1982) or the tac promoter (e.g., De Boer et al., 1983), and provided with suitable translation initiation sites (e.g., Stanssens et al, 1985 and 1987). Gene cassettes of the *B. thuringiensis* ICP genes can be generated by site-directed mutagenesis, for example according to the procedure described by Stanssens et al. (1985 and 1987). This allows cassettes to be made comprising, for example, a truncated ICP gene fragment encoding the toxic core (i.e., toxin) of an ICP or a hybrid gene encoding the toxic core and a selectable marker according to the procedures described in EPA 88402241.9.

The cells of an *E. coli* culture, which has been induced to produce a recombinant ICP, are harvested. The method used to induce the cells to produce the recombinant ICP depends on the choice of the promoter. For example, the lac promoter (Fuller, 1982) is induced by isopropyl-B-D-thiogalactopyranoside ("IPTG"); the pL promoter is induced by temperature shock (Bernard et al., 1979). The recombinant ICP is usually deposited in the cells as insoluble inclusions (Hsuing and Becker, 1988). The cells are lysed to liberate the inclusions. The bulk of *E. coli* proteins is removed in subsequent washing steps. A semi-purified protoxin pellet is obtained, from which the protoxin can be dissolved in alkaline buffer (e.g., $Na_2CO_3$, pH 10). The procedure for the ICP Bt2, which is also applicable to other recombinant toxins, has been described by Höfte et al., 1986.

In accordance with this invention, the binding of various ICPs to ICP receptors on the brush border membrane of the columnar midgut epithelial cells of various insect species has been investigated. The brush border membrane is the primary target of each ICP, and membrane vesicles, preferentially derived from the brush border membrane, can be obtained according to Wolfersberger et al., 1987.

The binding to ICP receptors of one or more ICPs (e.g., ICP A, ICP B, etc.) can be characterized by the following steps (Hofmann et al, 1988b):

1. ICP A is labelled with a suitable marker (usually a radioisotope such as $^{125}I$).
2. Brush border membranes are incubated with a small amount (preferably less than $10^{-10}M$) of labelled ICP A together with different concentrations of non-labelled ICP A (preferably from less than $10^{-11}$ to $10^{-5}M$).
3. For all concentrations tested the amount of labelled ICP A bound to the brush border membranes is measured.
4. Mathematical analysis of these data allows one to calculate various characteristics of the ICP receptor such as the magnitude of the population of binding sites (Scatchard, 1949).
5. Competition by other toxins (e.g. ICP B) is preferably studied by incubating the same amount of labelled ICP A with brush border membranes in combination with different amounts of ICP B (preferentially from $10^{-11}$ to $10^{-6}M$; and subsequently, steps 3 and 4 are repeated.

By this procedure, it has been found, for example, that Bt3 toxin, Bt2 toxin and Bt73 toxin are competitively binding anti-Lepidopteran ICPs for *Manduca sexta* and *Heliothis virescens* (See example 6 which follows). Various other combinations of toxins have been found to be non-competitively binding anti-Lepidopteran or anti-Coleopteran toxins (example 6).

Although the concept of competitivity versus non-competitivity of ICP binding does not have any practical importance by itself, the observation of the non-competitivity of two *B. thuringiensis* ICPs, active against the same target insect, can be put to very significant practical use. This is because a combination of two non-competitively binding *B. thuringiensis* ICPs can be used to prevent development, by a target insect, of resistance against such *B. thuringienis* ICPs.

A selection experiment with *M. sexta*, using Bt2 toxin, Bt18 toxin, and a mixture of Bt2 and Bt18 toxins, has shown that Bt2 and Bt18 are two non-competitively binding anti-Lepidopteran toxins. After 20 generations of selection, a very pronounced reduction in ICP sensitivity was observed in the selection experiments with Bt2 or Bt18 alone (>100 times). The reduction in sensitivity in the selection experiment with a Bt2–Bt18 mixture was only marginal (3 times). This demonstrates the unexpected practical advantage of a simultaneous use of two non-competitively binding ICPs in a situation which models the high selection pressure which will exist with the use of transgenic plants transformed with ICP genes. In this regard, the two resistant strains showed a specific loss in receptor sites for either the Bt2 or Bt18 toxin. In each case, receptor sites for the toxin, which was not used for selection, were not affected or their concentration even increased. Thus, the Bt2 selected strain retained its Bt18 receptors, and the Bt18 selected strain developed an increased number of Bt2 receptors. Indeed, the Bt18 selected strain showed an increased sensitivity for Bt2 along with its increased Bt2 receptor concentration. No significant changes in receptor sites were found in the strain selected against the combined toxins. These findings are described in detail in Example 7 which follows.

A similar mechanism of resistance to Bt has been observed with respect to a strain of diamondback moth, *Plutella xylostella*. This strain had developed resistance in the field to Dipel which is a commercial formulation of the Bt HD-1 strain. Crystals of Dipel comprise a mixture of several BtICPs, similar to the Bt2, Bt3 and Bt73 proteins which are competitively-binding ICPs. As shown by both insect bioassays and competitive binding studies using Bt2 and Bt15, the Dipel-resistant diamondback moth strain is resistant to Bt2 protoxin and toxin but maintains full sensitivity to Bt15 protoxin and toxin. This finding is relevant to other combinations of non-competitively binding anti-Lepidopteran or Coleopteran ICPs which are expected to have the same beneficial effect against their common target insects.

Hence, a combination of non-competitively binding ICPs, when directly expressed in a transgenic plant, offers the substantial advantage of reducing the chances of development of insect resistance against the ICPs expressed in the plant. There may be additional benefits because the combined spectrum of two toxins may be broader than the spectrum of a single ICP expressed in a plant (See Examples 8, 9 and 10 which follow).

If, among two competitively binding ICPs, one has a larger binding site population than the other against a given target insect, it will be most advantageous to use the one with the larger population of binding sites to control the target pest in combination with the most suitable non-competitively binding *B. thuringiensis* ICP. For example, as seen from Example 6, it is preferred to use Bt73 against *Heliothis virescens*, rather than Bt2 or Bt3, and it is preferred to use Bt3 against *Manduca sexta* rather than Bt2 or Bt73. The selected gene can then be combined with the best suitable non-competitively binding ICP.

Previously, plant transformations involved the introduction of a marker gene together with a single ICP gene, within the same plasmid, in the plant genome (e.g., Vaeck et al., 1987; Fischoff et al., 1987). Such chimeric ICP genes usually comprised either all or part of an ICP gene, preferably a truncated ICP gene fragment encoding the toxic core, fused to a selectable marker gene, such as the neo gene coding for neomycin phosphotransferase. The chimeric ICP gene was placed between the T-DNA border repeats for Agrobacterium Ti-plasmid mediated transformation (EP 0193259).

This invention involves the combined expression of two or even more *B. thuringiensis* ICP genes in transgenic plants. The insecticidally effective *B. thuringiensis* ICP genes, encoding two non-competitively binding ICPs for a target insect species, preferably encoding the respective truncated ICP genes, are inserted in a plant cell genome, preferably in its nuclear genome, so that the inserted genes are downstream of, and under the control of, a promoter which can direct the expression of the genes in the plant cell. This is preferably accomplished by inserting, in the plant cell genome, one or more chimaeric genes, each containing in the same transcriptional unit: at least one ICP gene; preferably a marker gene; and optionally a DNA sequence encoding a protease (e.g., trypsin)-sensitive or -cleavable protein part intercalated in frame between any two ICP genes in the chimaeric gene. Each chimaeric gene also contains at least one promoter which can direct expression of its ICP gene in the plant cell.

The selection of suitable promoters for the chimaeric genes of this invention is not critical. Preferred promoters for such chimaeric genes include: the strong constitutive 35S promoter obtained from the cauliflower mosaic virus, isolates CM 1841 (Gardner et al., 1981), CabbB-S (Franck et al., 1980) and CabbB-JI (Hull and Howell, 1987); the promoter of the nopaline synthetase gene ("PNOS") of the Ti-plasmid (Herrera-Estrella, 1983); the promoter of the octopine synthase gene ("POCS" [De Greve et al., 1982]); and the wound-inducible TR1' promoter and the TR2' promoter which drive the expression of the 1' and 2' genes, respectively, of the T-DNA (Velten et al., 1984). Alternatively, a promoter can be utilized which is specific for one or more tissues or organs of the plant, whereby the inserted genes are expressed only in cells of the specific tissue(s) or organ(s). Examples of such promoters are a stem-specific promoter such as the AdoMet-synthetase promoter (Peleman et al., 1989), a tuber-specific promoter (Rocha-Sosa et al., 1989), and a seed-specific promoter such as the 2S promoter (Krebbers et al., 1988). The ICP genes could also be selectively expressed in the leaves of a plant (e.g., potato) by placing the genes under the control of a light-inducible promoter such as the promoter of the ribulose-1,5-bisphosphate carboxylase small subunit gene of the plant itself or of another plant such as pea as disclosed in EP 0193259. Another alternative is to use a promoter whose expression is inducible (e.g., by temperature or chemical factors).

A 3' non-translated DNA sequence, which functions in plant cells for 3' end formation and the polyadenylation of the 3' end of the mRNA sequence encoded by the at least one ICP gene in the plant cell, also forms part of each such chimeric gene. The selection of a suitable 3' non-translated DNA sequence is not critical. Examples are the 3' untranslated end of the octopine synthase gene, the nopaline synthase gene or the T-DNA gene 7 (Velten and Schell, 1985).

The selection of marker genes for the chimaeric genes of this invention also is not critical, and any conventional DNA sequence can be used which encodes a protein or polypeptide which renders plant cells, expressing the DNA sequence, readily distinguishable from plant cells not expressing the DNA sequence (EP 0344029). The marker gene can be under the control of its own promoter and have its own 3' non-translated DNA sequence as disclosed above, provided the marker gene is in the same genetic locus as the ICP gene(s) which it identifies. The marker gene can be, for example: a herbicide resistance gene such as the sfr or sfrv genes (EPA 87400141); a gene encoding a modified target enzyme for a herbicide having a lower affinity for the herbicide than the natural (non-modified) target enzyme, such as a modified 5-EPSP as a target for glyphosate (U.S. Pat. No. 4,535,060; EP 0218571) or a modified glutamine synthetase as a target for a glutamine synthetase inhibitor (EP 0240972); or an antibiotic resistance gene, such as a neo gene (PCT publication WO 84/02913; EP 0193259).

Using *A. tumefaciens* Ti vector-mediated plant transformation methodology, all chimeric genes of this invention can be inserted into plant cell genomes after the chimaeric genes have been placed between the T-DNA border repeats of suitable disarmed Ti-plasmid vectors (Deblaere et al., 1988). This transformation can be carried out in a conventional manner, for example as described in EP 0116718, PCT publication WO 84/02913 and EPA 87400544.0. The chimeric genes can also be in non-specific plasmid vectors which can be used for direct gene transfer (e.g., as described by Pazkowski et al., 1984; De La Pena et al., 1986). Different conventional procedures can be followed to obtain a combined expression of two *B.thuringiensis* ICP genes in transgenic plants as summarized below.

I Chimeric gene constructs whereby two or more ICP genes and a marker gene are transferred to the plant genome as a single piece of DNA and lead to the insertion in a single locus in the genome Ia The genes can be engineered in different transcriptional units each under control of a distinct promoter To express two or more ICP genes and a marker gene as separate transcriptional units, several promoter fragments directing expression in plant cells can be used as described above. All combinations of the promoters mentioned above in the chimaeric constructs for one ICP gene are possible. Examples of such individual chimeric constructs are described for the bt2 gene in EP 0193259, for the bt13 gene in EPA 88402115.5 and for the bt18 gene in EPA 88402241.9. The ICP gene in each chimeric gene of this invention can be the intact ICP gene or preferably an insecticidally-effective part of the intact ICP gene, especially a truncated gene fragment encoding the toxic core of the ICP. The individual chimeric genes are cloned in the same plasmid vector according to standard procedures (e.g., EP 0193259).

Ib Two genes (e.g., either an ICP and a marker gene or two ICP genes) or more can be combined in the same transcriptional unit To express two or more ICP genes in the same transcriptional unit, the following cases can be distinguished:

In a first case, hybrid genes in which the coding region of one gene is in frame fused with the coding region of another gene can be placed under the control of a single promoter. Fusions can be made between either an ICP and a marker gene or between two ICP genes. An example of an ICP gene-marker gene fusion has been described in EP 0193259 (i.e., a hybrid truncated bt2-neo gene encoding a Bt2 toxin-NPTII fusion protein).

Another possibility is the fusion of two ICP genes. Between each gene encoding an ICP which still is insecticidally active (i.e., a toxic part of the protoxin), a gene fragment encoding a protease (e.g., trypsin)—sensitive protein part should be included, such as a gene fragment encoding a part of the N-terminal or C-terminal amino acid sequence of one of the ICPs which is removed or cleaved upon activation by the midgut enzymes of the target insect species.

In a second case, the coding regions of the two respective ICP genes can be combined in dicistronic units placed under the control of a promoter. The coding regions of the two ICP genes are placed after each other with an intergenic sequence of defined length. A single messenger RNA molecule is generated, leading to the translation into two separate gene products. Based on a modified scanning model (Kozak, 1987), the concept of reinitiation of translation has been accepted provided that a termination codon in frame with the upstream ATG precedes the downstream ATG. Experimental data also demonstrated that the plant translational machinery is able to synthesize several polypeptides from a polycistronic mRNA (Angenon et al., 1989).

II Chimeric constructs with one or more ICP genes that are transferred to the genome of a plant already transformed with a one or more ICP genes Several genes can be introduced into a plant cell during sequential transformation steps (retransformation), provided that an alternative system to select transformants is available for the second round of transformation. This retransformation leads to the combined expression of ICP genes which are introduced at multiple loci in the genome. Preferably, two different selectable marker genes are used in the two consecutive transformation steps. The first marker is used for selection of transformed cells in the first transformation, while the second marker is used for selection of transformants in the second round of transformation. Sequential transformation steps using kanamycin and hygromycin have been described, for example by Sandler et al. (1988) and Delauney et al. (1988).

III Chimeric constructs with one or more ICP genes, that are separately transferred to the nuclear genome of separate plants in independent transformation events and are subsequently combined in a single plant genome through crosses.

The first plant should be a plant transformed with a first ICP gene or an F1 plant derived herefrom through selfing (preferably an F1 plant which is homozygous for the ICP gene). The second plant should be a plant transformed with a second ICP gene or an F1 plant derived herefrom through selfing (preferably an F1 plant which is homozygous for the second ICP gene). Selection methods can be applied to the plants obtained from this cross in order to select those plants having the two ICP genes present in their genome (e.g., Southern blotting) and expressing the two ICPs (e.g., separate ELISA detection of the immunologically different ICPs). This is a useful strategy to produce hybrid varieties from two parental lines, each transformed with a different ICP gene, as well as to produce inbred lines containing two different ICP genes through crossing of two independent transformants (or their F1 selfed offspring) from the same inbred line.

IV Chimeric constructs with one or more ICP genes separately transferred to the genome of a single plant in the same transformation experiment leading to the insertion of the respective chimeric genes at multiple loci.

Cotransformation involves the simultaneous transformation of a plant with two different expression vectors, one containing a first ICP gene, the second containing a second ICP gene. Along with each ICP gene, a different marker gene can be used, and selection can be made with the two markers simultaneously. Alternatively, a single marker can be used, and a sufficiently large number of selected plants can be screened in order to find those plants having the two ICP genes (e.g., by Southern blotting) and expressing the two proteins (e.g., by means of ELISA). Cotransformation with more than one T-DNA can be accomplished by using simultaneously two different strains of Agrobacterium, each with a different Ti-plasmid (Depicker et al., 1985) or with one strain of Agrobacterium containing two T-DNAs on separate plasmids (de Framond et al., 1986). Direct gene transfer, using a mixture of two plasmids, can also be employed to cotransform plant cells with a selectable and a non-selectable gene (Schocher et al., 1986).

The transgenic plant obtained can be used in further plant breeding schemes. The transformed plant can be selfed to obtain a plant which is homozygous for the inserted genes. If the plant is an inbred line, this homozygous plant can be used to produce seeds directly or as a parental line for a hybrid variety. The gene can also be crossed into open pollinated populations or other inbred lines of the same plant using conventional plant breeding approaches.

Of course other plant transformation methods can be used and are within the scope of the invention as long as they result is a plant which expresses two or more non-competitively binding ICPs. In this regard, this invention is not limited to the use of Agrobacterium Ti-plasmids for transforming plant cells with genes encoding non-competitively binding ICPs. Other known methods for plant cell transformations, such as electroporation or by the use of a vector system based on plant viruses or pollen, can be used for transforming monocotyledonous and dicotyledonous plants in order to obtain plants which express two non-competitively binding ICPs. Furthermore, DNA sequences encoding two non-competitively binding ICPs other than those disclosed herein can be used for transforming plants. Also, each of the ICP genes, described herein, can be encoded by equivalent DNA sequences, taking into consideration the degeneracy of the genetic code. Also, equivalent ICPs with only a few amino acids changed, such as would be obtained through mutations in the ICP gene, can also be used, provided they encode a protein with essentially the same characteristics (e.g., insecticidal activity and receptor binding).

The following Examples illustrate the invention. Those skilled in the art will, however, recognize that other combinations of two or more non-competitively binding *B. thuringiensis* ICP genes can be used to transform plants in accordance with this invention in order to prevent the development, in a target insect, of resistance to *B. thuringiensis* ICPs expressed in the transformed plants. Unless otherwise indicated, all procedures for making and manipulating DNA were carried out by the standardized procedures described in Maniatis et al, *Molecular Cloning—A Laboratory Manual*, Cold Spring Harbor Laboratory (1982).

EXAMPLE 1

Collection of genes

The collection of anti-Lepidopteran and anti-Coleopteran Bt genes encoding ICPs, which are the subject of the Examples, is described in Table 2 (following the Examples). References for the respective genes are indicated in Table 2. The origin, the isolation and characterization of the Bt genes, which have not been published, are described below. Bt strains, such as strains HD-1, HD-68, HD-110, and HD-73, are publicly available from the Agricultural Research Culture Collection, Northern Regional Research Laboratory, U.S. Dept. of Agriculture, Peoria, Ill. 61604, U.S.A.

bt3 gene: From *B. thuringiensis* var. kurstaki HD-1, the ICP was cloned. Characterization of this gene revealed an open reading frame of 3528 bp which encodes a protoxin of 133 kDa. This gene was identical to the one described by Schnepf et al. (1985).

bt73 gene: From *B. thuringiensis* var HD-73. The ICP gene was cloned as described by Adang et al. (1985).

bt4 gene: A genomic library was prepared from total DNA of strain *B. thuringiensis* aizawai HD-68. Using the 1.1 kb internal HindIII fragment of the bt2 gene as a probe, a gene designated bt4 was isolated. Characterization of this gene revealed an open reading frame of 3495 bp which encodes a protoxin of 132 kDa and a trypsin activated toxin fragment of 60 kDa. This (insect controlling protein) gene differs from previously identified genes and was also found in several other strains of subspecies aizawai and entomocidus including HD-110. FIG. 13 shows the nucleotide sequence and deduced amino acid sequence of the open reading frame ("ORF") of the bt4 gene extending from nucleotide 264 to nucleotide 3761.

bt14 and bt15 genes: A genomic library was prepared from total DNA of strain *B. thuringiensis* var. entomocidus HD-110 by partial Sau3A digest of the total DNA and cloning in the vector pEcoR251 (deposited at DSM under accession number 4711). Using monoclonal antibodies (Höfte et al., 1988), at least three structurally distinct ICPs were identified in crystals of *B. thuringiensis* entomocidus HD-110. These monoclonal antibodies were used to clone the three different ICP genes from this *B. thuringiensis* strain. One of these genes is the bt4 gene as described above. The second gene was called "bt15". FIG. 14 shows the nucleotide sequence and deduced amino acid sequence of the ORF of the bt15 gene, isolated from HD-110, extending from nucleotide 234 to nucleotide 3803. The Shine and Dalgarno sequence, preceding the initiation codon is underlined. This gene has an open reading frame of 3567 bp which encodes a protoxin of 135 kDa and a 63 kDa toxin fragment. A similar gene has been described by Honee et al. 1988, isolated from *B. thuringiensis entomocidus* 60.5. The bt15 gene differs from the published sequence at three positions: an Ala codon (GCA) is present instead of an Arg codon (CGA) at position 925 and a consecution of a Thr-His codon (ACGCAT) is present instead of a Thr-Asp codon (ACCGAT) at position 1400. (The numbers of the positions are according to Honnee et al., 1988). Another similar gene has been described in EP 0295156, isolated from *B. thuringiensis aizawai* 7-29 and entomocidus 6-01. The bt15 gene is different from this published nucleotide sequence at three different places: 1) a Glu codon (GAA) instead of an Ala codon (GCA) at position 700; 2) the sequence TGG, CCA, GCG, CCA instead of TGC, CAG, CGC, CAC, CAT at position 1456 and 3) an Arg codon (CGT) instead of an Ala codon (GCG) at position 2654. (The numbers of the positions are according to EP 0295156).

The third gene isolated was called "bt14". It has an open reading frame of 3621 bp which encodes a 137 kDa protoxin and a 66 kDa activated toxin fragment. A similar gene has been cloned from *B.thuringiensis* HD-2 (Brizzard and Whiteley, 1988). The bt14 gene differs from the published nucleotide sequence by two nucleotide substitutions: a T instead of a C at position 126, and a C instead of a T at position 448 (the numbers of the positions are according to Brizzard and Whiteley, 1988). In the first case, the Ile codon (ATT or ATC) is conserved whereas in the second case the Tyr codon (TAT) is converted to a His codon (CAC).

bt2 gene: The bt2 gene was cloned as described in EP 0193259.

bt18 gene: Cloning of the bt18 gene was performed as described in EPA 88402241.9.

bt13 gene: The bt13 gene was cloned as described in EPA 88402115.5.

bt21 and bt22 genes: These genes, encoding Coleopteran-active ICPs, were cloned as described in EPA 89400428.2.

EXAMPLE 2

Construction of gene cassettes and expression of Bt genes in *E.coli*

1) bt2, bt18: the construction of bt2 and bt18 gene cassettes has been previously described in EPA 86300291.1 and 88402241.9, respectively. Basically, they comprise a truncated gene encoding the toxic core and a hybrid gene comprising the truncated gene fused in frame to the N-terminus of the neo gene. The gene cassettes are used to transform *E. coli* to express the Bt2 and Bt18 ICP toxins.
2) bt14, bt15: as described in EPA 88402241.9, gene cassettes for the bt14 and bt15 genes were constructed in order to express the genes in *E.coli* and in plants.

First, a NcoI site was introduced at the N-terminus of the genes by site-directed mutagenesis.

In the case of the bt15 gene, the conversion of the TT nucleotides, immediately in front of the ATG codon, into CC yielded a NcoI site overlapping with the ATG initiation codon. This site was introduced using the pMa/c vectors for site-directed mutagenesis (Stanssens et al., 1987) and a 28-mer oligonucleotide with the following sequence (SEQ ID NO:1): 5'-CGGAGGTATTCCATGGAGGAAAATAATC-3'. This yielded the plasmid pVE29 carrying the N-terminal fragment of the bt15 gene with a NcoI site at the ATG initiation codon.

According to Brizzard and Whiteley (1988), the initiation codon of the bt14 gene is a TTG codon. Thus, a NcoI site was created in a like manner at this codon for site directed mutagenesis using a 34-mer oligonucleotide with the following sequence (SEQ ID NO:2) 5'-CCTATTTGAAGCCATGGTAACTCCTCCTTTTATG-3'. In this case the sequence of the intitiation codon was converted from ATATTGA to ACCATGG. This yielded the plasmid pHW44 carrying the N-terminal fragment of the bt14 gene with a NcoI site at the initiation codon.

In a second step, the genes were reconstructed by ligating the N-terminal gene fragments with a suitable C-terminal gene fragment, yielding a bt15 gene and bt14 gene with a NcoI site at the ATG initiation codon.

To express the bt14 and bt15 genes encoding the protoxin in *E. coli*, the following constructs were made: pOH50 containing the bt15 gene under the control of the lac promoter; and pHW67 containing the bt14 gene under the control of the tac promoter. Induction of a culture of the *E. coli* strain WK6 carrying the respective plasmids with IPTG yielded an overproduced protein (Fuller, 1982).

The active toxic fragments of the Bt15 and Bt14 protoxins comprise 63 and 60 kDa trypsin digest products respectively. Instead of expressing the whole bt15 or bt14 gene, it is also possible to express a toxin-encoding gene fragment or derivative thereof in plants. To this end, truncated bt14 and bt15 gene fragments were constructed. In order to be able to select transgenic plants producing the ICP gene products, hybrid genes of the truncated gene fragments were also made with the neo gene encoding a selectable marker as described in EP 0193259.

By comparison of the nucleotide sequence of the bt4, bt14 and bt15 genes, respectively, with the bt2 and bt18 genes, respectively, the BclI site could be identified as a suitable site localized downstream of the coding sequence encoding the toxin gene fragment. To construct a truncated gene fragment and a hybrid gene of the truncated gene fragment with the neo gene, the filled BclI site was ligated to the filled EcoRI site of pLKM91 (Höfte et al., 1986) and the filled HindIII site of pLK94 respectively (Botterman and Zabeau, 1987). pLKM91 carries a 5' truncated neo gene fragment which codes for an enzymatically active C-terminal gene fragment of the neo gene, and pLK94 contains translation stop codons in three reading frames. This yielded the following plasmids which are then used to transform *E. coli* to express the ICP genes: pHW71 carrying a truncated bt14-neo hybrid gene; pHW72 carrying a truncated bt14 gene; pVE34 carrying a truncated bt15-neo hybrid gene; and pVE35 carrying a truncated bt15 gene.

In a similar way as described for the bt14 and bt15 genes, gene cassettes are constructed for the bt3 and bt4 genes which are then expressed in *E.coli.*

EXAMPLE 3

Purification of recombinant ICPs

The ICPs expressed in *E. coli* in Example 2 are purified by the method (described for recombinant Bt2 protoxin) by Höfte et al. (1986).

EXAMPLE 4

Purification of toxins

Solubilized protoxins of Bt2, Bt3, Bt73, Bt4, Bt14, Bt15, Bt18, Bt13, Bt21and Bt22 (in $Na_2CO_3$ 50 mM, DTT 10 mM pH=10) are dialyzed against 0.5% $(NH_4)_2CO_3$ at pH 8 and treated with trypsin (trypsin/protoxin=1/20 w/w) for 2 h at 37° C. The activated toxin is chromatographically purified (Mono-Q column on FPLC) as described by Hofmann et al.(1988b).

EXAMPLE 5

Determination of the insecticidal spectrum

The ICP protoxins and toxins of Examples 3 and 4 are evaluated for their insecticidal activity. Each protoxin is dissolved in alkaline buffer containing a reducing agent ($Na_2CO_3$ 50 mM, DTT 10 mM pH=10), and each toxin is used as soluble protein directly from FPLC. Protein concentrations are determined. Subsequently, dilutions of the resulting protoxin or toxin solution are prepared in PBS buffer pH=7.4 containing 0.15M NaCl and 0.1% bovine serum albumin ("BSA").

The artificial medium for insect culture, described by Bell and Joachim (1976) for *Manduca sexta*, is poured in appropriate receptacles and allowed to solidify. Subsequently a quantity of the (pro)toxin dilutions is applied on this medium, and the water is allowed to evaporate under a laminar flow. This results in a medium with a certain quantity (in the range of 0.1 to 10000 ng/cm2) of toxin coated on its surface. For example, for the Bt2 toxin, typical dilutions for a toxicity test on *Manduca sexta* are 1, 5, 25, 125 and 625 ng/cm2. First instar larvae of *Manduca sexta* are then applied on the coated medium, and growth and mortality are assessed after 6 days. Mortality increases with dosage. Dose response data is analysed in probit analysis (Finney, 1962), and the data are best summarized by an $LD_{50}$ value which is the amount of toxin which kills 50% of the insects. The $LD_{50}$ for Bt2 toxin against *Manduca sexta* is around 20 ng/cm2.

Similar assays are carried out for other insect species using a suitable diet or by applying the ICPs on leaves for insects, for which no artificial diet is used.

EXAMPLE 6

Binding studies

Toxins

All protoxins and their toxic fragments were purified according to the methods described for the Bt2 protoxin and toxin in Höfte et al. (1986) and EP 0193259. The activated and purified toxins are further referred to as the Bt2, Bt3, Bt73, Bt4, Bt14, Bt15, Bt18, Bt13, Bt21 and Bt22 toxins.

By way of example for the Bt73 toxin, it has been shown that *B. thuringiensis* var. kurstaki HD73 produces a protein of 133 kDa encoded by a 6.6 kb type gene. A culture of this strain was grown as described by Mahillon and Delcour (1984). The autolysed culture was spun down (20 minutes at 4500 rpm in a HB4 rotor) and washed with a buffer containing 20 mM Tris, 100 mM NaCl and 0.05% Triton X-100, pH 8. The final pellet was resuspended in this buffer (4 ml buffer for 100 ml culture). This solution was then layered onto a linear Urograffin gradient (60–70%) which was centrifuged in a SW 28 rotor for 90 minutes at 18000 rpm. Crystals were collected and stored at −20° C. until further use. Activation was performed according to Höfte et al. (1986). The purified toxin is further referred to as the Bt73 toxin.

Iodination of ICPs

Iodination of Bt2, Bt3, and Bt73 toxins was performed using the Chloramin-T method (Hunter and Greenwood, 1962). 1 mCi $^{125}$I-NaI and 20 to 37.5 ug Chloramin-T in NaCl/$P_i$ were added to 50 ug of purified toxin. After gentle shaking for 60 seconds, the reaction was stopped by adding 53 ug of potassium metabisulfite in $H_2O$. The whole mixture was loaded on a PD 10 Sephadex G-25M gelfiltration column to remove free iodine. A subsequent run on a Biogel P-60 column was carried out in order to increase the purity.

Alternatively, toxins were labeled using the Iodogen method. Iodogen (Pierce) was dissolved in chloroform at 0.1 mg/ml. 100 ul of this solution was pipetted into a disposable glass vessel and dried under a stream of nitrogen gas. The vessel was rinsed with Tris buffer (20 mM Tris, pH 8.65 with 0.15M NaCl). 50 ug of toxin (in Tris buffer) was incubated with 1 mCi of $^{125}$I-NaI in the tube for 10 minutes. The reaction was then stopped by the addition of 1M NaI (one fourth of the sample volume). The sample was immediately loaded onto a PD10 Sephadex G-25M column and later on a Biogel P-60 column to remove free iodine and possible degradation products.

Other toxins were iodinated using one of the above mentioned procedures.

Determination of specific activity of iodinated toxin

Specific activity of iodinated Bt2, Bt3, and Bt73 toxin samples was determined using a "sandwich" ELISA technique according to Voller, Bidwell and Barlett (1976). Primary antibody was a polyclonal antiserum raised against Bt2 toxin, and the secondary antibody was a monoclonal antibody 4D6.

The conjugate used was alkaline phosphatase coupled to anti-mouse IgG. The reaction intensity of a standard dilution series of unlabeled toxin and dilutions of the iodinated toxin sample (in NaCl/$P_i$-0.1% BSA) was measured. Linear regression calculations yielded the protein content of the radioactive toxin sample. The samples with the highest specific activities were used in the binding assays. Specific activities were 59400, 33000 and 19800 Ci/mole (on reference date) for Bt73 toxin (labeled according to lodogen procedure), Bt2 toxin (Chloramin-T method) and Bt3 toxin (Iodogen method) respectively.

Specific activities of other toxins were determined using a similar approach. Specific monoclonal and polyclonal antibodies for each of these toxins were raised and applied in ELISA.

Preparation of brush border membrane vesicles

Brush border membrane vesicles ("BBMV") from *Manduca sexta, Heliothis virescens, Plutella xylostella, Phthorimaea operculella, Spodoptera exigua, Spodoptera littoralis, Plodia interpunctella, Mamestra brassicae, Pieris brassicae* and *Leptinotarsa decemlineata* were prepared according to the method of Wolfersberger et al. (1987). This is a differential centrifugation method that makes use of the higher density of negative electrostatic charges on luminal than on basolateral membranes to separate these fractions.

Binding assay

Duplicate samples of $^{125}$I-labeled toxin, either alone or in combination with varying amounts of unlabeled toxin, were incubated at the appropriate temperature with brush border membrane vesicles in a total volume of 100 ul of Tris buffer (Tris 10 mM, 150 mM NaCl, pH 7.4). All buffers contained 0.1% BSA. The incubation temperature was 20° C. Ultrafiltration through Whatman GF/F glass fiber filters was used to separate bound from free toxin. Each filter was rapidly washed with 5 ml of ice-cold buffer (NaCl/$P_i$-0.1% BSA). The radioactivity of the filter was measured in a gamma-counter (1275 Minigamma, LKB). Binding data were analyzed using the LIGAND computer program. This program calculates the bound concentration of ligand as a function of the total concentration of ligand, given the affinity (Ka or its inverse Kd=1/Ka, the dissociation constant) and the total concentration of receptors or binding site concentration ($R_t$).

Determination of protein concentration

Protein concentrations of purified Bt2, Bt3, Bt73 and Bt15 toxins were calculated from the OD at 280 nm (measured with a Uvikon 810 P, Kontron Instruments spectrofotometer). The protein content of solutions of other toxins and of brush border membrane vesicles (BBMV) as measured according to Bradford (1976).

Binding of Bt2, Bt3 and Bt73 toxins to BBMV of *Manduca sexta* and *Heliothis virescens*: an example of 3 competitively binding Lepidopteran ICPs.

Bt2, Bt3 and Bt73 toxins are toxic to both *Manduca sexta* and *Heliothis virescens*: LC50 values for *Manduca sexta* are respectively 17.70, 20.20 and 9.00 ng/cm2; for *Heliothis virescens* the LC50's are 7.16, 90.00 and 1.60 ng/cm2.

Labelled toxin, either Bt3 (0.8 nM) or Bt2 (1.05 nM) or Bt73 (1.05 nM), was incubated with BBMV in a volume of 0.1 ml. BBMV protein concentrations were 100 ug/ml for *M. sexta* and for Bt2-*H. virescens*, for Bt3-*H. virescens* 150 and for Bt73-*H. virescens* 50 ug/ml. The labelled toxin was combined with varying amounts of an unlabeled toxin (competitor). After a 30 min. incubation, bound and free toxins were separated through filtration.

FIGS. 1–3 show the percentages binding of respectively labelled Bt2, Bt3 and Bt73 toxins as a function of the concentration of competitor for *Manduca sexta*. FIGS. 4–6 show these data for *Heliothis virescens*. The amount bound in the absence of competitor is always taken as 100% binding. FIGS. 1–6 show the binding of $^{125}$I-labeled toxins to *M. sexta* (in FIGS. 1, 2 and 3) and *H. virescens* (in FIGS. 4, 5 and 6) brush border membrane vesicles. Vesicles were incubated with labeled toxin [in FIGS. 1 and 4: $^{125}$I-Bt2- toxin (1.05 nM); in FIGS. 2 and 5: $^{125}$I-Bt3-toxin (0.8 nM); in FIGS. 3 and 6: $^{125}$I-Bt73-toxin (1.05 nM)] in the presence of increasing concentrations of Bt2 toxin (★), Bt3 toxin (●) or Bt73 toxin (▲). Binding is expressed as percentage of the amount bound upon incubation with labeled toxin alone. On M. sexta vesicles, these amounts were 1820, 601 and 2383 cpm, and on H. virescens vesicles 1775, 472 and 6608 cpm for $^{125}$I-Bt2-, Bt3- and Bt73-toxin, respectively. Non-specific binding was not substracted. Data were analyzed with the LIGAND computer program. Each point is the mean of a duplicate sample.

FIG. 1: shows the binding of $^{125}$I Bt2 toxin to M. sexta BBMV

Figure 2:
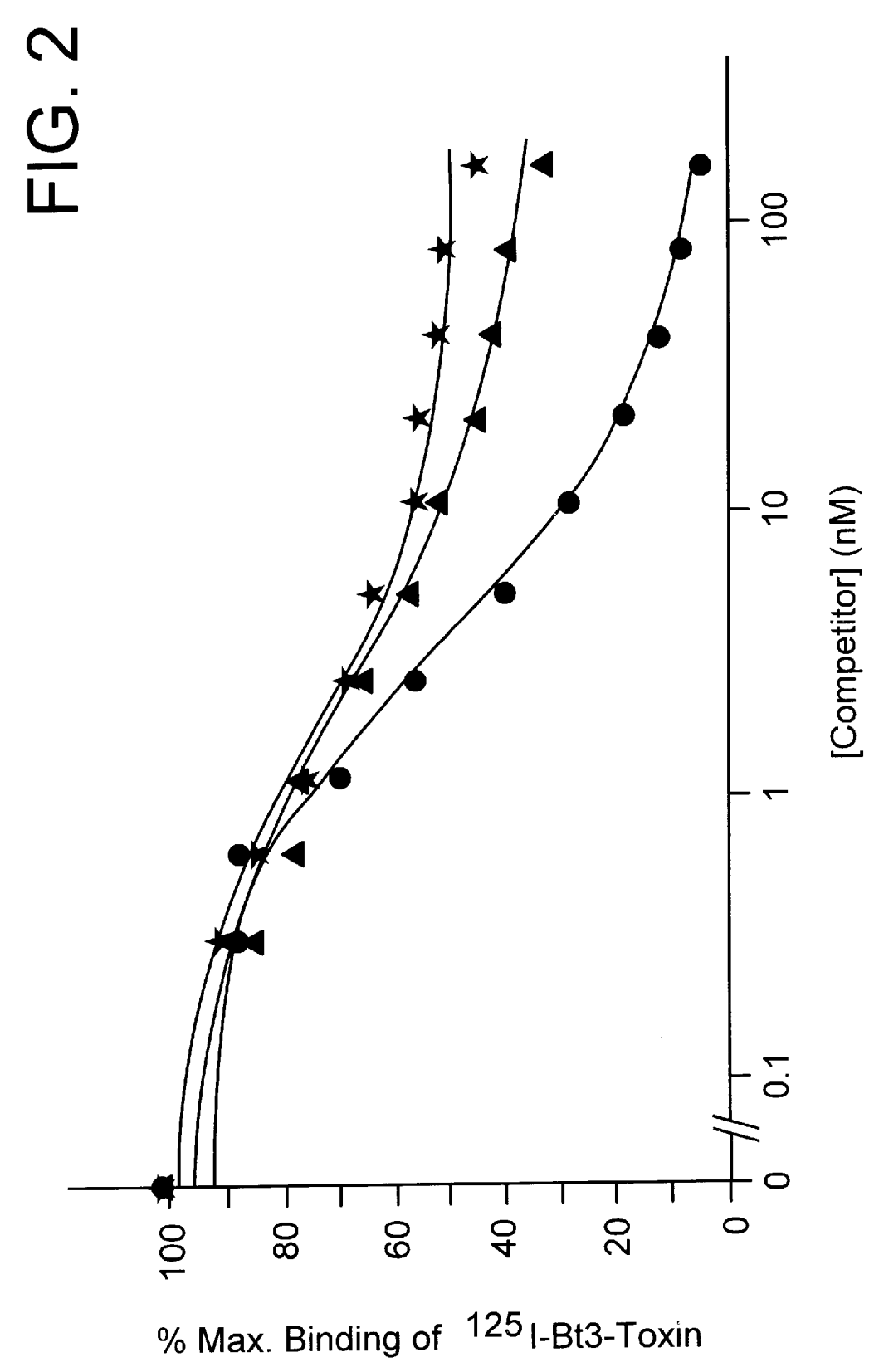

FIG. 2: shows the binding of $^{125}$I Bt3 toxin to M. sexta BBMV

Figure 3:
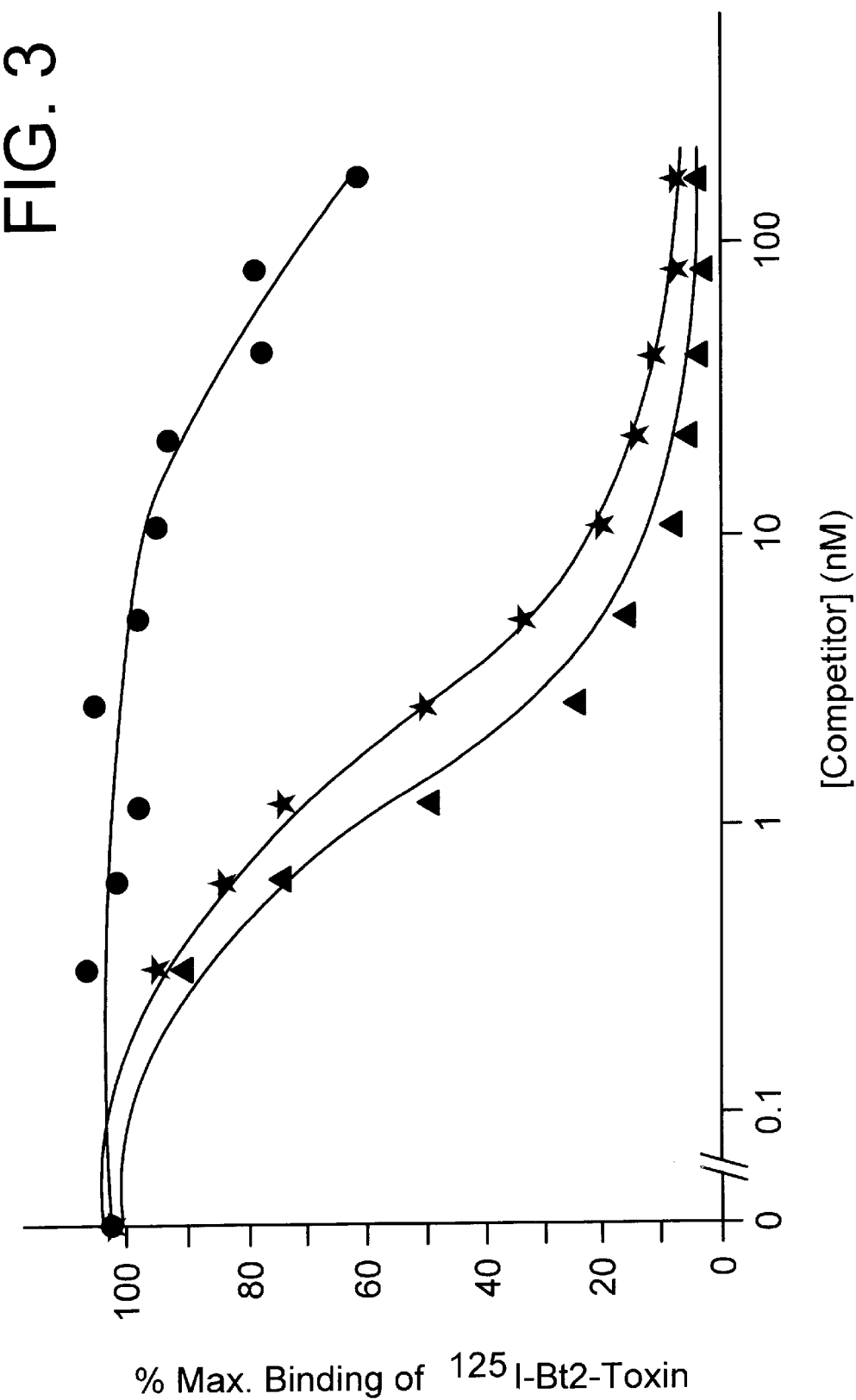
FIG. 3 is a graph showing the binding of $^{125}$I-labeled Bt73 toxin to M. sexta BBMV in the presence of increasing concentrations of Bt2 toxin (★), Bt3 toxin (●) or Bt73 toxin (▲).

FIG. 3: shows the binding of $^{125}$I Bt73 toxin to M. sexta BBMV

Figure 4:
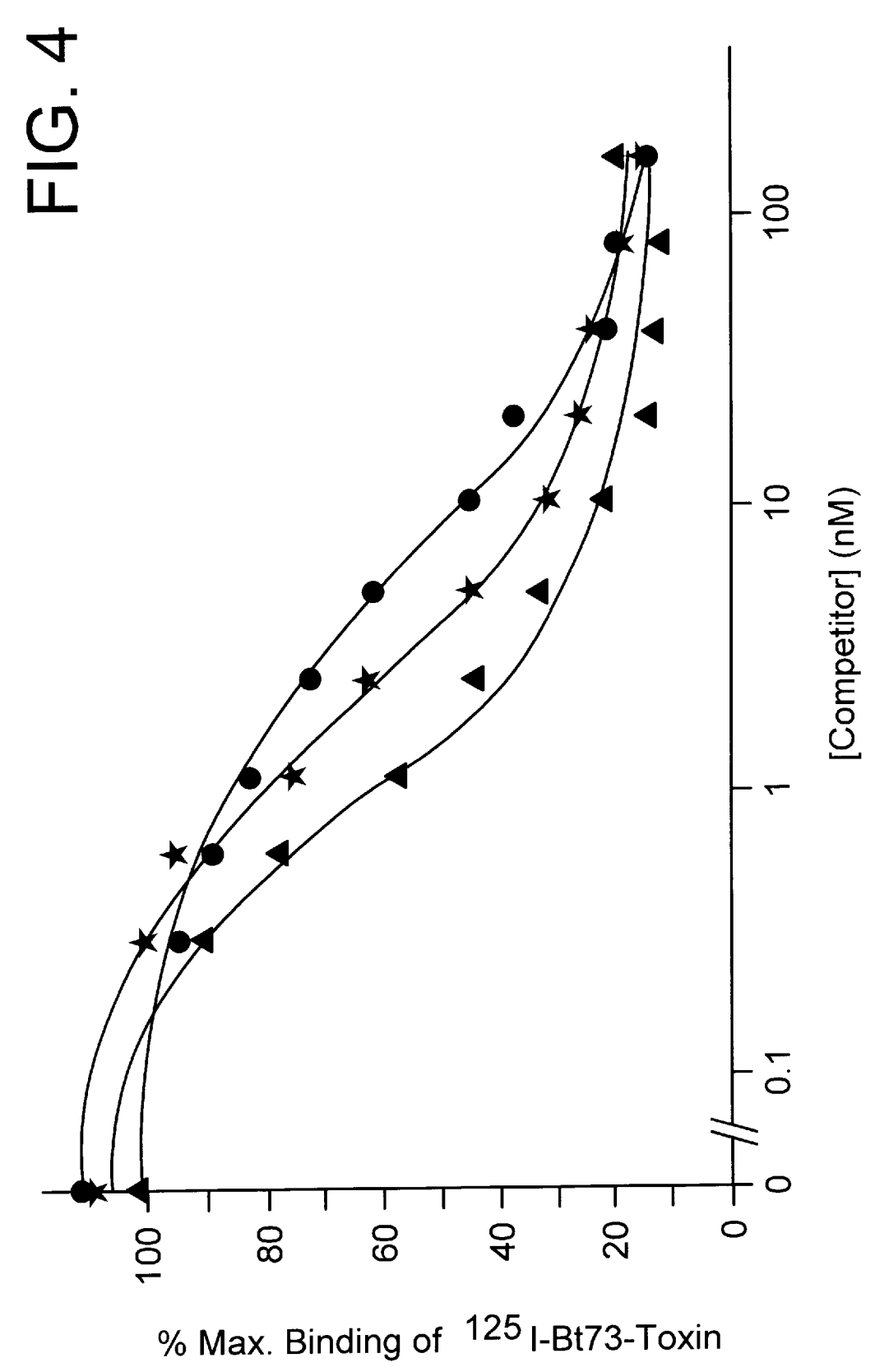

FIG. 4: shows the binding of $^{125}$I Bt2 toxin to H. virescens BBMV

Figure 5:
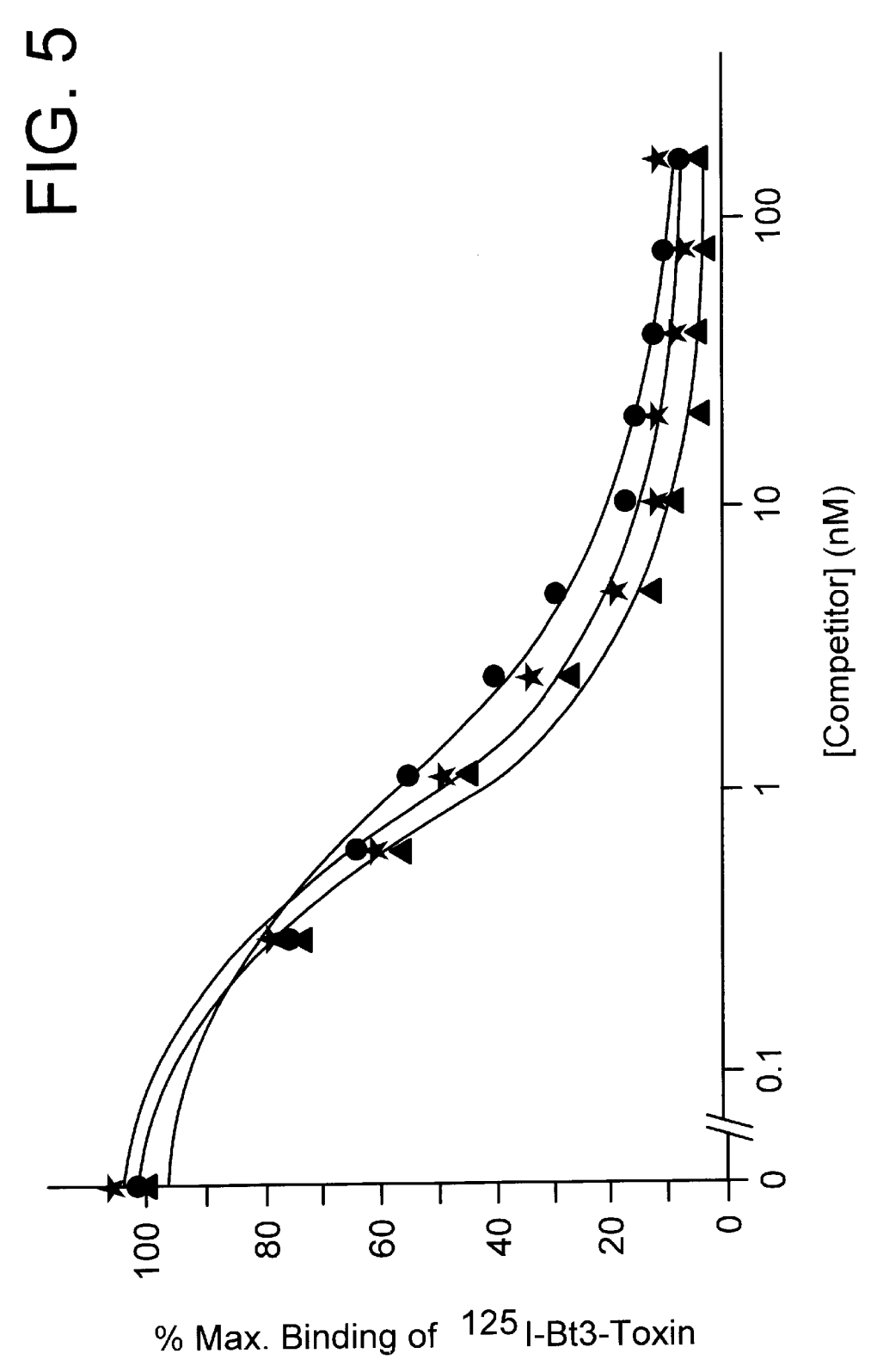

FIG. 5: shows the binding of $^{125}$I Bt3 toxin to H.virescens BBMV

Figure 6:
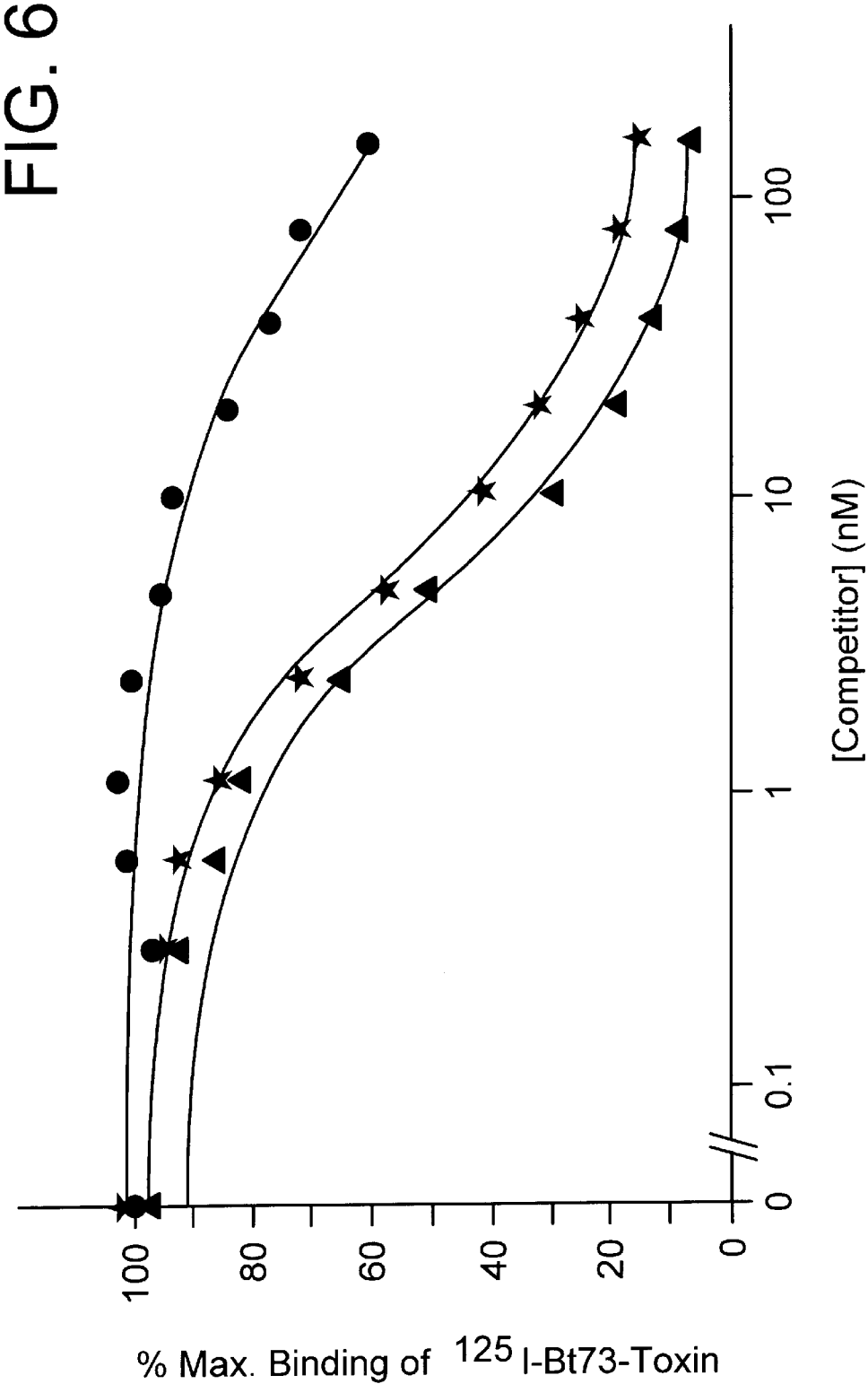
FIG. 6 is a graph showing the binding of $^{125}$I-labeled Bt73 toxin to H. virescens BBMV in the presence of increasing concentrations of Bt2 toxin (★), Bt3 toxin (●) or Bt73 toxin (▲).

FIG. 6: shows the binding of $^{125}$I Bt73 toxin to H.virescens BBMV

The conclusions from FIGS. 1–6 are that Bt2 and Bt3, Bt3 and Bt73, and Bt2 and Bt73 are competitively-binding ICP's both for *Manduca sexta* and for *Heliothis virescens*. Indeed Bt3 competes for the entire population of receptor sites of Bt2 in *Manduca sexta* (FIG. 1): the % labelled Bt2 bound in the presence of 100 nM Bt3 is equal to the % Bt2 bound with 100 nM of Bt2 itself. The opposite is not true: in the presence of 100 nM Bt2 the % of labelled Bt3 is not reduced to the same level as with 100 nM of Bt3 (FIG. 2).

A similar reasoning is followed to observe competitivity of other toxin combinations: Bt3 competes for the entire population of receptor sites of Bt73 (FIG. 3) in *M. sexta*; the opposite is not true (FIG. 2); Bt2 and Bt73 compete for the entire population of each other's binding sites in *M. sexta* (FIGS. 1 and 3).

In *Heliothis virescens*: Bt2 competes for the entire population of receptor sites of Bt3 (FIG. 5); Bt73 competes for the entire population of receptor sites of Bt3 (FIG. 5); Bt73 competes for the entire population of receptor sites of Bt2 (FIG. 4); but the opposite statements are not true (FIGS. 4, 5 and 6).

The same data can be used in mathematical analysis (e.g., Scatchard analysis according to Scatchard, 1949; analysis with the LIGAND computer program according to Munson and Rodbard, 1980) to calculate the dissociation constant (Kd) of the toxin-receptor complex and the concentration of binding sites (Rt); the results of these calculations using the LIGAND computer program were the following:

Bt2-*M.sexta*: Kd=0.4 nM Rt=3.4 pmol/mg vesicle protein
Bt3-*M. sexta*: Kd=1.5 nM Rt=9.8 pmol/mg vesicle protein
Bt73-*M. sexta*: Kd=0.6 nM Rt=4.0 pmol/mg vesicle protein
Bt2-*H. virescens*: Kd=0.6 nM Rt=9.7 pmol/mg vesicle protein
Bt3-*H. virescens*: Kd=1.2 nM Rt=3.7 pmol/mg vesicle protein
Bt73-*H. virescens*: Kd=0.8 nM Rt=19.5 pmol/mg vesicle protein These data demonstrate the high affinity receptor binding of the toxins (Kds in the range of $10^{-10}$ to $10^{-9}$ M.

Binding of Bt2 and Bt14 toxins to BBMV of *P. brassicae*, *Plutella xylostella* and *Phthorimaea opercullella*: an example two non-competitively binding Lepidopteran ICPs Bt2 and Bt14 toxins are toxic to *P. brassicae* (p.b.), *P. xylostella* (p.x.) and *P. operculella* (p.o.) as seen from the table below.

|      | $LC_{50}$ of Toxins | |
|------|------|------|
|      | Bt2  | Bt14 |
| P.b. | 1.3  | 2.0  |
| P.x. | 6.7  | 5.4  |
| P.o. | 4.20 | 0.8–4.0 |

$LC_{50}$ values of solubilized purified Bt2 and Bt14 toxins for P.x. are expressed as ng protein spotted per $cm^2$ of artificial diet. $LC_{50}$ values for P.b. are expressed as $ug^2$ toxin per ml solution into which leaf discs, fed to first instar Pb larvae, were dipped. For P.o., $LC_{50}$ values are expressed in ug/ml into which potato chips were dipped prior to feeding.

Labelled Bt2 toxin (1.05 nM) or Bt14 toxin (1.4 nM) was incubated with BBMV from *P. brassicae* (100 ug protein/ml) in a volume of 0.1 ml in combination with varying amounts of unlabelled Bt2 or Bt14. After a 30 min. incubation period at 22° C., the bound and free toxins were separated.

Figure 7:
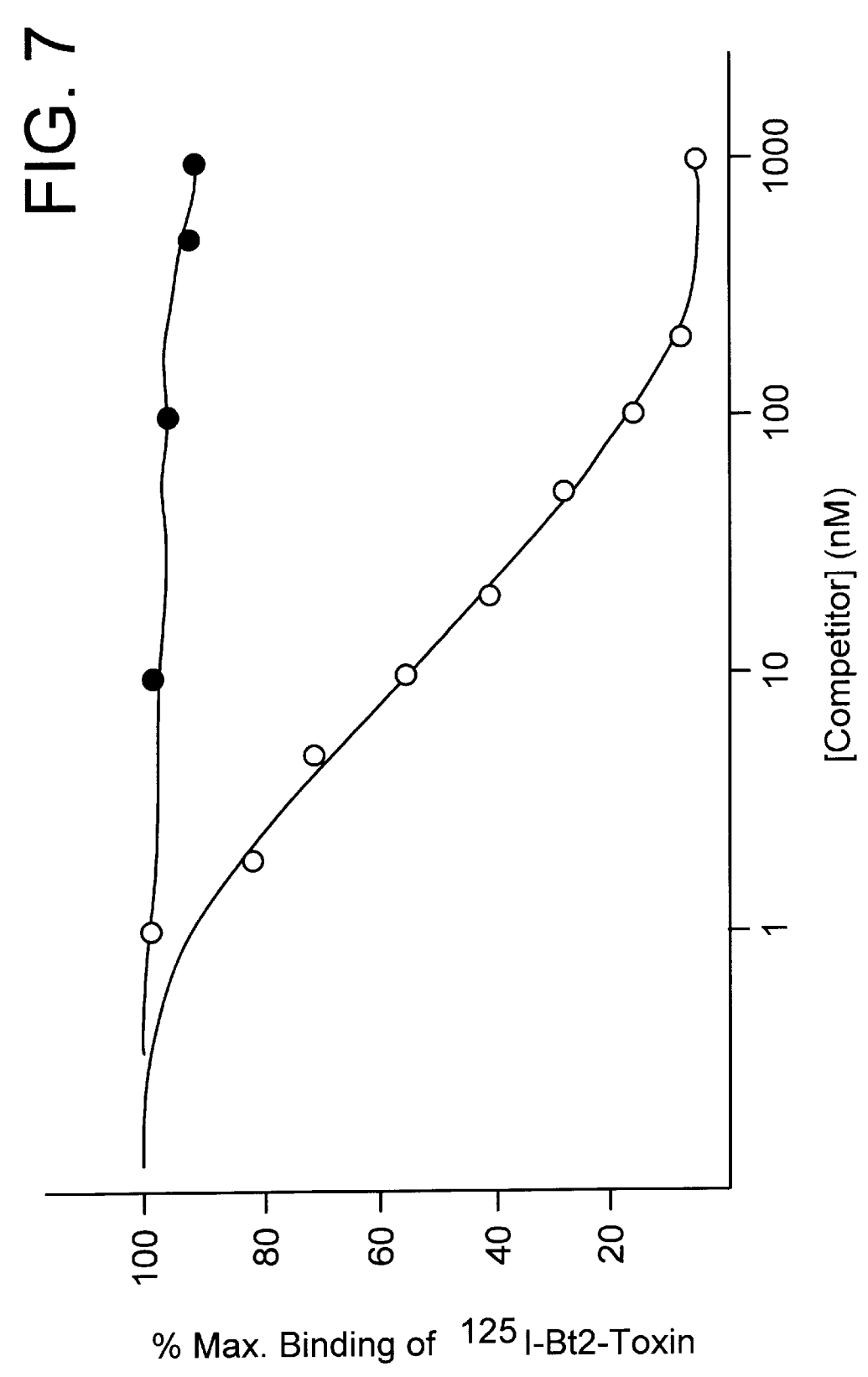
Figure 8:
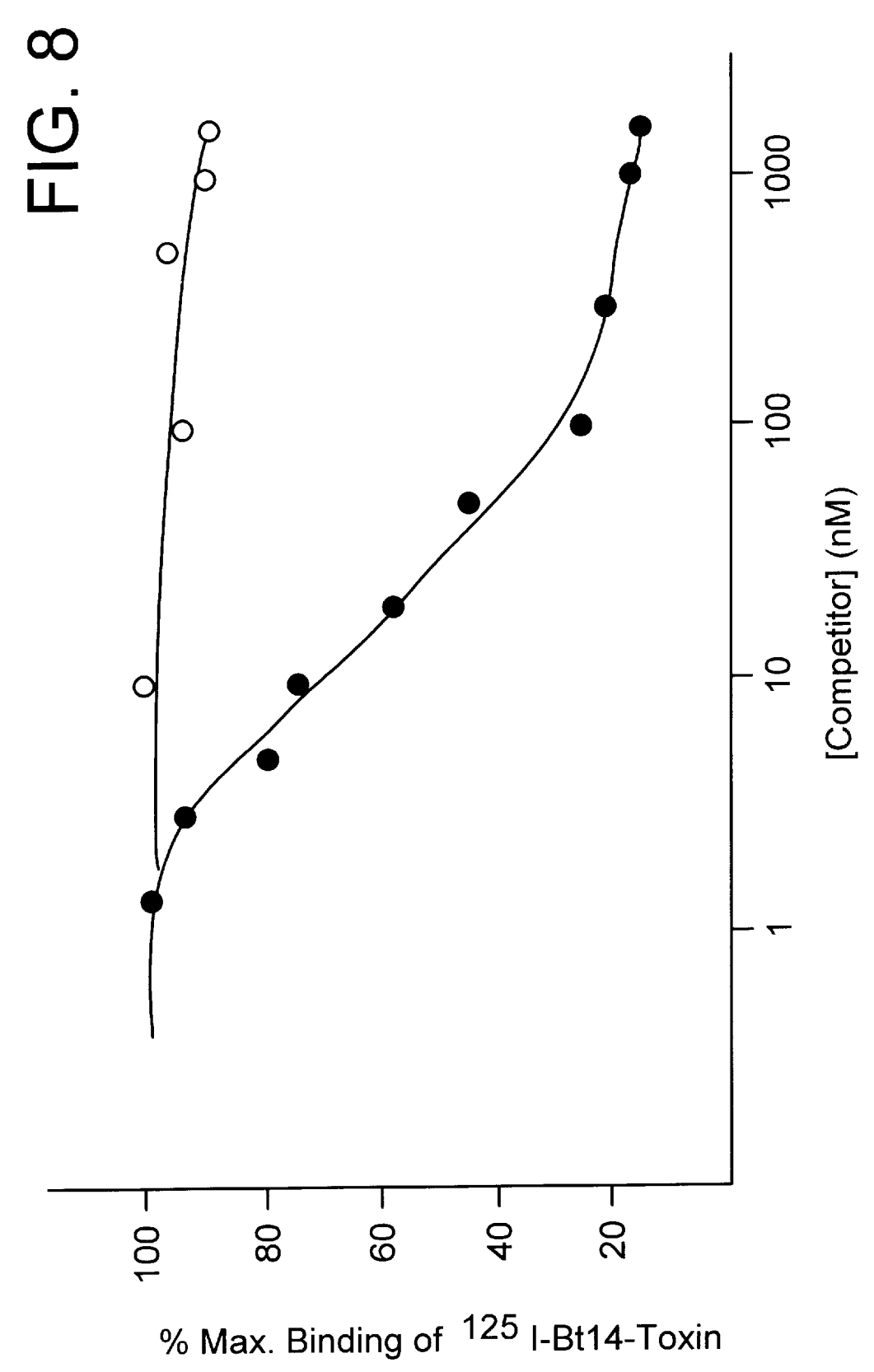

FIGS. 7 and 8 show the binding of $^{125}$I-labeled toxins to *P. brassicae* brush border membrane vesicles. Vesicles were incubated with labeled toxin [in FIG. 7: $^{125}$I-Bt2-toxin (1.05 nM); in FIG. 8: $^{125}$I-Bt14-toxin (1.4 nM)] in the presence of increasing concentrations of Bt2 toxin (○) or Bt14 toxin (●). Binding is expressed as percentage of the amount bound upon incubation with labeled toxin alone. Non-specific binding was not substracted. Data were analyzed with the LIGAND computer program. Each point is the mean of a duplicate sample. FIG. 7 shows the binding of labelled Bt2 toxin to *P. brassicae* BBMV, and FIG. 8 shows the binding of labelled Bt14 toxin to *P. brassicae* BBMV.

The competition data demonstrate the presence of high affinity binding sites both for Bt2 and Bt14, as well as the almost complete absence of competition of Bt14 for the Bt2 binding sites and of Bt14 for the Bt2 binding sites. This demonstrates that Bt2 and Bt14 are non-competitively binding toxins. Hence they are useful to prevent the development of *Pieris brassicae* resistance against *B. thuringiensis* ICP's expressed in Brassica sp. Calculated Kd and Rt values were from these experiments were:

Bt2: Kd=2.8 nM, Rt=12.9 pmol/mg vesicle protein
Bt14: Kd=8.4 nM, Rt=21.4 pmol/mg vesicle protein.

Binding of Bt2 and Bt15 toxins to BBMV of *M.sexta*, *M.brassicae*, *P. xylostella* and *P.interpunctella*: an example of two non-competitively binding Lepidopteran ICPs Bt2 and Bt15 toxins are both toxic to *M.sexta* (LC50's of 20 and 111 ng/cm2, respectively). They also show activity against *M. brassicae*, *P. xylostella* and *P. interpunctella*.

Labelled Bt2 (1.05 nM) or Bt15 (0.7 nM) was incubated with BBMV from *M.sexta* (100 ug protein/ml) in a volume of 0.1 ml in combination with varying amounts of unlabelled Bt2 or Bt15. After a 30 min. incubation period at 22° C., the bound and free toxins were separated.

Figure 9:
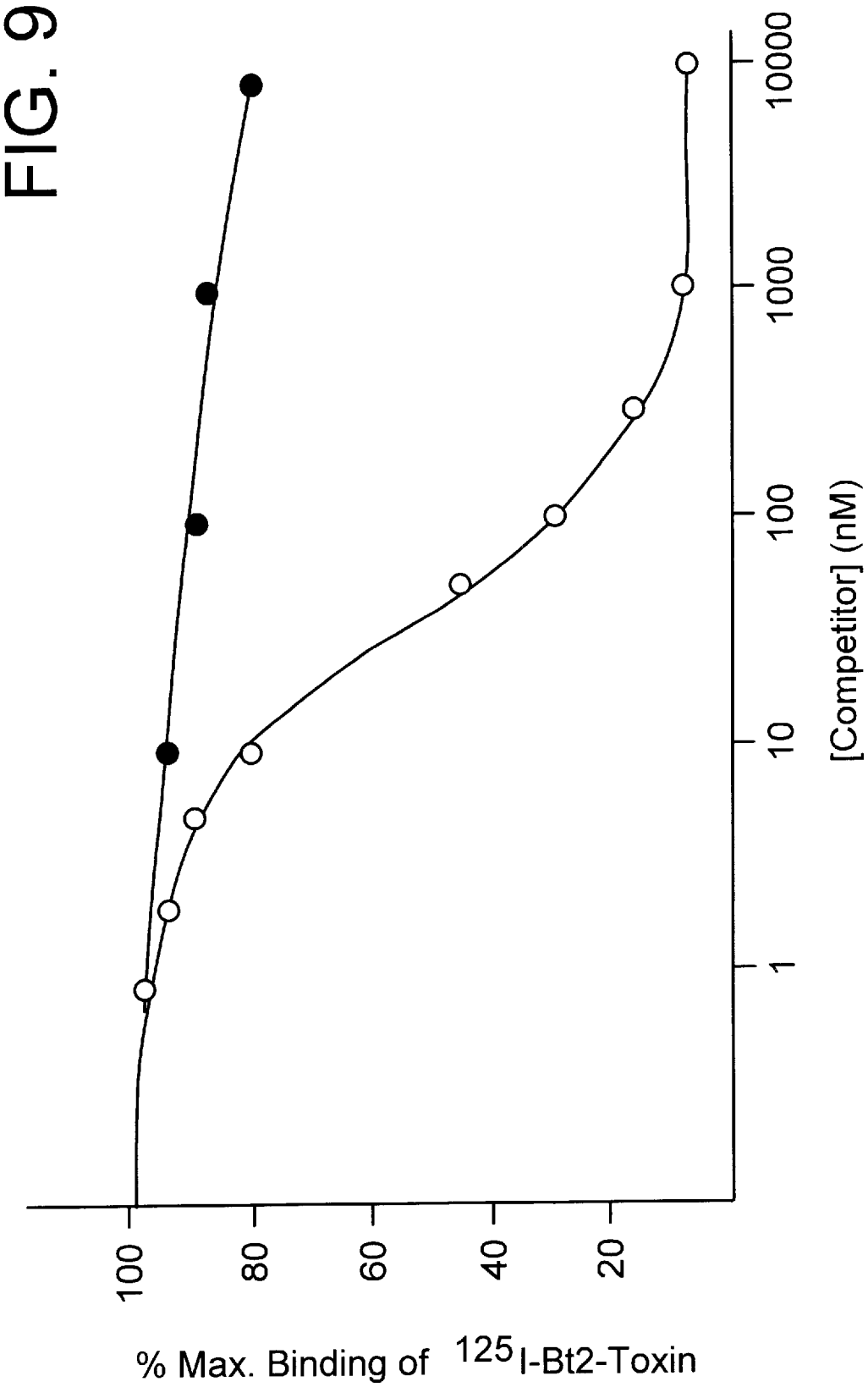
FIG. 9 is a graph showing the binding of $^{125}$I-labeled Bt2 toxin to M. sexta BBMV in the presence of increasing concentrations of Bt2 toxin (○) or Bt15 toxin (●).
Figure 10:
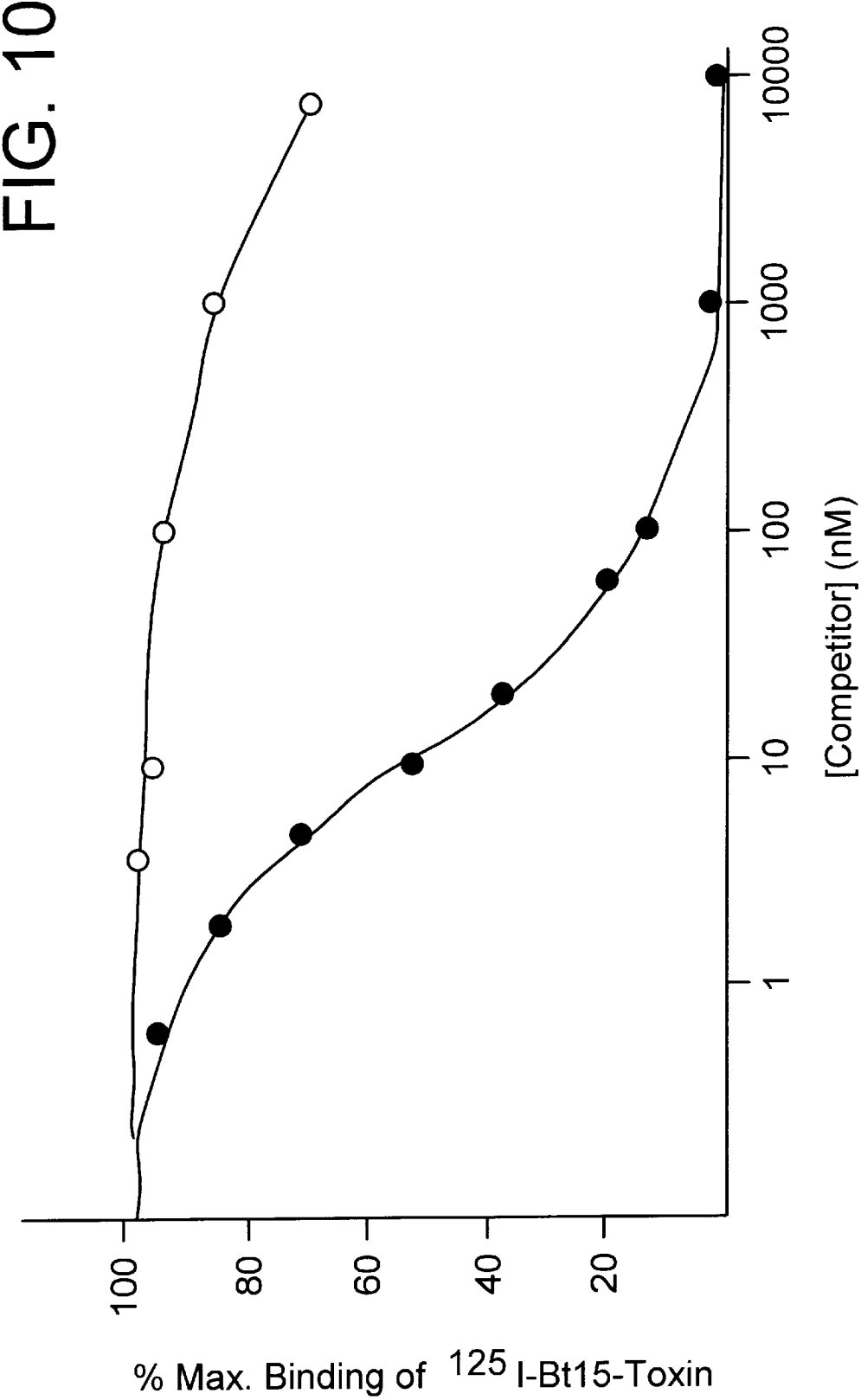
FIG. 10 is a graph showing the binding of $^{125}$I-labeled Bt15 toxin to M. sexta BBMV in the presence of increasing concentrations of Bt2 toxin (○) or Bt15 toxin (●).

FIGS. 9–10 show the binding of $^{125}$I-labeled toxins to *M. sexta* brush border membrane vesicles. Vesicles were incubated with labeled toxin [in FIG. 9: $^{125}$I-Bt2-toxin (1.05 nM); in FIG. 10: $^{125}$I-Bt15-toxin (0.7 nM)] in the presence of increasing concentrations of Bt2-toxin (○) or Bt15-toxin (●). Binding is expressed as percentage of the amount bound upon incubation with labeled toxin alone. Non-specific binding was not substracted. Data were analyzed with the LIGAND computer program. Each point is the mean of a duplicate sample. FIG. 9 shows the data for binding of labelled Bt2, and FIG. 10 shows the binding of labelled Bt15.

The competition data demonstrate the presence of high affinity binding sites for both Bt2 and Bt15, as well as the complete absence of competition of Bt15 for the Bt2 binding sites and of Bt2 for the Bt15 binding sites. This demonstrates that Bt2 and Bt15 are non-competitively binding toxins. Hence the combination of Bt2 and Bt15 is useful to prevent the development of resistance of M.sexta against *B. thuringiensis* ICP's expressed in tobacco or other crops in which Manduca sp. are a pest. Calculated Kd and Rt values are: Bt2: Kd=0.4 nM, Rt=3.4 pmol/mg vesicle protein Bt15: Kd=0.3 nM Kd2=2.9 nM, Rt1=5.9 and Rt2=6.7 pmol/mg vesicle protein (2 distinct high affinity receptor sites are present).

Similar studies were performed for *S. littoralis* and *P. interpunctella*; and are performed for *M. brassicae*. Although LD50, Kd and Rt values differed substantially, the essential observation that Bt2 and Bt15 are both toxic and are non-competitively binding toxins was confirmed in these three insect species. Thus, it is also a useful toxin combination to prevent resistance of *M. brassicae* to ICP's or to prevent resistance of Spodoptera species against ICP's expressed in any of the crop plants in which Spodoptera species are a pest.

Binding of Bt2 and Bt4 toxins to BBMV of *M. sexta*: an example of two non-competitively binding Lepidopteran ICPs Both Bt2 and Bt4 toxins are toxic to *Manduca sexta*. LD50 values are 20 and 5.4. ng/cm2, respectively. No mutual competition of Bt2 for binding of labelled Bt4 and of Bt4 for binding of labelled Bt2 was observed, demonstrating that Bt2 and Bt4 are non-competitively binding toxins.

Binding of Bt15 and Bt18 toxins to BBMV of *S. littoralis*: an example of two non-competitively binding Lepidopteran ICPs Both Bt15 and Bt18 toxins are toxic to *S. littoralis*. LD 50 values are 93 and 88 ng toxin/cm$^2$, respectively. Labelled Bt15 (0.7 nM) or Bt18 (0.9 nM) was incubated with 100 ug of vesicle protein from *S. littoralis* in combination with varying amounts of unlabelled Bt15 or Bt18 toxin. After a 45 min. incubation period, bound and free toxins were separated. Binding data demonstrate high affinity binding for both Bt15 and Bt18 to *S. littoralis* BBMV. As seen from FIGS. 11 and 12, the entire population of receptor sites of Bt15 was not saturable with Bt18, nor was the entire population of receptor sites of Bt18 saturable with Bt15.

Binding of Bt13 and Bt22 toxins to BBMV of *L. decemlineata*: an example of two non-competitively binding Coleopteran ICPs.

Both Bt13 and Bt22 toxins are toxic to *L. decemlineata*. LD 50 values are 0.8 and 1.1 ug toxin/ml respectively. Labelled Bt13 (1 nM) or Bt22 (0.7 nM) was incubated with 100 ug of vesicle protein/ml from *S. littoralis* in combination with varying amounts of unlabelled Bt13 or Bt22 toxin. After a 45 min. incubation period, bound and free toxins were separated. Binding data demonstrate high affinity binding for both Bt13 and Bt22 to *S. littoralis* BBMV. The entire population of receptor sites of Bt13 was not saturable with Bt22. Nor is the entire population of receptor sites of Bt22 saturable with Bt13.

Binding of Bt2 and Bt18 toxins to BBMV of *M. sexta*: an example of two non-competitively binding Lepidopteran ICPs.

Both Bt2 and Bt18 toxins are toxic to *M. sexta*, and LD 50 values are 20 to 73 ng toxin/cm$^2$ respectively. Labelled Bt2 (1.05 nM) or Bt18 (0.7 nM) was incubated with 100 ug/ml of vesicle protein from *M. sexta* in combination with varying amounts of unlabelled Bt2 or Bt18 toxin. After a 45 min. incubation period, bound and free toxins were separated. Binding data (FIGS. 11–12) demonstrate high affinity binding for both Bt2 and Bt18 to *M. sexta* BBMV. The entire population of receptor sites of Bt2 was not saturable with Bt18. Nor was the entire population of receptor sites of Bt18 saturable with Bt2. Calculated Kd and Rt values are: Bt2: Kd=0.4 nM, Rt=3.4 pmol/mg vesicle protein. Bt18: Kd1= 0.04 nM, Rt1=2.2 pmoles/mg vesicle protein and Kd2=168 nM Rt2=194 pmoles/mg vesicle protein (2 distinct receptor sites for Bt18 are present).

A list of non-competitively binding anti-Lepidopteran ICP combinations is given below, together with their common target insect species in which non-competitivity has been demonstrated:

Bt2–Bt15 (*Manduca sexta, Plutella xylostella, Plodia interpunctella*)

Bt2–Bt18 (*Manduca sexta, Spodoptera littoralis*)

Bt2–Bt14 (*Pieris brassicae, Plutella xylostella, Phthorimaea operculella*)

Bt2–Bt4 (*Manduca sexta*)

Bt15–Bt18 (*Manduca sexta, Spodoptera littoralis*)

Bt15–Bt4 (*Manduca sexta*)

Bt18–Bt4 (*Manduca sexta, Spodoptera littoralis*)

Bt18–Bt4 (*Manduca sexta*)

Also included in this list of non-competitively binding ICP combinations, together with their common target insect species in which non-competitivity is demonstrated are:

Bt2–Bt15 (*Pieris brassicae, Mamestra brassicae*)

Bt14–Bt15 (*Pieris brassicae*)

Bt15–Bt4 (*Spodoptera exigua*)

Bt18–Bt14 (*Pieris brassicae*)

Bt13–Bt21 (*Lepinotarsa decemlineata*)

Bt13–Bt22 (*Lepinotarsa decemlineata*)

Bt21–Bt22 (*Lepinotarsa decemlineata*).

Of course, this list of specific non-competitively binding ICP combinations for specific target insect pests is not exhaustive, and it is believed that other such ICP combinations, including combinations for yet-to-be discovered ICPs, will be found using a similar approach for any target insect species. Likewise, the foregoing list of target insect pests also is not exhaustive, and it is believed that other target insects pests (as well as the plants that are to be transformed to prevent their attack by such pests), against which the specific combinations of ICPs can be used (e.g., the combination of the Bt2 and Bt14 ICPs in Brassica to prevent resistance of *Pieris brassicae* against the ICPs expressed in the plant), will be found using a similar approach.

EXAMPLE 7

Selection for resistance of *Manduca sexta* (tobacco hornworm)

A selection experiment involves exposing a large number of larvae to a concentration of a toxin in a diet killing (e.g., 50–90%) of the larvae. The surviving larvae are again exposed to toxin concentrations killing a similar proportion of the larvae, and this process is continued for several generations. The sensitivity of the larvae to the toxin is investigated after each four generations of selection.

Selections for 20 generations of *M. sexta* were performed with Bt2 toxin alone, with Bt18 toxin alone and with a 1/4 (by weight) Bt2/Bt18 mixture. LC50 values of the reference strain for Bt2, Bt18 and the 1/4 Bt2/Bt18 mixture respectively were the following: 20 ng/cm2, 73 ng/cm2 and 62 ng/cm2 of diet.

Selection was initiated at concentrations killing around 75% of the larvae. After 4 generations of selection, survival increased in both the Bt2 and the Bt18 selection to around 70%, no such increase was observed in the selection with the combination of Bt2 and Bt18. Dosages were again increased to calculated LC75 values. This was repeated every 4 generations. The selection process was thus continued to the 20th generation. Final results were the following (LC50 of the 20th generation):

Bt2 selection: LC50 was 6400 ug/g (320 times decreased sensitivity)

Bt18 selection: LC50 was 15100 ug/g (207 times decreased sensitivity)

Bt2/Bt18 selection: LC50 was 181 ug/g (3 times decreased sensitivity).

Thus the decrease in sensitivity was about 100 times slower in the combined selection experiment.

Receptor binding in the three selected *M. sexta* strains was investigated with Bt2 and Bt18 and compared to those of the reference *M. sexta* strain (non-selected strain). Binding characteristics of the reference strain for the Bt2 and BT18 toxins were:

Bt2: Kd=0.4 nM, Rt=3.4 pmol/mg vesicle protein

Bt18: Kd1=0.04 nM, Rt1=2.2 pmoles/mg vesicle protein and Kd2=168 nM, Rt2=194 pmoles/mg vesicle protein (2 distinct receptor sites for Bt18 are present).

Figure 11:
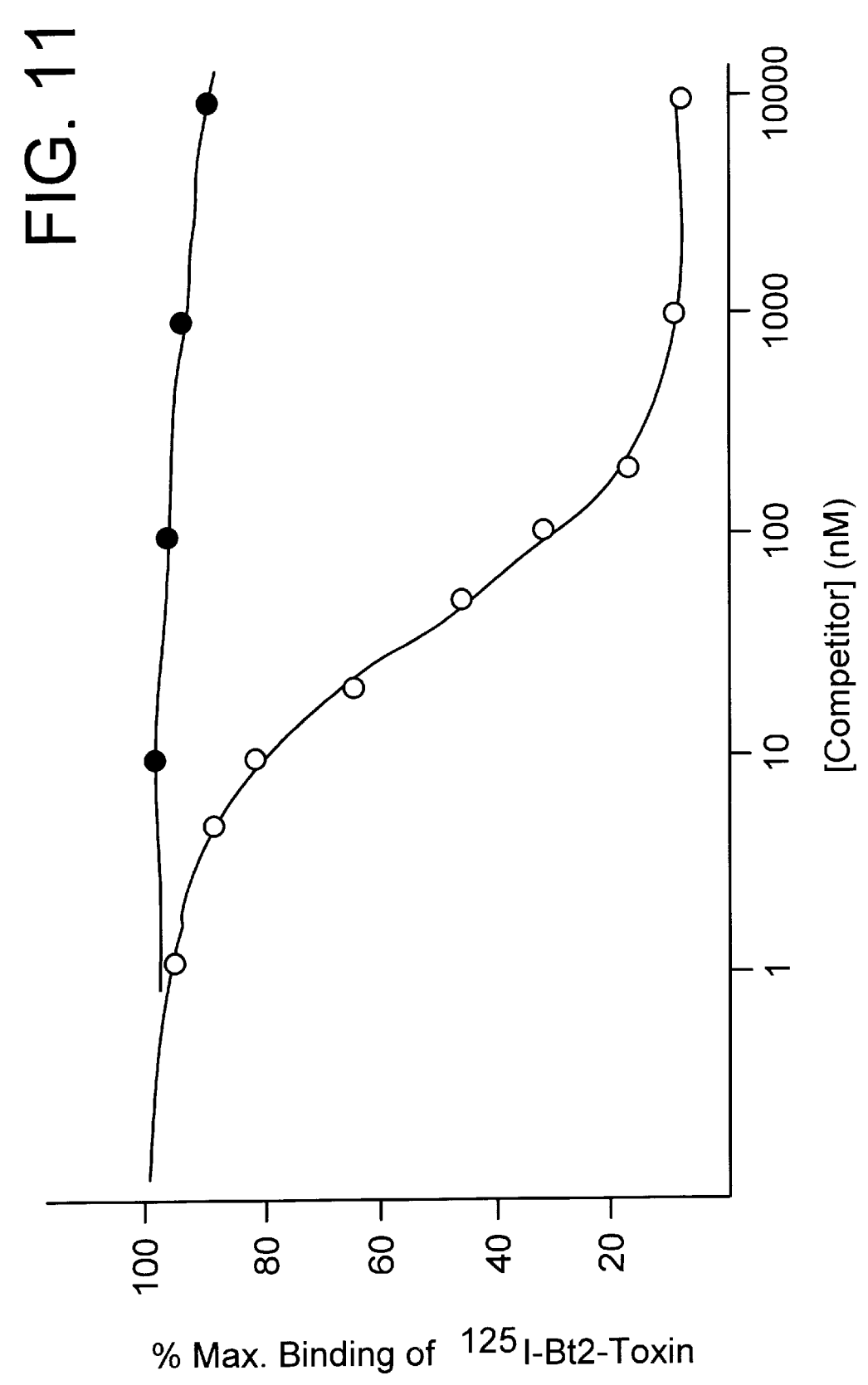

FIGS. 11 and 12 show the binding of $^{125}$I-labeled toxins to *M. sexta* brush border membrane vesicle. Vesicles were incubated with labeled toxin [in FIG. 11: $^{125}$I-Bt2-toxin (1.05 nM); in FIG. 12: $^{125}$I-Bt18-toxin (0.7 nM)] in the presence of increasing concentrations of Bt2-toxin (○) or Bt18-toxin (●). Binding is expressed as percentage of the amount bound upon incubation with labeled toxin alone. Non-specific binding was not substracted. Data were analyzed with the LIGAND computer program. Each point is the mean of a duplicate sample.

The Bt2 selected strain showed no detectable high affinity binding of Bt2 whereas its Bt18 binding characteristics remained close to the reference strain. (Bt18: Kd1=0.03 nM, Rt1=2.8 pmoles/mg vesicle protein and Kd2=199 nM, Rt2= 109 pmoles/mg vesicle protein; 2 distinct receptor sites for Bt18 are still present).

The Bt18 selected strain lost the high affinity receptor site for Bt18. The lower affinity site for Bt18 was still present in lower concentration than in the reference strain (Kd=189 nM, Rt=43 nM). Bt2 binding site concentration increased markedly compared to the reference strain (Kd=0.4 nM, Rt=20.8 pmoles/mg vesicle protein). This strain had a Bt2 sensitivity of $LC_{50}$=4 ng/cm$^2$. Thus, its sensitivity for Bt2 had increased as compared to the reference strain ($LC_{50}$=20 ng/cm$^2$).

The Bt2/Bt18 selected strain showed a slight but statistically non-significant decrease in Bt18 binding site concentration. (Bt2: Kd=0.4 nM, Rt=3.4 pmol/mg vesicle protein, Bt18: Kd1=0.04 nM, Rt1=1.0 pmoles/mg vesicle protein and Kd2=168 nM, Rt2=194 pmoles/mg vesicle protein; 2 distinct receptor sites for Bt18 are present). These data demonstrate that, in the two selection lines where resistance occurred, the mechanism was situated at the receptor level. Changes in receptor site are shown to be the most likely mechanism of resistance to *B. thuringiensis* ICPs.

EXAMPLE 8

Mechanism of resistance of the diamondback moth to the microbial insecticide *Bacillus thuringiensis*.

The mechanism of development of insect resistance to ICPs has been investigated in a *P. xylostella* strain ("PxR"). This insect strain has developed a high level of resistance in the field against Dipel. Crystals of Dipel preparations contain a mixture of ICPs such as Bt3, Bt2 and Bt73 ICPs; in Example 6, it has been shown that these toxins are competitively binding ICPs.

Resistance to Dipel was confirmed by the toxicity data for the sensitive strain ("PxS") and for the Dipel-resistant strain ("PxR"). High levels of resistance are also observed for the Bt2 protoxin and toxin as shown in the following table:

|  | PxS | $LC_{50}$ of Strains PxR |
|---|---|---|
| Bt2 | 6.7 | >1350 |
| Bt15 | 132.6 | 120.4 |

$LC_{50}$ data are expressed as ng protein spotted per cm$^2$ of artificial diet.

However, insect toxicity data show that there is no resistance to the Bt15 protoxin and Bt15 toxin; this ICP is not present in Dipel crystals. To investigate whether a change in toxin-membrane binding was responsible for resistance, receptor binding studies were performed with $^{125}$I-labeled Bt2 toxin and Bt15 toxin, with BBMV derived from larvae midguts of the PxR and PxS strains. The results are summarized in Table 1, below.

TABLE 1

Binding characteristics of Bt2 and Bt15 toxins to brush border membrane vesicles from sensitive and (resistant *P. xylostella*.)

| ICP | strain | Kd (nM) | Rt (pmol/ mg protein) |
|---|---|---|---|
| Bt2 toxin | PxS | 8.1 | 1.6 |
|  | PxR | no binding detectable | |
| Bt15 toxin | PxS | 1.9 | 4.2 |
|  | PxR | 3.7 | 5.8 |

Table 1 shows that there was high-affinity saturable binding of the Bt2 toxin to midgut membranes of the PxS strain, but the PxR strain showed no detectable level of Bt2 toxin binding. With the Bt15 toxin, there was significant binding to BBMW of both the PxR and PxS strains, and values are not significantly different for the two strains.

These data show that resistance in *P. xylostella* is due to an alteration in toxin-membrane binding. Resistance to the Bt2 toxin and the sensitivity toward the Bt15 toxin of the PxR strain is reflected by the binding characteristics shown in Table 1.

Hence, when different non-competitively binding ICPs (i.e., Bt2 and Bt15) are available with activity against the same insect species (e.g., *P. xylostella*), resistance to one ICP(Bt2) does not imply resistance against other ICPs (such as Bt15). Thus, ICPs with different binding properties can be used in combination to delay development of insect resistance to ICPs.

EXAMPLE 9

Separate transfer of two ICP genes within individual transcriptional units to the genome of plant cells Two procedures are envisaged for obtaining the combined expression of two ICP genes, such as the bt2 and bt15 genes in transgenic plants, such as tomato plants. These procedures are based on the transfer of two chimeric ICP genes, not linked within the same DNA fragment, to the genome of a plant of interest.

A first procedure is based on sequential transformation steps in which a plant, already transformed with a first chimeric ICP gene, is retransformed in order to introduce a second ICP gene. The sequential transformation makes use of two different selectable marker genes, such as the resistance genes for kanamycin ("km") and phosphinotricin acetyl transferase ("PPT"), which confers resistance to phoshinotricin. The use of both these selectable markers has been described in De Block et al. (1987).

The second procedure is based on the cotransformation of two chimeric ICP genes on different plasmids in a single step. The integration of both ICP genes can be selected by making use of the two selectable markers conferring resistance to Km and PPT, linked with the respective ICP genes.

For either procedure, a Ti-plasmid vector is used for Agrobacterium-mediated transformation of each chimeric ICP gene into plant cells.

Plasmid pGSH163, described in EP 0193259, contains the following chimeric genes between the T-DNA border repeats: a gene fragment encoding the toxin part of the bt2 gene under the control of the TR2' promoter and the neo gene under control of the TR1' promoter. The 3' ends of the T-DNA gene 7 and octopine synthase respectively provide information for the 3' end formation of transcripts.

A chimeric bt15 gene containing a gene fragment encoding the toxin of the Bt15 ICP under the control of the TR2' promoter, was constructed in the following way (FIG. 15). pOH50 consists of pUC18 with the whole bt15 gene under the control of the lac promoter. A HindIII-BglII fragment was cloned in pMa5-8 yielding pJB3. By site-directed mutagenesis, a NcoI site was created at the initiation codon to yield pVE29. A fragment containing the truncated gene fragment of the bt15 gene, with a translational stop codon, was obtained by isolation of BclI-ClaI from pOH50 and cloning in pLK91, yielding pHW38. The whole toxin gene fragment was reconstructed under the control of the tac promoter, yielding pVE35, by ligation of a ClaI-PstI fragment from pHW38, a NcoI-ClaI fragment from pVE29 and a NcoI-PstI fragment from pOH48. A truncated bt15 gene fragment with a NcoI site at the initiation codon was obtained from pVE35 as a 1980 NcoI-BamHI fragment and cloned in pGSJ141, digested with ClaI and BamHI. pGSJ141 has been described in EPA 88402115.5. Ligation of the filled ClaI site to the filled NcoI site yielded a chimeric TR2'-truncated bt15-3'g7 construct (pTVE47). As a selectable marker in this plasmid, the bar gene encoding phosphinothricin acetyl transferase and conferring resistance to PPT was used. A chimeric bar gene containing the bar gene under the control of the 35S promoter and followed by the 3' end of the octopine synthase was introduced in pTVE47. From pDE110, a 35S-bar-3'ocs fragment was obtained as a StuI-HindIII fragment and was cloned in pTVE47 digested with PstI and HindIII. This yielded the plasmid pTHW88 (FIG. 15) which contains the truncated bt15 gene under the control of the TR2' promoter and the bar gene under the control of the 35S promoter between the T-DNA border repeats. Plasmid pGSH163 is cointegration type Ti-plasmid vector, whereas pTHW88 is a binary type Ti-plasmid vector as described in EPA 0193259.

Both plasmids were mobilized in the *A. tumefaciens* strain C58C1Rif (pGV2260) according to Deblaere et al. (1988). In the sequential transformation procedure, tomato was transformed according to De Block et al. (1987) with the *A. tumefaciens* strain C58C1Rif carrying pGS1163 resulting from the cointegration of pGSH163 and pGV2260. Individual transformants were selected for kanamycin resistance, and regenerated plants were characterized for expression of the truncated bt2 gene according to Vaeck et al. (1987). One representative transformant was subsequently retransformed with the *A. tumefaciens* strain C58C1Rif (pGV2260 and pTHW88), and transformants were selected for PPT resistance. Using this cotransformation procedure, the respective Agrobacteria strains, carrying the cointegrate vector pGS1163 and the binary vector pTHW88, were used for transformation of tomato. Individual plants were selected for resistance to Km and PPT.

Figure 15A:
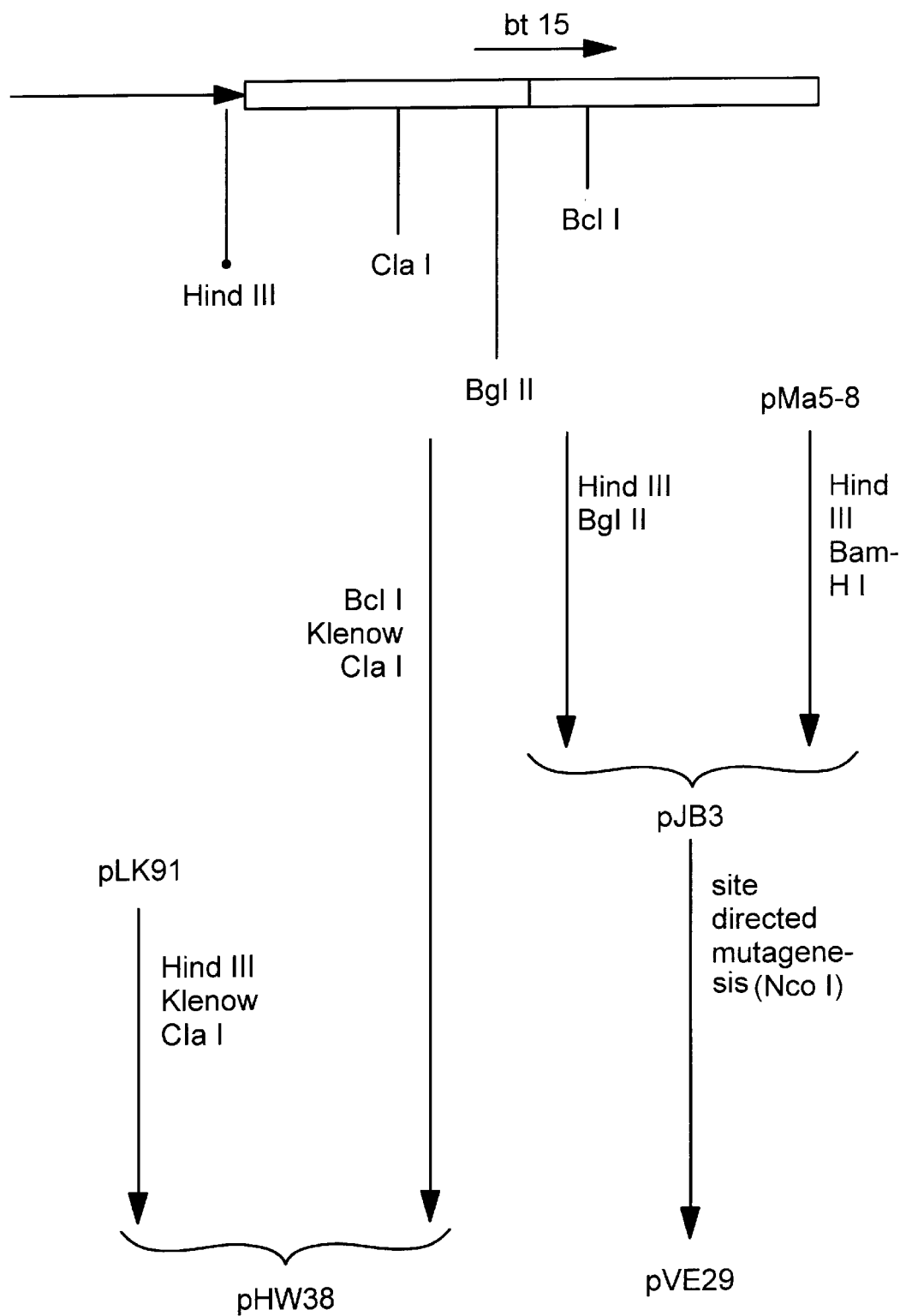
FIGS. 15A–15C schematically depict construction of pVE29, PVE35 and pTHW88.
Figure 15B:
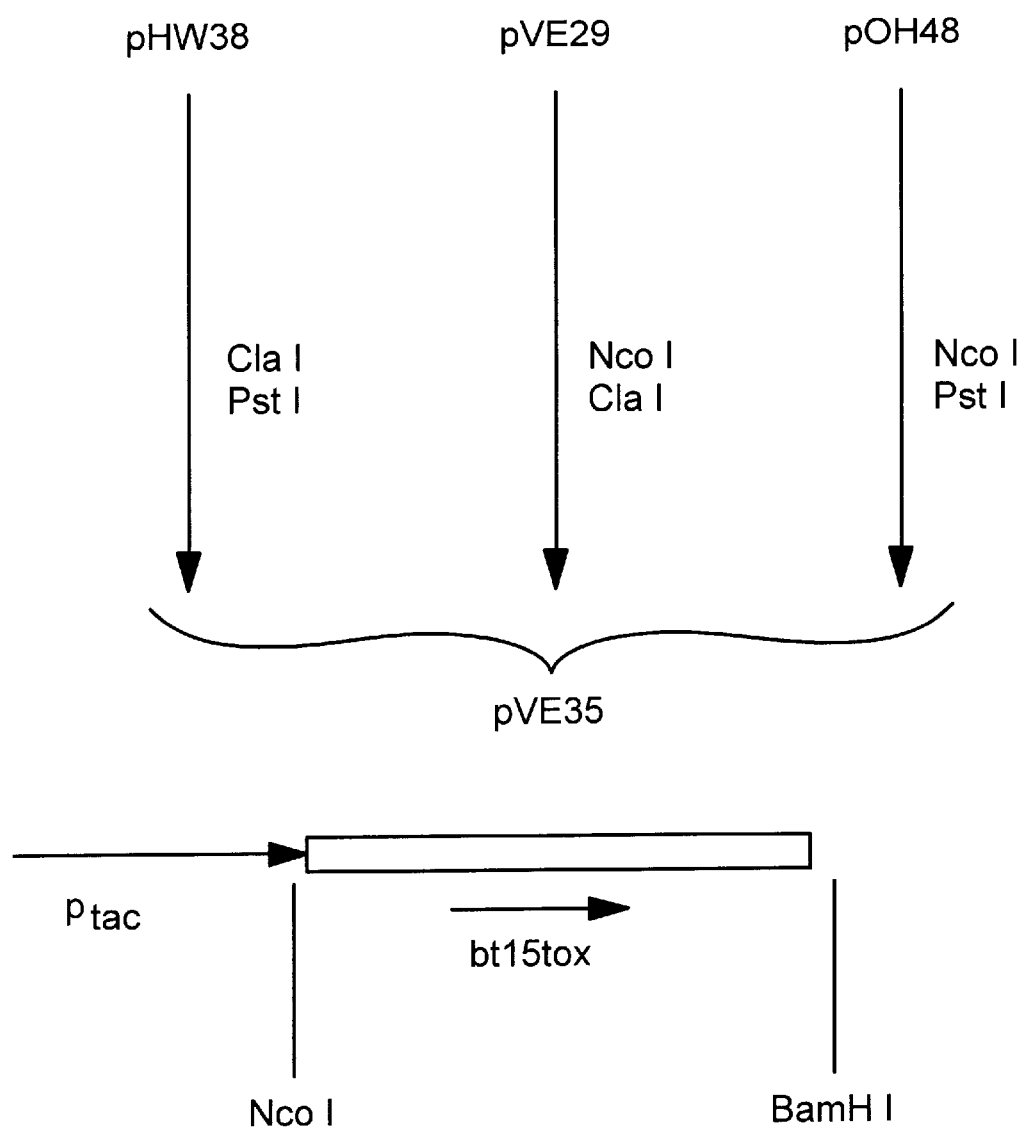
Figure 15C:
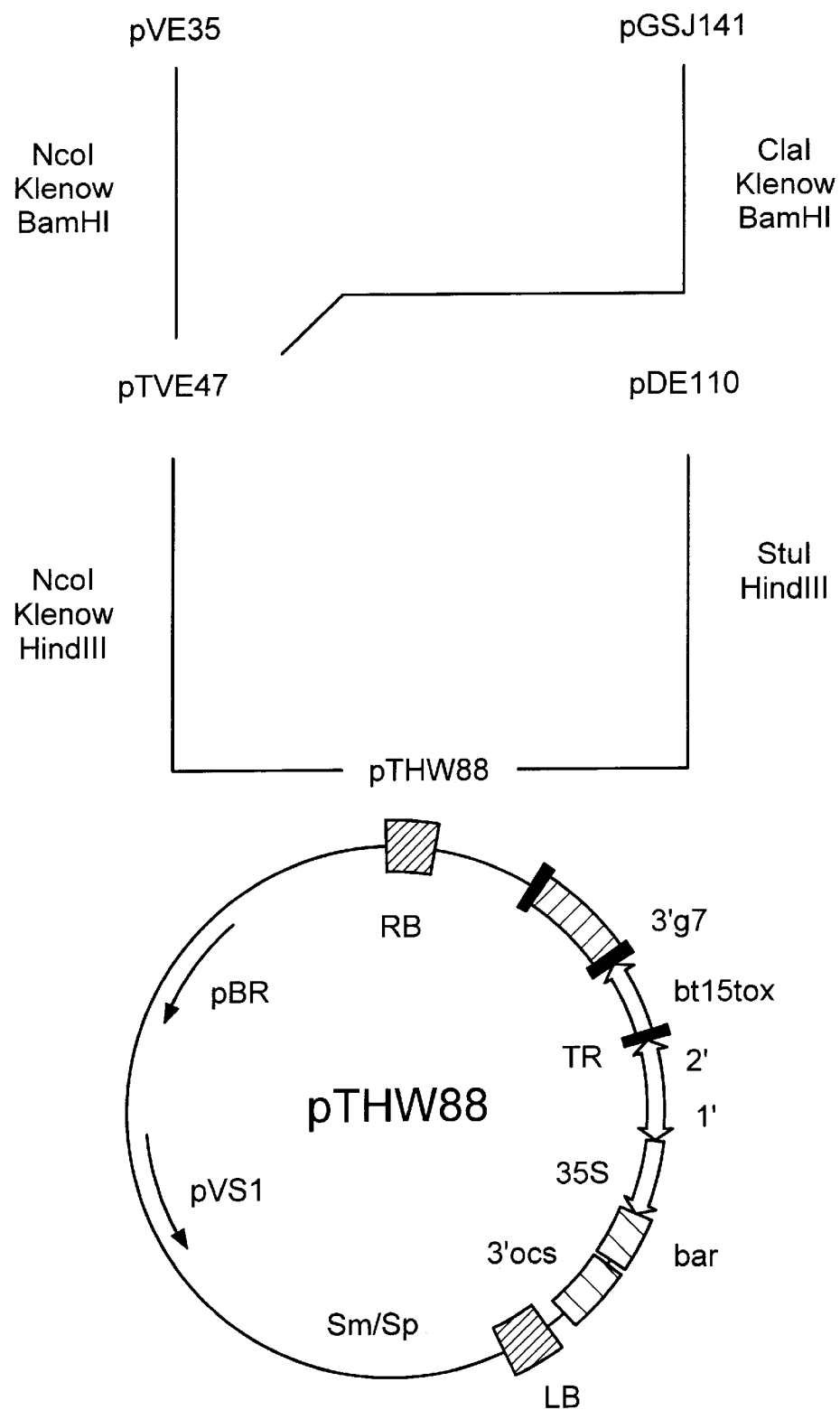
Figure 16A:
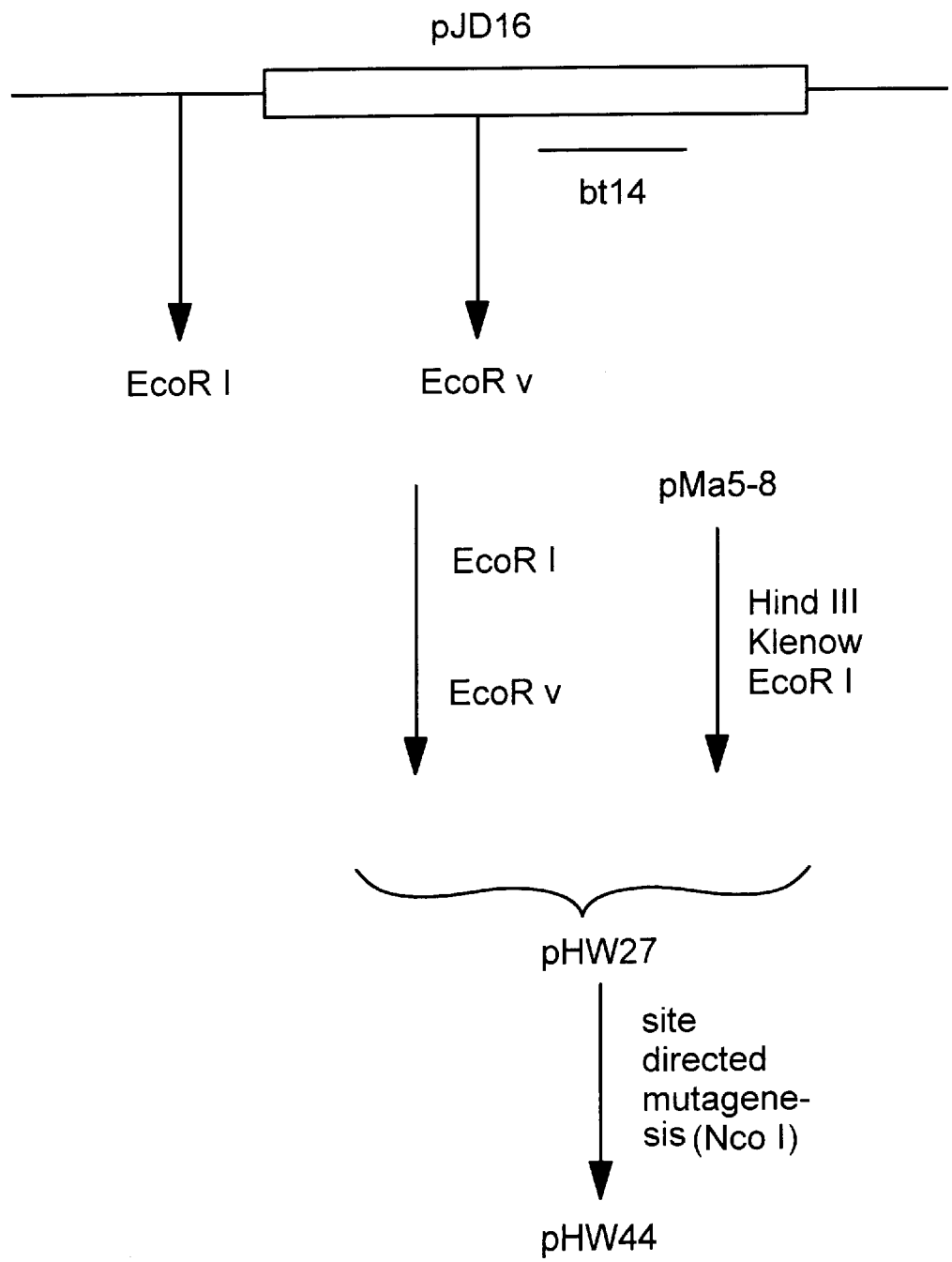
FIGS. 16A–16E schematically depict construction of pHW44, pHW67, pHW71 and pTHW94.
Figure 16B:
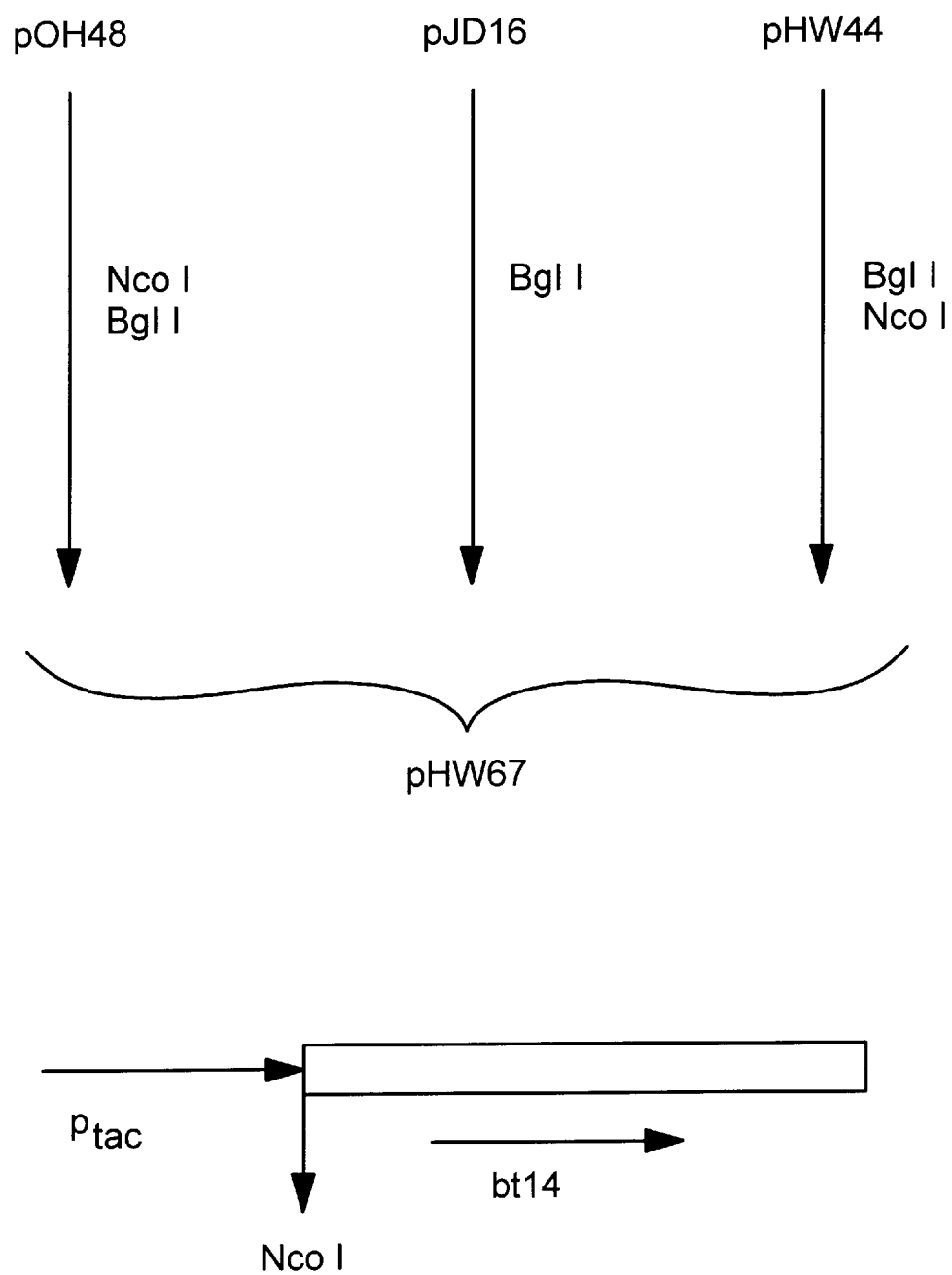
Figure 16C:
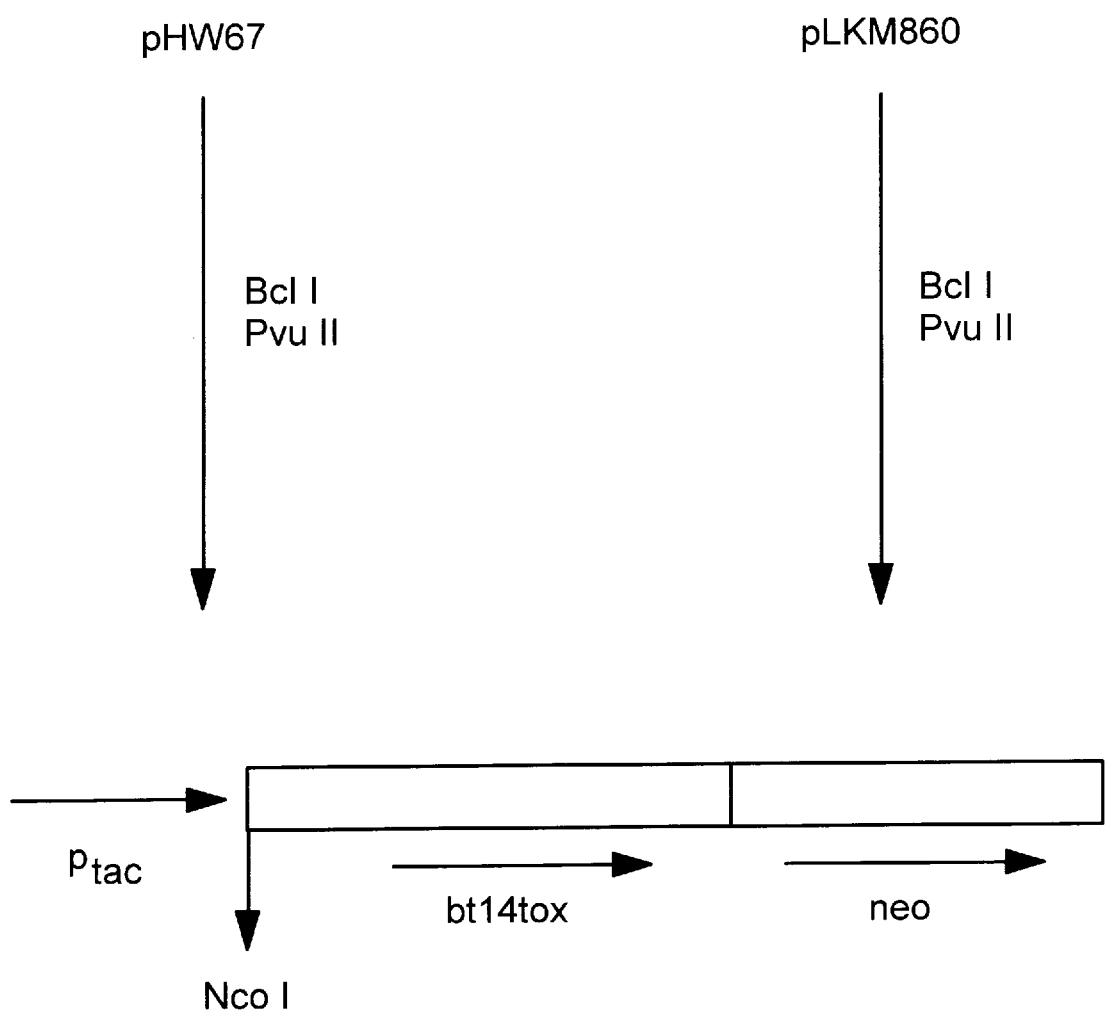
Figure 16D:
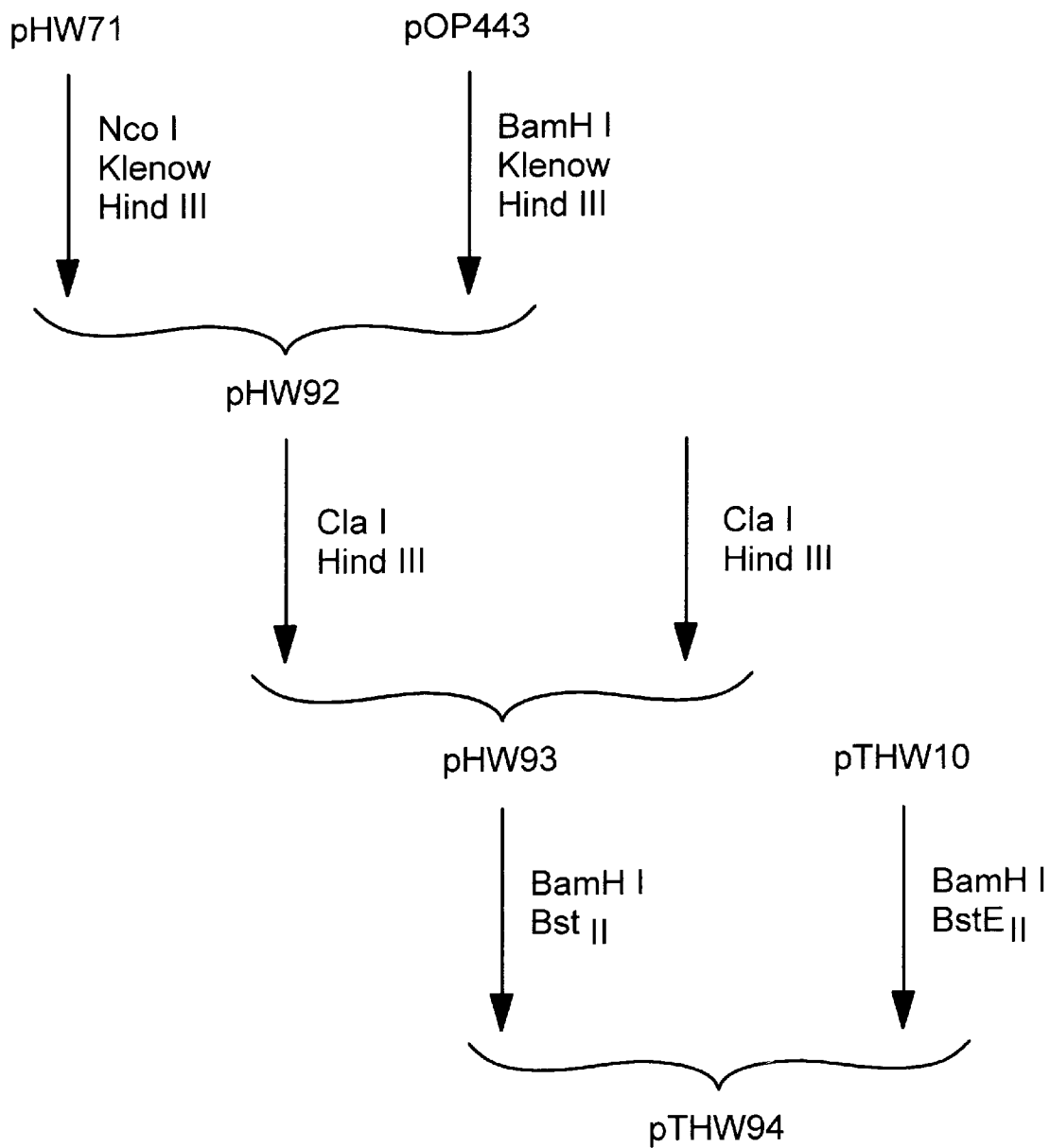
Figure 16E:
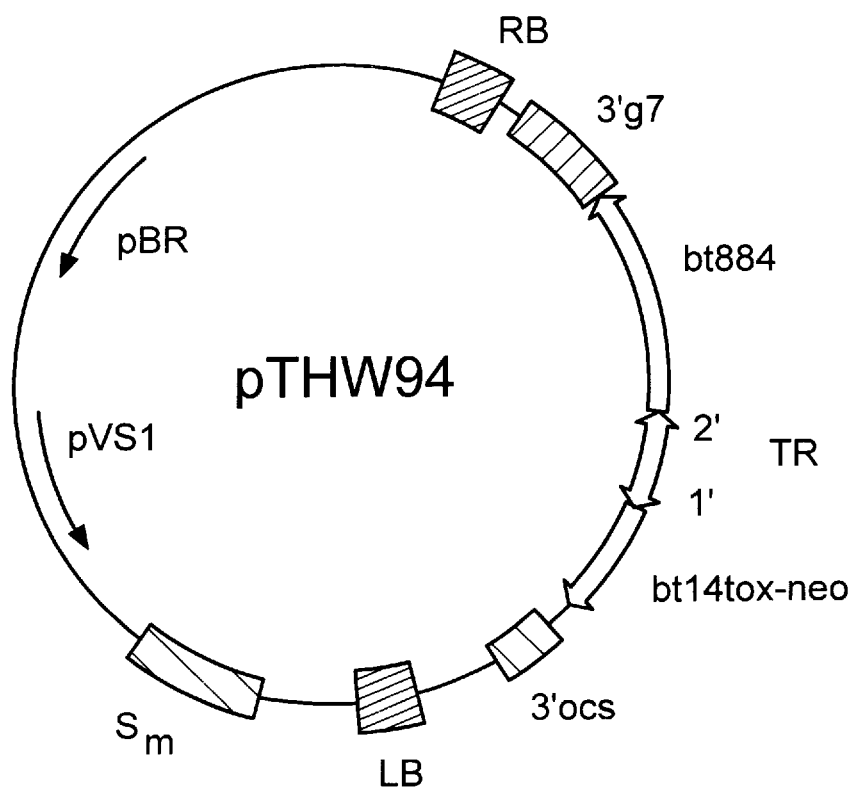

Schematically shown in FIG. 15 are:
a) construction of pVE29: bt15 N-terminal gene fragment with NcoI site introduced at ATG initiation codon.
b) construction of pVE35: bt15 C-terminal truncated gene fragment under control of the tac promoter.
c) construction of pTHW88: binary T-DNA vector with a chimeric bt15 gene and a chimeric bar gene within the T-DNA border repeats.

In both cases, co-expression of the two ICP genes in the individual transformants was evaluated by insect toxicity tests as described in EP 0193259 and by biochemical means. Specific RNA probes allowed the quantitive analysis of the transcript levels; monoclonal antibodies cross-reacting with the respective gene products allowed the quantitative analysis of the respective gene products in ELISA tests (EP 0193259); and specific DNA probes allowed the characterization of the genomic integrations of the bt2 and bt15 genes in the transformants. It was found that the transformed tomato plants simultaneously expressed both the bt2 gene (8.1 ng/mg) and the bt15 gene (7.6 ng/mg) as measured by ELISA, which would prevent or delay development of resistance of *M. sexta* to the insecticidal effects of the Bt2 and Bt15 toxins, being expressed.

These procedures also could be applied when one or both ICP genes are part of a hybrid gene. For example, the same strategy as described above could be followed with the plasmid vectors pGSH152, containing a chimeric truncated bt2-neo hybrid gene under control of the TR2' promoter, and pTHW88 in suitable Agrobacterium strains.

EXAMPLE 10

Separate transfer of two ICP genes to the nuclear genome of separate plants in independent transformation events and subsequent combination in a single plant through crossing.

Tobacco plants have been transformed with either the bt18 gene or the bt15 gene by applying the same cloning strategies as described in EP 0358557 and EP 193259, respectively. For both genes, the plants were transformed with plant expression vectors containing either the truncated bt18 or bt15 gene, which just encode the Bt18 or Bt15 toxin, respectively.

The mortality rate of *Spodoptera littoralis* larvae feeding on the transformed plants is significantly higher than the mortality rate of larvae fed on untransformed plants.

The bt18-transformed plant, which is homozygous for the bt18 gene, is then crossed with the bt15-transformed plant, which is homozygous for the bt15 gene. After selfing, a plant homozygous for both genes is obtained.

The resulting tobacco plants, expressing both the bt18 and bt15 genes, delay significantly development of resistance by *S. littoralis* to either the Bt18 or Bt15 toxin expressed by the plants.

EXAMPLE 11

Transfer of two chimeric ICP genes linked within the same DNA to the genome of plant cells The strategy used is based on the organization of two independent chimeric ICP genes between the T-DNA border repeats of a single vector. Binding studies indicated that the Bt2 and Bt14 toxins are two non-competitively binding ICPs with insecticidal activity towards *Pieris brassicae*. For expression in plants, both the bt2 and bt14 genes can be co-expressed to prevent insect resistance development. For the design of a plasmid vector with each ICP gene under the control of a separate promoter, two possibilities can be envisaged: 1) three chimeric constructs carrying the truncated bt2 and bt14 genes and a selectable marker, respectively; or 2) a hybrid of a truncated gene fragment (bt2 or bt14) and the neo gene can be used in combination with a truncated bt14 or bt2 gene.

This Example describes the construction of the vector pTHW94 for plant transformations carrying the following chimeric ICP genes between the T-DNA border repeats: a truncated bt2 gene fragment under the control of the TR2' promoter and a hybrid truncated bt14-neo gene under the control of the TR1' promoter. The 3' end of the T-DNA gene 7 and octopine synthase, respectively, provide information for proper 3' end formation. pTHW94 has been deposited at the DSM under accession no. 5514 on Aug. 28, 1989.

Schematically shown in FIG. 16 are the:
a) construction of pHW44: bt14 N-terminal gene fragment with NcoI site introduced at ATG initiation codon.
b) construction of pHW67: reconstruction of the bt14 gene under the control of the tac promoter.
c) construction of pHW71: construction of a hybrid truncated bt14-neo gene under the control of the tac promoter.
d) construction of pTHW94: binary T-DNA vector with a chimeric bt14 gene and a chimeric bt2 gene within the T-DNA border repeats.

The pTHW94 vector is mobilized into the Agrobacterium strain C58C1Rif (pMP90) which is used to transform *Brassica napus* according to the procedure described by De Block et al. (1989). Transformants are selected on Km, and regenerated plants are found to express both ICP gene products in insect toxicity tests and biochemical tests.

EXAMPLE 12

Expression of two ICP genes in a hybrid construct

In order to obtain a combined and simultaneous expression of two ICP genes, truncated gene fragments encoding the toxic parts of two different ICPs can be fused in a proper reading frame and placed, as a hybrid gene, under the control of the same promoter in a chimaeric gene construct. Toxic cores from certain ICPs can be liberated from their protoxins by protease activation at the N- and/or C- terminal end. Thus, hybrid genes can be designed with one or more regions encoding protease cleavage site(s) at the fusion point(s) of two or more ICP genes.

Figure 17:
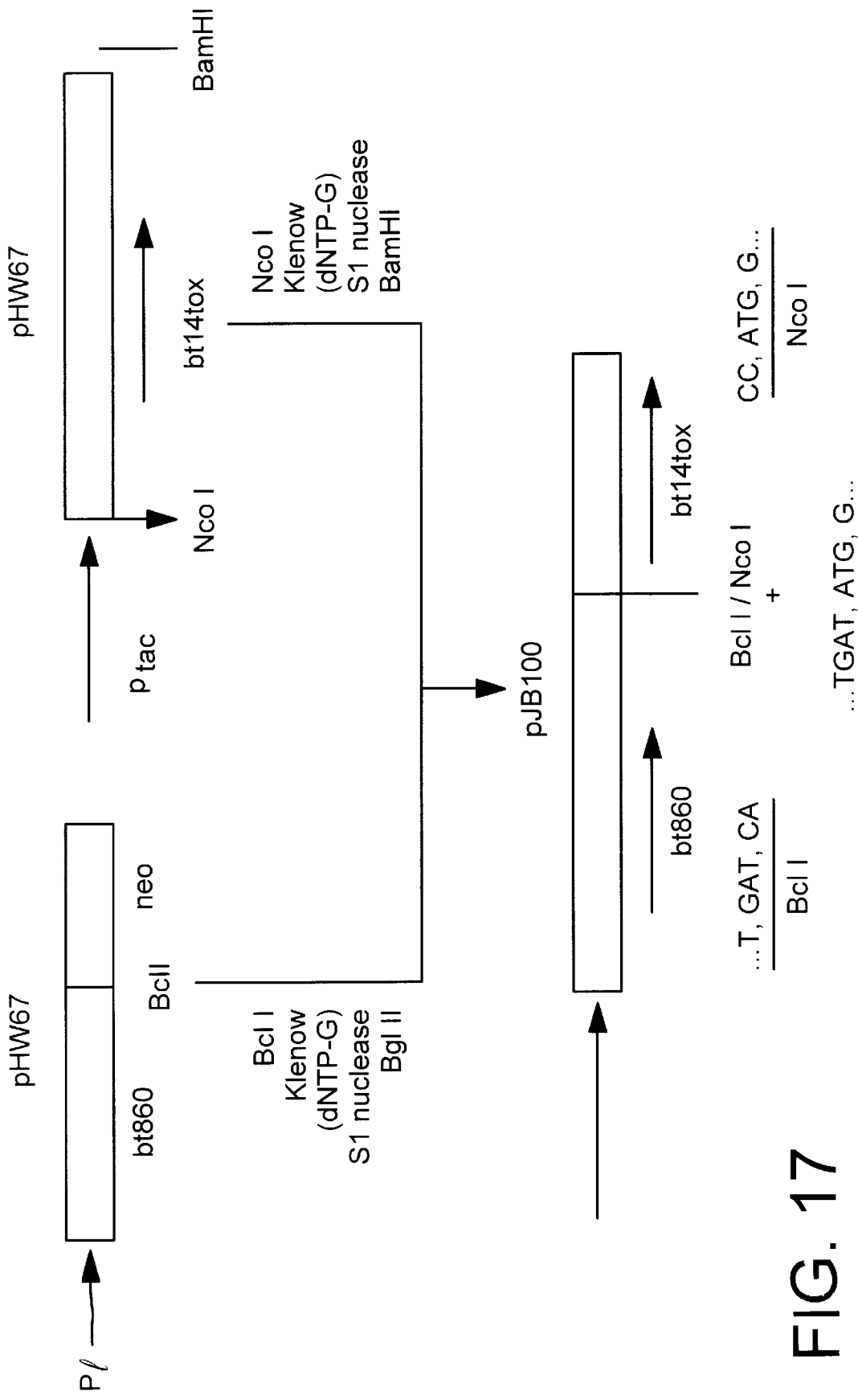
FIG. 17 depicts construction of the hybrid bt2–bt14 gene composed of a C-terminal bt2 gene fragment (bt860) encoding the toxic core of the Bt2 protoxin in frame with a C-terminal truncated bt14 gene fragment encoding the toxic core of the Bt14 protoxin.

The simultaneous co-expression of the bt2 and bt14 genes is obtained by constructing a hybrid gene composed of a truncated bt14 gene fragment fused to a truncated bt2 gene fragment. Schematically shown in FIG. 17 is the construction of such a hybrid bt2-bt14 gene with a C-terminal bt2 gene fragment (bt860) encoding the toxic core of the Bt2 protoxin in frame with a C-terminal truncated bt14 gene fragment encoding the toxic core of the Bt14 protoxin. The BclI site in the bt2 gene, localized downstream of the trypsin cleavage site, is fused in frame with the NcoI site introduced at the N-terminal end of the truncated bt14 gene fragment. To this end, the plasmids pLBKm860 (EP 0193259) and pHW67 are used. pLBKm860 contains a hybrid bt2-neo gene under control of the lambda $P_L$ promoter. The bt2 gene moiety in the hybrid gene is a C-terminal truncated bt2 gene fragment, indicated as bt860 (in FIG. 17) (see also Vaeck et al, 1987). The construction of pHW67 is described in FIG. 16. pHW67 contains a C-terminal truncated bt14 gene fragment (bt14tox) with a NcoI site at the ATG initiation codon, a translation stop codon located at the BclI site of the intact bt14 gene and a BamHI site downstream of the whole gene fragment. To fuse both gene fragments in the proper reading frame, the BclI and NcoI ends of the respective plasmids are treated with Klenow DNA polymerase and S1 nuclease as indicated in FIG. 16. The resulting plasmid pJB100 contains the hybrid bt860-bt14tox gene under control of the lambda $P_L$ promoter and directs the expression in *E. coli* of a fusion protein with the expected mobility on SDS-PAGE.

Crude extracts of the *E. coli* strain show the toxicity of the fusion protein, expressed by the strain, against *P. brassicae*. It has also been confirmed by N-terminal amino acid sequence analyses of the fusion protein produced by the *E. coli* strain that the N-terminal amino acids from the Bt14 protoxin are processed upon activation. The bt2-bt14 hybrid gene product has thus two potential protease cleavage sites.

Subsequently, this hybrid gene is inserted into a vector for plant transformations and placed under control of a suitable promoter and transferred to the genome of brassica (EP 0193259) where both the bt2 and bt14 genes are expressed in insect toxicity tests.

TABLE 2

| Gene | B strain | Host range | amino acids encoded | predicted MW(kDa) of encoded aminoacids | Disclosure of nucleotide sequence |
|---|---|---|---|---|---|
| bt3 | HD-1 kurstaki | L | 1176 | 133.2 | Schnepf et al., 1985 |
| bt2 | berliner 1715 | L | 1155 | 131 | Höfte et al., 1986 |
| bt73 | HD-73 | L | 1178 | 133.3 | Adang et al, 1985 |
| bt14 | entomocidus HD-110 | L | 1207 | 138 | Brizzard and Whiteley, 1988 |
| bt15 | entomocidus HD-110 | L | 1189 | 134.8 | FIG. 14 |
| bt4 | HD-68 aizawai | L | 1165 | 132.5 | FIG. 13 |
| bt18 | darmstadiensis HD-116 | L | 1171 | 133 | EP appln. 88402241.9 |
| bt13 | BtS1, DSM4288 22/10/87 | C | 644 | 73.1 | EP appln. 88402115.5 |
| bt21 | BLPGSI208, DSM 5131, 19/1/89 | C | 651 | 74.2 | EP appln. 89400428.2 |
| bt22 | BtPGSI245, DSM 5132, 19/1/89 | C | 1138 | 129 | EP appln. 8940028.2 |
| P2 | HD-263 | L/D | 633 | 70.9 | Donovan et al, 1988 |
| Cry B2 | HD-1 | L | 633 | 70.8 | Widner and Whiteley, 1989 |

REFERENCES

Adang M., Staver M., Rocheleau T., Leighton J., Barker R. and Thompson D. (1985), Gene 36, 289–300.

Angenon et al (1989), Molecular and Cellular Biology 9, 5676–5684.

Barton K., Whiteley H. and Yang N.-S. (1987), Plant Physiol. 85, 1103–1109.

Bernard H., Remaut E., Hersfield M., Das H., Helinski D., Yanofski C. and Franklin N. (1979), Gene 5, 59–76.

Bell R. and Joachim F. (1976), Ann. Entomol. Soc. Am. 69, 365–373.

Botterman J. and Zabeau M. (1987), DNA 6, 583–591.

Bradford M. (1976), Anal. Biochem. 72, 248–254.

Brattsten L., Holyoke C., Leeper J. and Raffa K. (1986), Science 231, 1255–1260.

Brizzard B. and Whiteley H. (1988), Nucleic Acids Research 16, 4168–4169.

Deblaere R., Reynaerts A., Höfte H., Hernalsteens J-P, Leemans J. and Van Montagu M. (1988), Methods in Enzymol. 153, 277–292.

De Block M., Botterman J., Vandewiele M., Dockx J., Thoen, Gossele V., Rao Movva, Thompson C., Van Montagu M. and Leemans J. (1987), EMBO J. 6, 2513–2518.

De Block et al (1989), Plant Physiology 91, 694–701.

De Boer H., Comstock L. and Vasser M. (1983), Proc. Natl. Acad. Sci. USA 80, 21–25.

de Framond A., Back E., Chilton W., Kayes L. and Chilton M-D (1986), Mol. Gen. Genet. 202, 125–131.

De Greve et al (1982), J. Mol. Appl. Genet. 1 (6), 499–511.

De La Pena and Schell (1986), Nature 325, 274–276.

Delauney A., Tabaeizadeh Z. and Verma D. (1988), Proc. Natl. Acad. Sci. USA 85, 4300–4304.

Depicker A., Herman L., Jacobs A., Schell J. and Van Montagu M. (1985), Mol. Gen. Genet. 201, 477–484.

Donovan W., Dankoscik C. and Gilbert W. (1988), J. Bacteriol. 170, 4732–4738.

Dulmage H. T and cooperators (1981), In Microbial control of pests and plant diseases 1970–1980 (Ed. H. D. Burges), Academic Press, 193–222.

Finney D. (1962), Probit Analysis (University Press, Cambridge), pp. 50–80.

Fischhoff D., Bowdish K., Perlak F., Marrone P., McCormick S., Niedermeyer J., Dean D., Kuzano-Kretzmer K., Mayer E., Rochester D., Rogers S. and Fraley R. (1987), Bio/Technology 5, 807–812.

Franck, Guilley, Jonard, Richards and Hirth (1980), Cell 21, 285–294.

French B., Maul H. and Maul G. (1986), Anal. Biochem. 156, 417–423.

Fuller F. (1982), Gene 19, 43–54.

Gardner, Howarth, Hahn, Brown-Luedi, Shepard and Messing, Nucl. Acids Res. 9, 2871–2887.

Goldberg L. and Margalit J. (1977), Mosq. News 37, 355–358.

Goldman I., Arnold J. and Carlton B. (1986), J. Invert. Pathol. 47, 317–324.

Gould F. (1988), Bioscience 38, 26–33.

Haider M., Knowles B. and Ellar D. (1986), Eur. J. Biochem. 156, 531–540.

Herrera-Estrella (1983) Nature 303, 209–213.

Hofmann C., Lüthy P., Hutter R. and Pliska V. (1988a), Eur. J. Biochem. 173, 85–91.

Hofmann C., Vanderbruggen H., Höfte H., Van Rie J., Jansens S. and Van Mellaert H. (1988b), Proc. Natl. Acad. Sci. USA 85, 7844–7848.

Höfte H., Van Rie J., Jansens S., Van Houtven A., Verbruggen H. and Vaeck M. (1988), Appl. Environ. Microbiol. 54, 2010–2017.

Höfte H., De Greve H., Seurinck J., Jansens S., Mahillon J., Ampe C., Vanderkerkhove J., Vanderbruggen H., Van Montagu M., Zabeau M. and Vaeck M. (1987), Eur. J. Biochem. 161, 273–280.

Höfte H. and Whiteley H. R. (1989), Microbiological Reviews 53, 242–255.

Hsiung H. and Becker G. (1988), Biotech. and Genetic Engin. Rev. 6, 43–65.

Hull and Howell (1987), Virology 86, 482–493.

Hunter W. and Greenwood F. (1962), Nature 194, 495–496.

Kozak M. (1987), Mol. Cell. Biol. 7, 3438–3445.

Krebbers E., Herdies L., De Clercq A., Seurinck J., Leemans J., Van Damme J., Segura M.,Gheysen G., Van Montagu M. and Vandekerckhove J. (1988), Plant Physiol. 87, 859–866.

Knowles B. and Ellar D. (1986), J. Cell. Sci 83, 89–101.

Krieg A., Huger A., Langenbruch G. and Schnetter W. (1983), Z. Ang. Ent. 96, 500–508.

Krieg A. and Langenbruch G. (1981), In Microbial control of pests and plant diseases 1970–1980 (Ed. H. D. Burges), Academic Press, 837–986.

Kirsch K. and Schmutterer H. (1988), J. Appl. Ent. 105, 249–255.

Kronstad J., Schnepf H. and Whiteley H. (1983), J. Bacteriol. 154, 419–428.

Mahillon J. and Delcour J. (1984), J. Microbiol. Methods 3, 69–73.

Maxam A. and Gilbert W. (1980), Methods in Enzymol. 65, 499–560.

McGaughey W. (1985), Science 229, 193–195.

McGaughey W. and Beeman R. (1988), J. Econ. Entomol. 81, 28–33.

Munson P. and Rodbard D. (1980), Anal. Biochem. 107, 220–239.

Pazkowski and cooperators (1984), EMBO J 3, 2717–2722.

Peleman J., Boerjan W., Engler G., Seurinck J., Botterman J., Alliote T., Van Montagu M. and Inze D. (1989), The Plant Cell 1, 81–93.

Remaut E., Stanssen P. and Fiers W. (1981), Gene 15, 81–93.

Rocha-Sosa et al (1989) EMBO J. 8, 23–29.

Sandler S., Stayton M., Townsend J., Ralstan M., Bedbrook J. and Dunsmuir P. (1988), Plant Mol. Biol. 11, 301–310.

Scatchard G. (1949), Ann. N.Y. Acad. Sci. 51, 660–672.

Schocher R., Shillito R., Saul M., Pazkowski J. and Potrykus I. (1986) Bio/technology 4, 1093–1096.

Shields (1987), Nature 328, 12–13.

Schnepf H., Wong H. and Whiteley H. (1985), J. Biol. Chem. 260, 6264–6272.

Stanssens P., Remaut E. and Fiers W. (1985), Gene 36, 211–223.

Stanssens P., McKeown Y., Friedrich K. and Fritz H. (1987): "Oligo-nucleotide directed construction of mutations by the gapped duplex DNA method using the pMa/c plasmid vectors", published in the Collection of Experimental Procedures distributed at the EMBO course entitled "Directed mutagenesis and protein engineering" in July 1987 at the Max Planck Institut für Biochemie, Martinsried, FRG.

Stone T., Sims S. and Marrone P. (1989), J. Invert. Pathol. 53, 228–234.

Vaeck M., Reynaerts A., Höfte H., Jansens S., De Beukeleer M., Dean C. Zabeau M., Van Montagu M. and Leemans J. (1987), Nature 327, 33–37.

Voller, Bidwell and Barlett (1976), In: Manual of Clinical Immunology (Eds. Rose and Friedman), pp. 506–512, American Society of Microbiology, Washington Velten J., Velten L., Hain R. and Schell J. (1984), EMBO J. 3, 2723–2730.

Velten J. and Schell J. (1985), Nucl. Acids Res. 13, 6981–6998.

Widner W. and Whiteley H. (1989), J. Bacteriol. 171, 965–974.

Wolfersberger M., Lüthy P., Maurer A., Parenti P., Sacchi V., Giordana B. and Hanozet G. (1987), Comp. Biochem. Physiol. 86, 301–308.

Yanish-Perron C., Veiera J. and Messing J. (1985), Gene 33, 103–119.

We claim:

1. A plant, comprising stably inserted into the genome of its cells, at least two DNA sequences each encoding a different *Bacillus thurningiensis* (Bt) insecticidal crystal protein (ICP) or an insecticidal portion thereof, toxic to the same insect species, wherein the encoded Bt ICPs or the insecticidal portions thereof bind non-competitively to the brush border membrane of the midgut epithelial cells of said same insect species; and wherein said Bt ICPs or the insecticidal portions thereof are produced in said plant.

2. The plant of claim 1, wherein said at least two DNA sequences are under the control of the same promoter or different promoters directing gene expression in a cell of said plant.

3. The plant of claim 2, wherein a DNA fragment, encoding a protease-sensitive or protease-cleavable amino acid sequence, is in said same transcriptional unit as said at least two DNA sequences and intercalated between said DNA sequences.

4. The plant of claim 1, wherein said at least two DNA sequences encode insecticidal proteins having activity against Lepidoptera species.

5. The plant of claim 1, wherein said at least two DNA sequences encode insecticidal proteins having activity against Coleoptera species.

6. The plant of claim 4, wherein said insecticidal proteins are selected from the group consisting of: Bt2, Bt4, Bt15, and Bt18.

7. The plant of claim 2, wherein said promoters are selected from the group consisting of: a constitutive promoter, a nopaline synthase promoter, an octopine synthase promoter, a wound-inducible promoter, a promoter which directs gene expression selectively in plant tissue having photosynthetic activity, a promoter inducible by temperature or chemical factors, a tissue-specific promoter, a 35S promoter, a TR1' promoter, a TR2' promoter, an SSU promoter, a tuber-specific promoter, a stem-specific promoter, and a seed-specific promoter.

8. A seed of the plant of claim 1, comprising said at least two DNA sequences.

9. The plant of claim 1, wherein said plant also comprises a marker gene selected from the group consisting of: an herbicide resistance gene, a gene encoding a modified target enzyme for an herbicide having a lower affinity for the herbicide, an antibiotic resistance gene, an sfr gene, an sfrv gene, a gene encoding a modified 5-EPSP as a target for glyphosate, a gene encoding a modified glutamine synthetase as a target for a GS inhibitor, and a gene encoding NPTII.

10. The plant of claim 1, wherein said at least two DNA sequences are naturally-occurring or synthetic.

11. The plant of claim 1, wherein expression of said DNA sequences is simultaneous in the plant.

12. The plant of claim 1, wherein said ICPs or the insecticidal portions thereof are not naturally-occurring.

13. The plant of claim 12, wherein at least one of the ICPs or the insecticidal portion thereof is a chimaeric toxin formed by the combination of two variable regions of two different ICPs.

14. The plant of claim 1, wherein said ICPs or the insecticidal portions thereof are selected from the group consisting of: Bt2, Bt18, Bt73, Bt15, Bt14, Bt4, Bt13, Bt21, Bt22 ICPs, and the insecticidal portions thereof.

15. The plant of claim 1, wherein said DNA sequences encode a Bt2 ICP or an insecticidal portion thereof, and a Bt14 ICP or an insecticidal portion thereof.

16. The plant of claim 1 which is a Brassica, tomato, potato, tobacco, cotton or lettuce plant.

17. A plant, comprising stably inserted into the genome of its cells, at least two DNA sequences each encoding a different *Bacillus thurningiensis* (Bt) insecticidal crystal protein (ICP) or an insecticidal portion thereof, toxic to the same insect species, wherein the encoded Bt ICPs or the insecticidal portions thereof do not bind competitively to the brush border membrane of the midgut epithelial cells of said same insect species; and wherein said Bt ICPs or the insecticidal portions thereof are produced in said plant.

* * * * *

UNITED STATES PATENT AND TRADEMARK OFFICE
CERTIFICATE OF CORRECTION

PATENT NO.  : 5,866,784

DATED  : February 2, 1999

INVENTOR(S) : Herman VAN MELLAERT et al.

It is certified that error appears in the above-identified patent and that said Letters Patent is hereby corrected as shown below:

On the cover page:

At [63], at the end of the last line, following "abandoned" please insert --, which is a continuation of PCT/EP90/00905, May 30, 1990--.

At column 1, line 8, following "abandoned" please insert --, which is a continuation of PCT/EP90/00905, May 30, 1990--.

At column 2, line 18, please delete "*quinguefasciatus*" and insert therefor --*quinquefasciatus*--.

At column 3, line 22, please delete "*thurinqiensis*" and insert therefor --*thuringiensis*--.

At column 13, line 16, please delete "they" and insert therefor --the--.

At column 14, line 27, please delete "*thurinqiensis*" and insert therefor --*thuringiensis*--.

At column 21, line 6, please delete "ICP's" and insert therefor --ICPs--.
At column 21, line 18, please delete "ICP's" and insert therefor --ICPs--.
At column 21, line 19, please delete "ICP's" and insert therefor --ICPs--.

At column 22, line 33, please delete "*Lepinotarsa*" and insert therefor "*Leptinotarsa*".
At column 22, line 34, please delete "*Lepinotarsa*" and insert therefor "*Leptinotarsa*".
At column 22, line 35, please delete "*Lepinotarsa*" and insert therefor "*Leptinotarsa*".

At column 25 line 32, please delete "(resistant *P. xylostella*)" and insert therefor --resistant *P. xylostella*--.

UNITED STATES PATENT AND TRADEMARK OFFICE
CERTIFICATE OF CORRECTION

PATENT NO. : 5,866,784
DATED : February 2, 1999
INVENTOR(S) : Herman VAN MELLAERT et al.

It is certified that error appears in the above-identified patent and that said Letters Patent is hereby corrected as shown below:

At column 28, line 57, please delete "BLPGSI208" and insert therefor --BtPGSI208--.

At column 30, line 53, please delete "Inze" and insert therefor --Inzé--.

At column 49, line 15, in claim 1, please delete "*thurningiensis*" and insert therefor --*thuringiensis*--.

At column 50, line 43, in claim 17, please delete "*thurningiensis*" and insert therefor --*thuringiensis*--.

Signed and Sealed this

Sixteenth Day of May, 2000

Attest:

Q. TODD DICKINSON

*Attesting Officer*     *Director of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CGGAGGTATT CCATGGAGGA AAATAATC                              2 8

( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CCTATTTGAA GCCATGGTAA CTCCTCCTTT TATG                      3 4

( 2 ) INFORMATION FOR SEQ ID NO:3:

( i ) SEQUENCE CHARACTERISTICS:
        ( A ) LENGTH: 3903 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 264..3761

( i x ) FEATURE:
        ( A ) NAME/KEY: 5'UTR
        ( B ) LOCATION: 1..263

( i x ) FEATURE:
        ( A ) NAME/KEY: 3'UTR
        ( B ) LOCATION: 3762..3903

( x i ) SEQUENCE DESCRIPTION: SEQ ID NO:3:

| | | | | | | | | | | |
|---|---|---|---|---|---|---|---|---|---|---|
| GGATCTGTTT | TAATATAAGG | GATTTGTGCC | CTTCTCGTTA | TATTCTTTTA | TTAGCCCCAA | | | | | 60 |
| AAACTAGTGC | AACTAAATAT | TTTTATAATT | ACACTGATTA | AATACTTTAT | TTTTGGGAGT | | | | | 120 |
| AAGATTTATG | CTGAAATGTA | ATAAAATTCG | TTCCATTTTC | TGTATTTTCT | CATAAAATGT | | | | | 180 |
| TTCATATGCT | TTAAATTGTA | GTAAAGAAAA | ACAGTACAAA | CTTAAAGGA | CTTTAGTAAT | | | | | 240 |
| TTAATAAAAA | AAGGGGATAG | TTT ATG GAA ATA AAT AAT CAA AAC CAA TGT | | | | | | | | 290 |

```
                             Met Glu Ile Asn Asn Gln Asn Gln Cys
                              1               5
```

| GTG | CCT | TAC | AAT | TGT | TTA | AGT | AAT | CCT | AAG | GAG | ATA | ATA | TTA | GGC | GAG | 338 |
|---|---|---|---|---|---|---|---|---|---|---|---|---|---|---|---|---|
| Val | Pro | Tyr | Asn | Cys | Leu | Ser | Asn | Pro | Lys | Glu | Ile | Ile | Leu | Gly | Glu | |
| 10 | | | | 15 | | | | | 20 | | | | | | 25 | |

| GAA | AGG | CTA | GAA | ACA | GGG | AAT | ACT | GTA | GCA | GAC | ATT | TCA | TTA | GGG | CTT | 386 |
|---|---|---|---|---|---|---|---|---|---|---|---|---|---|---|---|---|
| Glu | Arg | Leu | Glu | Thr | Gly | Asn | Thr | Val | Ala | Asp | Ile | Ser | Leu | Gly | Leu | |
| | | | | 30 | | | | | 35 | | | | | 40 | | |

| ATT | AAT | TTT | CTA | TAT | TCT | AAT | TTT | GTA | CCA | GGA | GGA | GGA | TTT | ATA | GTA | 434 |
|---|---|---|---|---|---|---|---|---|---|---|---|---|---|---|---|---|
| Ile | Asn | Phe | Leu | Tyr | Ser | Asn | Phe | Val | Pro | Gly | Gly | Gly | Phe | Ile | Val | |
| | | | | 45 | | | | 50 | | | | | 55 | | | |

| GGT | TTA | CTA | GAA | TTA | ATA | TGG | GGA | TTT | ATA | GGG | CCT | TCG | CAA | TGG | GAT | 482 |
|---|---|---|---|---|---|---|---|---|---|---|---|---|---|---|---|---|
| Gly | Leu | Leu | Glu | Leu | Ile | Trp | Gly | Phe | Ile | Gly | Pro | Ser | Gln | Trp | Asp | |
| | | 60 | | | | | 65 | | | | | 70 | | | | |

| ATT | TTT | TTA | GCT | CAA | ATT | GAG | CAA | TTG | ATT | AGT | CAA | AGA | ATA | GAA | GAA | 530 |
|---|---|---|---|---|---|---|---|---|---|---|---|---|---|---|---|---|
| Ile | Phe | Leu | Ala | Gln | Ile | Glu | Gln | Leu | Ile | Ser | Gln | Arg | Ile | Glu | Glu | |
| | 75 | | | | | 80 | | | | | 85 | | | | | |

| TTT | GCT | AGG | AAT | CAG | GCA | ATT | TCA | AGA | TTG | GAG | GGG | CTA | AGC | AAT | CTT | 578 |
|---|---|---|---|---|---|---|---|---|---|---|---|---|---|---|---|---|
| Phe | Ala | Arg | Asn | Gln | Ala | Ile | Ser | Arg | Leu | Glu | Gly | Leu | Ser | Asn | Leu | |
| 90 | | | | | 95 | | | | | 100 | | | | | 105 | |

| TAT | AAG | GTC | TAT | GTT | AGA | GCG | TTT | AGC | GAC | TGG | GAG | AAA | GAT | CCT | ACT | 626 |
|---|---|---|---|---|---|---|---|---|---|---|---|---|---|---|---|---|
| Tyr | Lys | Val | Tyr | Val | Arg | Ala | Phe | Ser | Asp | Trp | Glu | Lys | Asp | Pro | Thr | |
| | | | | 110 | | | | | 115 | | | | | 120 | | |

| AAT | CCT | GCT | TTA | AGG | GAA | GAA | ATG | CGT | ATA | CAA | TTT | AAT | GAC | ATG | AAT | 674 |
|---|---|---|---|---|---|---|---|---|---|---|---|---|---|---|---|---|
| Asn | Pro | Ala | Leu | Arg | Glu | Glu | Met | Arg | Ile | Gln | Phe | Asn | Asp | Met | Asn | |
| | | | 125 | | | | | 130 | | | | | 135 | | | |

| AGT | GCT | CTC | ATA | ACG | GCT | ATT | CCA | CTT | TTT | AGA | GTT | CAA | AAT | TAT | GAA | 722 |
|---|---|---|---|---|---|---|---|---|---|---|---|---|---|---|---|---|
| Ser | Ala | Leu | Ile | Thr | Ala | Ile | Pro | Leu | Phe | Arg | Val | Gln | Asn | Tyr | Glu | |
| | | | 140 | | | | | 145 | | | | | 150 | | | |

| GTT | GCT | CTT | TTA | TCT | GTA | TAT | GTT | CAA | GCC | GCA | AAC | TTA | CAT | TTA | TCT | 770 |
|---|---|---|---|---|---|---|---|---|---|---|---|---|---|---|---|---|
| Val | Ala | Leu | Leu | Ser | Val | Tyr | Val | Gln | Ala | Ala | Asn | Leu | His | Leu | Ser | |
| | 155 | | | | | 160 | | | | | 165 | | | | | |

| ATT | TTA | AGG | GAT | GTT | TCA | GTT | TTC | GGA | GAA | AGA | TGG | GGA | TAT | GAT | ACA | 818 |
|---|---|---|---|---|---|---|---|---|---|---|---|---|---|---|---|---|
| Ile | Leu | Arg | Asp | Val | Ser | Val | Phe | Gly | Glu | Arg | Trp | Gly | Tyr | Asp | Thr | |
| 170 | | | | | 175 | | | | | 180 | | | | | 185 | |

| GCG | ACT | ATC | AAT | AAT | CGC | TAT | AGT | GAT | CTG | ACT | AGC | CTT | ATT | CAT | GTT | 866 |
|---|---|---|---|---|---|---|---|---|---|---|---|---|---|---|---|---|
| Ala | Thr | Ile | Asn | Asn | Arg | Tyr | Ser | Asp | Leu | Thr | Ser | Leu | Ile | His | Val | |
| | | | | 190 | | | | | 195 | | | | | 200 | | |

| TAT | ACT | AAC | CAT | TGT | GTG | GAT | ACG | TAT | AAT | CAG | GGA | TTA | AGG | CGT | TTG | 914 |
|---|---|---|---|---|---|---|---|---|---|---|---|---|---|---|---|---|
| Tyr | Thr | Asn | His | Cys | Val | Asp | Thr | Tyr | Asn | Gln | Gly | Leu | Arg | Arg | Leu | |
| | | | 205 | | | | | 210 | | | | | 215 | | | |

| GAA | GGT | CGT | TTT | CTT | AGC | GAT | TGG | ATT | GTA | TAT | AAT | CGT | TTC | CGG | AGA | 962 |
|---|---|---|---|---|---|---|---|---|---|---|---|---|---|---|---|---|
| Glu | Gly | Arg | Phe | Leu | Ser | Asp | Trp | Ile | Val | Tyr | Asn | Arg | Phe | Arg | Arg | |
| | | 220 | | | | | 225 | | | | | 230 | | | | |

| CAA | TTG | ACA | ATT | TCA | GTA | TTA | GAT | ATT | GTT | GCG | TTT | TTT | CCA | AAT | TAT | 1010 |
|---|---|---|---|---|---|---|---|---|---|---|---|---|---|---|---|---|
| Gln | Leu | Thr | Ile | Ser | Val | Leu | Asp | Ile | Val | Ala | Phe | Phe | Pro | Asn | Tyr | |
| 235 | | | | | 240 | | | | | 245 | | | | | | |

| GAT | ATT | AGA | ACA | TAT | CCA | ATT | CAA | ACA | GCT | ACT | CAG | CTA | ACG | AGG | GAA | 1058 |
|---|---|---|---|---|---|---|---|---|---|---|---|---|---|---|---|---|
| Asp | Ile | Arg | Thr | Tyr | Pro | Ile | Gln | Thr | Ala | Thr | Gln | Leu | Thr | Arg | Glu | |
| 250 | | | | | 255 | | | | | 260 | | | | | 265 | |

| GTC | TAT | CTG | GAT | TTA | CCT | TTT | ATT | AAT | GAA | AAT | CTT | TCT | CCT | GCA | GCA | 1106 |

|     |     |     |     |     |     |     |     |     |     |     |     |     |     |     |     |
| --- | --- | --- | --- | --- | --- | --- | --- | --- | --- | --- | --- | --- | --- | --- | --- |
| Val | Tyr | Leu | Asp | Leu | Pro | Phe | Ile | Asn | Glu | Asn | Leu | Ser | Pro | Ala | Ala |
|     |     |     |     | 270 |     |     |     | 275 |     |     |     |     | 280 |     |     |

| AGC | TAT | CCA | ACC | TTT | TCA | GCT | GCT | GAA | AGT | GCT | ATA | ATT | AGA | AGT | CCT | 1154 |
| --- | --- | --- | --- | --- | --- | --- | --- | --- | --- | --- | --- | --- | --- | --- | --- | --- |
| Ser | Tyr | Pro | Thr | Phe | Ser | Ala | Ala | Glu | Ser | Ala | Ile | Ile | Arg | Ser | Pro |     |
|     |     |     | 285 |     |     |     |     | 290 |     |     |     |     | 295 |     |     |     |

| CAT | TTA | GTA | GAC | TTT | TTA | AAT | AGC | TTT | ACC | ATT | TAT | ACA | GAT | AGT | CTG | 1202 |
| --- | --- | --- | --- | --- | --- | --- | --- | --- | --- | --- | --- | --- | --- | --- | --- | --- |
| His | Leu | Val | Asp | Phe | Leu | Asn | Ser | Phe | Thr | Ile | Tyr | Thr | Asp | Ser | Leu |     |
|     |     | 300 |     |     |     |     | 305 |     |     |     |     | 310 |     |     |     |     |

| GCA | CGT | TAT | GCA | TAT | TGG | GGA | GGG | CAC | TTG | GTA | AAT | TCT | TTC | CGC | ACA | 1250 |
| --- | --- | --- | --- | --- | --- | --- | --- | --- | --- | --- | --- | --- | --- | --- | --- | --- |
| Ala | Arg | Tyr | Ala | Tyr | Trp | Gly | Gly | His | Leu | Val | Asn | Ser | Phe | Arg | Thr |     |
|     | 315 |     |     |     |     | 320 |     |     |     |     | 325 |     |     |     |     |     |

| GGA | ACC | ACT | ACT | AAT | TTG | ATA | AGA | TCC | CCT | TTA | TAT | GGA | AGG | GAA | GGA | 1298 |
| --- | --- | --- | --- | --- | --- | --- | --- | --- | --- | --- | --- | --- | --- | --- | --- | --- |
| Gly | Thr | Thr | Thr | Asn | Leu | Ile | Arg | Ser | Pro | Leu | Tyr | Gly | Arg | Glu | Gly |     |
| 330 |     |     |     |     | 335 |     |     |     |     | 340 |     |     |     |     | 345 |     |

| AAT | ACA | GAG | CGC | CCC | GTA | ACT | ATT | ACC | GCA | TCA | CCT | AGC | GTA | CCA | ATA | 1346 |
| --- | --- | --- | --- | --- | --- | --- | --- | --- | --- | --- | --- | --- | --- | --- | --- | --- |
| Asn | Thr | Glu | Arg | Pro | Val | Thr | Ile | Thr | Ala | Ser | Pro | Ser | Val | Pro | Ile |     |
|     |     |     |     | 350 |     |     |     |     | 355 |     |     |     |     | 360 |     |     |

| TTT | AGA | ACA | CTT | TCA | TAT | ATT | ACA | GGC | CTT | GAC | AAT | TCA | AAT | CCT | GTA | 1394 |
| --- | --- | --- | --- | --- | --- | --- | --- | --- | --- | --- | --- | --- | --- | --- | --- | --- |
| Phe | Arg | Thr | Leu | Ser | Tyr | Ile | Thr | Gly | Leu | Asp | Asn | Ser | Asn | Pro | Val |     |
|     |     |     | 365 |     |     |     |     | 370 |     |     |     |     | 375 |     |     |     |

| GCT | GGA | ATC | GAG | GGA | GTG | GAA | TTC | CAA | AAT | ACT | ATA | AGT | AGA | AGT | ATC | 1442 |
| --- | --- | --- | --- | --- | --- | --- | --- | --- | --- | --- | --- | --- | --- | --- | --- | --- |
| Ala | Gly | Ile | Glu | Gly | Val | Glu | Phe | Gln | Asn | Thr | Ile | Ser | Arg | Ser | Ile |     |
|     |     |     | 380 |     |     |     |     | 385 |     |     |     |     | 390 |     |     |     |

| TAT | CGT | AAA | AGC | GGT | CCA | ATA | GAT | TCT | TTT | AGT | GAA | TTA | CCA | CCT | CAA | 1490 |
| --- | --- | --- | --- | --- | --- | --- | --- | --- | --- | --- | --- | --- | --- | --- | --- | --- |
| Tyr | Arg | Lys | Ser | Gly | Pro | Ile | Asp | Ser | Phe | Ser | Glu | Leu | Pro | Pro | Gln |     |
|     | 395 |     |     |     |     | 400 |     |     |     |     | 405 |     |     |     |     |     |

| GAT | GCC | AGC | GTA | TCT | CCT | GCA | ATT | GGG | TAT | AGT | CAC | CGT | TTA | TGC | CAT | 1538 |
| --- | --- | --- | --- | --- | --- | --- | --- | --- | --- | --- | --- | --- | --- | --- | --- | --- |
| Asp | Ala | Ser | Val | Ser | Pro | Ala | Ile | Gly | Tyr | Ser | His | Arg | Leu | Cys | His |     |
| 410 |     |     |     |     | 415 |     |     |     |     | 420 |     |     |     |     | 425 |     |

| GCA | ACA | TTT | TTA | GAA | CGG | ATT | AGT | GGA | CCA | AGA | ATA | GCA | GGC | ACC | GTA | 1586 |
| --- | --- | --- | --- | --- | --- | --- | --- | --- | --- | --- | --- | --- | --- | --- | --- | --- |
| Ala | Thr | Phe | Leu | Glu | Arg | Ile | Ser | Gly | Pro | Arg | Ile | Ala | Gly | Thr | Val |     |
|     |     |     |     | 430 |     |     |     |     | 435 |     |     |     |     | 440 |     |     |

| TTT | TCT | TGG | ACA | CAC | CGT | AGT | GCC | AGC | CCT | ACT | AAT | GAA | GTA | AGT | CCA | 1634 |
| --- | --- | --- | --- | --- | --- | --- | --- | --- | --- | --- | --- | --- | --- | --- | --- | --- |
| Phe | Ser | Trp | Thr | His | Arg | Ser | Ala | Ser | Pro | Thr | Asn | Glu | Val | Ser | Pro |     |
|     |     |     | 445 |     |     |     |     | 450 |     |     |     |     | 455 |     |     |     |

| TCT | AGA | ATT | ACA | CAA | ATT | CCA | TGG | GTA | AAG | GCG | CAT | ACT | CTT | GCA | TCT | 1682 |
| --- | --- | --- | --- | --- | --- | --- | --- | --- | --- | --- | --- | --- | --- | --- | --- | --- |
| Ser | Arg | Ile | Thr | Gln | Ile | Pro | Trp | Val | Lys | Ala | His | Thr | Leu | Ala | Ser |     |
|     |     |     | 460 |     |     |     |     | 465 |     |     |     |     | 470 |     |     |     |

| GGT | GCC | TCC | GTC | ATT | AAA | GGT | CCT | GGA | TTT | ACA | GGT | GGA | GAT | ATT | CTG | 1730 |
| --- | --- | --- | --- | --- | --- | --- | --- | --- | --- | --- | --- | --- | --- | --- | --- | --- |
| Gly | Ala | Ser | Val | Ile | Lys | Gly | Pro | Gly | Phe | Thr | Gly | Gly | Asp | Ile | Leu |     |
|     | 475 |     |     |     |     | 480 |     |     |     |     | 485 |     |     |     |     |     |

| ACT | AGG | AAT | AGT | ATG | GGC | GAG | CTG | GGG | ACC | TTA | CGA | GTA | ACC | TTC | ACA | 1778 |
| --- | --- | --- | --- | --- | --- | --- | --- | --- | --- | --- | --- | --- | --- | --- | --- | --- |
| Thr | Arg | Asn | Ser | Met | Gly | Glu | Leu | Gly | Thr | Leu | Arg | Val | Thr | Phe | Thr |     |
| 490 |     |     |     |     | 495 |     |     |     |     | 500 |     |     |     |     | 505 |     |

| GGA | AGA | TTA | CCA | CAA | AGT | TAT | TAT | ATA | CGT | TTC | CGT | TAT | GCT | TCG | GTA | 1826 |
| --- | --- | --- | --- | --- | --- | --- | --- | --- | --- | --- | --- | --- | --- | --- | --- | --- |
| Gly | Arg | Leu | Pro | Gln | Ser | Tyr | Tyr | Ile | Arg | Phe | Arg | Tyr | Ala | Ser | Val |     |
|     |     |     |     | 510 |     |     |     |     | 515 |     |     |     |     | 520 |     |     |

| GCA | AAT | AGG | AGT | GGT | ACA | TTT | AGA | TAT | TCA | CAG | CCA | CCT | TCG | TAT | GGA | 1874 |
| --- | --- | --- | --- | --- | --- | --- | --- | --- | --- | --- | --- | --- | --- | --- | --- | --- |
| Ala | Asn | Arg | Ser | Gly | Thr | Phe | Arg | Tyr | Ser | Gln | Pro | Pro | Ser | Tyr | Gly |     |
|     |     |     | 525 |     |     |     |     | 530 |     |     |     |     | 535 |     |     |     |

| ATT | TCA | TTT | CCA | AAA | ACT | ATG | GAC | GCA | GGT | GAA | CCA | CTA | ACA | TCT | CGT | 1922 |
| --- | --- | --- | --- | --- | --- | --- | --- | --- | --- | --- | --- | --- | --- | --- | --- | --- |
| Ile | Ser | Phe | Pro | Lys | Thr | Met | Asp | Ala | Gly | Glu | Pro | Leu | Thr | Ser | Arg |     |
|     |     | 540 |     |     |     |     | 545 |     |     |     |     | 550 |     |     |     |     |

| TCG | TTC | GCT | CAT | ACA | ACA | CTC | TTC | ACT | CCA | ATA | ACC | TTT | TCA | CGA | GCT | 1970 |
| --- | --- | --- | --- | --- | --- | --- | --- | --- | --- | --- | --- | --- | --- | --- | --- | --- |
| Ser | Phe | Ala | His | Thr | Thr | Leu | Phe | Thr | Pro | Ile | Thr | Phe | Ser | Arg | Ala |     |
|     | 555 |     |     |     |     | 560 |     |     |     |     | 565 |     |     |     |     |     |

| CAA | GAA | GAA | TTT | GAT | CTA | TAC | ATC | CAA | TCG | GGT | GTT | TAT | ATA | GAT | CGA | 2018 |
| --- | --- | --- | --- | --- | --- | --- | --- | --- | --- | --- | --- | --- | --- | --- | --- | --- |
| Gln | Glu | Glu | Phe | Asp | Leu | Tyr | Ile | Gln | Ser | Gly | Val | Tyr | Ile | Asp | Arg |     |
| 570 |     |     |     |     | 575 |     |     |     |     | 580 |     |     |     |     | 585 |     |

| ATT | GAA | TTT | ATA | CCG | GTT | ACT | GCA | ACA | TTT | GAG | GCA | GAA | TAT | GAT | TTA | 2066 |
| --- | --- | --- | --- | --- | --- | --- | --- | --- | --- | --- | --- | --- | --- | --- | --- | --- |

```
Ile Glu Phe Ile Pro Val Thr Ala Thr Phe Glu Ala Glu Tyr Asp Leu
            590                 595                 600

GAA AGA GCG CAA AAG GTG GTG AAT GCC CTG TTT ACG TCT ACA AAC CAA      2114
Glu Arg Ala Gln Lys Val Val Asn Ala Leu Phe Thr Ser Thr Asn Gln
            605                 610                 615

CTA GGG CTA AAA ACA GAT GTG ACG GAT TAT CAT ATT GAT CAG GTA TCC      2162
Leu Gly Leu Lys Thr Asp Val Thr Asp Tyr His Ile Asp Gln Val Ser
            620                 625                 630

AAT CTA GTT GCG TGT TTA TCG GAT GAA TTT TGT CTG GAT GAA AAG AGA      2210
Asn Leu Val Ala Cys Leu Ser Asp Glu Phe Cys Leu Asp Glu Lys Arg
            635                 640                 645

GAA TTG TCC GAG AAA GTT AAA CAT GCA AAG CGA CTC AGT GAT GAG CGG      2258
Glu Leu Ser Glu Lys Val Lys His Ala Lys Arg Leu Ser Asp Glu Arg
650                 655                 660                 665

AAT TTA CTT CAA GAT CCA AAC TTC AGA GGG ATC AAT AGG CAA CCA GAC      2306
Asn Leu Leu Gln Asp Pro Asn Phe Arg Gly Ile Asn Arg Gln Pro Asp
            670                 675                 680

CGT GGC TGG AGA GGA AGT ACG GAT ATT ACT ATC CAA GGA GGA GAT GAC      2354
Arg Gly Trp Arg Gly Ser Thr Asp Ile Thr Ile Gln Gly Gly Asp Asp
            685                 690                 695

GTA TTC AAA GAG AAT TAC GTT ACG CTA CCG GGT ACC TTT GAT GAG TGC      2402
Val Phe Lys Glu Asn Tyr Val Thr Leu Pro Gly Thr Phe Asp Glu Cys
            700                 705                 710

TAT CCA ACG TAT TTA TAT CAA AAA ATA GAT GAG TCG AAA TTA AAA GCC      2450
Tyr Pro Thr Tyr Leu Tyr Gln Lys Ile Asp Glu Ser Lys Leu Lys Ala
            715                 720                 725

TAT ACC CGT TAT CAA TTA AGA GGG TAT ATC GAA GAT AGT CAA GAC TTA      2498
Tyr Thr Arg Tyr Gln Leu Arg Gly Tyr Ile Glu Asp Ser Gln Asp Leu
730                 735                 740                 745

GAA ATC TAT TTA ATT CGT TAC AAT GCA AAA CAC GAA ATA GTA AAT GTA      2546
Glu Ile Tyr Leu Ile Arg Tyr Asn Ala Lys His Glu Ile Val Asn Val
            750                 755                 760

CCA GGT ACA GGA AGT TTA TGG CCT CTT TCT GTA GAA AAT CAA ATT GGA      2594
Pro Gly Thr Gly Ser Leu Trp Pro Leu Ser Val Glu Asn Gln Ile Gly
            765                 770                 775

CCT TGT GGA GAA CCG AAT CGA TGC GCG CCA CAC CTT GAA TGG AAT CCT      2642
Pro Cys Gly Glu Pro Asn Arg Cys Ala Pro His Leu Glu Trp Asn Pro
            780                 785                 790

GAT TTA CAC TGT TCC TGC AGA GAC GGG GAA AAA TGT GCA CAT CAT TCT      2690
Asp Leu His Cys Ser Cys Arg Asp Gly Glu Lys Cys Ala His His Ser
795                 800                 805

CAT CAT TTC TCT TTG GAC ATT GAT GTT GGA TGT ACA GAC TTA AAT GAG      2738
His His Phe Ser Leu Asp Ile Asp Val Gly Cys Thr Asp Leu Asn Glu
810                 815                 820                 825

GAC TTA GGT GTA TGG GTG ATA TTC AAG ATT AAG ACG CAA GAT GGC CAC      2786
Asp Leu Gly Val Trp Val Ile Phe Lys Ile Lys Thr Gln Asp Gly His
            830                 835                 840

GCA CGA CTA GGG AAT CTA GAG TTT CTC GAA GAG AAA CCA TTA TTA GGA      2834
Ala Arg Leu Gly Asn Leu Glu Phe Leu Glu Glu Lys Pro Leu Leu Gly
            845                 850                 855

GAA GCA CTA GCT CGT GTG AAA AGA GCG GAG AAA AAA TGG AGA GAC AAA      2882
Glu Ala Leu Ala Arg Val Lys Arg Ala Glu Lys Lys Trp Arg Asp Lys
            860                 865                 870

CGC GAA ACA TTA CAA TTG GAA ACA ACT ATC GTT TAT AAA GAG GCA AAA      2930
Arg Glu Thr Leu Gln Leu Glu Thr Thr Ile Val Tyr Lys Glu Ala Lys
            875                 880                 885

GAA TCT GTA GAT GCT TTA TTT GTA AAC TCT CAA TAT GAT AGA TTA CAA      2978
Glu Ser Val Asp Ala Leu Phe Val Asn Ser Gln Tyr Asp Arg Leu Gln
890                 895                 900                 905

GCG GAT ACG AAC ATC GCG ATG ATT CAT GCG GCA GAT AAA CGC GTT CAT      3026
```

-continued

```
Ala Asp Thr Asn Ile Ala Met Ile His Ala Ala Asp Lys Arg Val His
                910                 915                 920

AGA ATT CGA GAA GCG TAT CTG CCG GAG CTG TCT GTG ATT CCG GGT GTC       3074
Arg Ile Arg Glu Ala Tyr Leu Pro Glu Leu Ser Val Ile Pro Gly Val
                925                 930                 935

AAT GCG GCT ATT TTT GAA GAA TTA GAA GAG CGT ATT TTC ACT GCA TTT       3122
Asn Ala Ala Ile Phe Glu Glu Leu Glu Glu Arg Ile Phe Thr Ala Phe
                940                 945                 950

TCC CTA TAT GAT GCG AGA AAT ATT ATT AAA AAT GGC GAT TTC AAT AAT       3170
Ser Leu Tyr Asp Ala Arg Asn Ile Ile Lys Asn Gly Asp Phe Asn Asn
                955                 960                 965

GGC TTA TTA TGC TGG AAC GTG AAA GGG CAT GTA GAG GTA GAA GAA CAA       3218
Gly Leu Leu Cys Trp Asn Val Lys Gly His Val Glu Val Glu Glu Gln
970                 975                 980                 985

AAC AAT CAC CGT TCA GTC CTG GTT ATC CCA GAA TGG GAG GCA GAA GTG       3266
Asn Asn His Arg Ser Val Leu Val Ile Pro Glu Trp Glu Ala Glu Val
                990                 995                 1000

TCA CAA GAG GTT CGT GTC TGT CCA GGT CGT GGC TAT ATC CTT CGT GTT       3314
Ser Gln Glu Val Arg Val Cys Pro Gly Arg Gly Tyr Ile Leu Arg Val
                1005                1010                1015

ACA GCG TAC AAA GAG GGA TAT GGA GAA GGT TGC GTA ACG ATC CAT GAG       3362
Thr Ala Tyr Lys Glu Gly Tyr Gly Glu Gly Cys Val Thr Ile His Glu
                1020                1025                1030

ATC GAG AAC AAT ACA GAC GAA CTG AAA TTC AAC AAC TGT GTA GAA GAG       3410
Ile Glu Asn Asn Thr Asp Glu Leu Lys Phe Asn Asn Cys Val Glu Glu
                1035                1040                1045

GAA GTA TAT CCA AAC AAC ACG GTA ACG TGT ATT AAT TAT ACT GCG ACT       3458
Glu Val Tyr Pro Asn Asn Thr Val Thr Cys Ile Asn Tyr Thr Ala Thr
1050                1055                1060                1065

CAA GAA GAA TAT GAG GGT ACG TAC ACT TCT CGT AAT CGA GGA TAT GAC       3506
Gln Glu Glu Tyr Glu Gly Thr Tyr Thr Ser Arg Asn Arg Gly Tyr Asp
                1070                1075                1080

GAA GCC TAT GGT AAT AAC CCT TCC GTA CCA GCT GAT TAT GCG TCA GTC       3554
Glu Ala Tyr Gly Asn Asn Pro Ser Val Pro Ala Asp Tyr Ala Ser Val
                1085                1090                1095

TAT GAA GAA AAA TCG TAT ACA GAT AGA CGA AGA GAG AAT CCT TGT GAA       3602
Tyr Glu Glu Lys Ser Tyr Thr Asp Arg Arg Arg Glu Asn Pro Cys Glu
                1100                1105                1110

TCT AAC AGA GGA TAT GGA GAT TAC ACA CCA CTA CCA GCT GGT TAT GTA       3650
Ser Asn Arg Gly Tyr Gly Asp Tyr Thr Pro Leu Pro Ala Gly Tyr Val
                1115                1120                1125

ACA AAG GAA TTA GAG TAC TTC CCA GAG ACC GAT AAG GTA TGG ATT GAG       3698
Thr Lys Glu Leu Glu Tyr Phe Pro Glu Thr Asp Lys Val Trp Ile Glu
1130                1135                1140                1145

ATT GGA GAA ACA GAA GGA ACA TTC ATC GTG GAC AGC GTG GAA TTA CTC       3746
Ile Gly Glu Thr Glu Gly Thr Phe Ile Val Asp Ser Val Glu Leu Leu
                1150                1155                1160

CTT ATG GAG GAA TAGGACCATC CGAGTATAGC AGTTTAATAA ATATTAATTA           3798
Leu Met Glu Glu
                1165

AAATAGTAGT CTAACTTCCG TTCCAATTAA ATAAGTAAAT TACAGTTGTA AAAAAAACG      3858

AACATTACTC TTCAAAGAGC GATGTCCGTT TTTTATATGG TGTGT                     3903
```

( 2 ) INFORMATION FOR SEQ ID NO:4:

( i ) SEQUENCE CHARACTERISTICS:
        ( A ) LENGTH: 3923 base pairs
        ( B ) TYPE: nucleic acid
        ( C ) STRANDEDNESS: double
        ( D ) TOPOLOGY: linear 5,866,784

41                                                                                   42
-continued (ii) MOLECULE TYPE: DNA (genomic)

(ix) FEATURE:
    (A) NAME/KEY: CDS
    (B) LOCATION: 234..3803

(ix) FEATURE:
    (A) NAME/KEY: 5'UTR
    (B) LOCATION: 1..233

(ix) FEATURE:
    (A) NAME/KEY: 3'UTR
    (B) LOCATION: 3804..3923

(xi) SEQUENCE DESCRIPTION: SEQ ID NO:4:

```
AATAGAATCT CAAATCTCGA TGACTGCTTA GTCTTTTTAA TACTGTCTAC TTGACAGGGG         60

TAGGAACATA ATCGGTCAAT TTTAAATATG GGGCATATAT TGATATTTTA TAAAATTTGT        120

TACGTTTTTT GTATTTTTTC ATAAGATGTG TCATATGTAT TAAATCGTGG TAATGAAAAA        180

CAGTATCAAA CTATCAGAAC TTTGGTAGTT TAATAAAAAA ACGGAGGTAT TTT ATG          236
                                                              Met
                                                               1

GAG GAA AAT AAT CAA AAT CAA TGC ATA CCT TAC AAT TGT TTA AGT AAT          284
Glu Glu Asn Asn Gln Asn Gln Cys Ile Pro Tyr Asn Cys Leu Ser Asn
             5                  10                 15

CCT GAA GAA GTA CTT TTG GAT GGA GAA CGG ATA TCA ACT GGT AAT TCA          332
Pro Glu Glu Val Leu Leu Asp Gly Glu Arg Ile Ser Thr Gly Asn Ser
         20                 25                 30

TCA ATT GAT ATT TCT CTG TCA CTT GTT CAG TTT CTG GTA TCT AAC TTT          380
Ser Ile Asp Ile Ser Leu Ser Leu Val Gln Phe Leu Val Ser Asn Phe
     35                 40                 45

GTA CCA GGG GGA GGA TTT TTA GTT GGA TTA ATA GAT TTT GTA TGG GGA          428
Val Pro Gly Gly Gly Phe Leu Val Gly Leu Ile Asp Phe Val Trp Gly
 50                 55                 60                 65

ATA GTT GGC CCT TCT CAA TGG GAT GCA TTT CTA GTA CAA ATT GAA CAA          476
Ile Val Gly Pro Ser Gln Trp Asp Ala Phe Leu Val Gln Ile Glu Gln
                 70                 75                 80

TTA ATT AAT GAA AGA ATA GCT GAA TTT GCT AGG AAT GCT GCT ATT GCT          524
Leu Ile Asn Glu Arg Ile Ala Glu Phe Ala Arg Asn Ala Ala Ile Ala
             85                 90                 95

AAT TTA GAA GGA TTA GGA AAC AAT TTC AAT ATA TAT GTG GAA GCA TTT          572
Asn Leu Glu Gly Leu Gly Asn Asn Phe Asn Ile Tyr Val Glu Ala Phe
        100                105                110

AAA GAA TGG GAA GAA GAT CCT AAT AAT CCA GAA ACC AGG ACC AGA GTA          620
Lys Glu Trp Glu Glu Asp Pro Asn Asn Pro Glu Thr Arg Thr Arg Val
    115                120                125

ATT GAT CGC TTT CGT ATA CTT GAT GGG CTA CTT GAA AGG GAC ATT CCT          668
Ile Asp Arg Phe Arg Ile Leu Asp Gly Leu Leu Glu Arg Asp Ile Pro
130                135                140                145

TCG TTT CGA ATT TCT GGA TTT GAA GTA CCC CTT TTA TCC GTT TAT GCT          716
Ser Phe Arg Ile Ser Gly Phe Glu Val Pro Leu Leu Ser Val Tyr Ala
                150                155                160

CAA GCG GCC AAT CTG CAT CTA GCT ATA TTA AGA GAT TCT GTA ATT TTT          764
Gln Ala Ala Asn Leu His Leu Ala Ile Leu Arg Asp Ser Val Ile Phe
            165                170                175

GGA GAA AGA TGG GGA TTG ACA ACG ATA AAT GTC AAT GAA AAC TAT AAT          812
Gly Glu Arg Trp Gly Leu Thr Thr Ile Asn Val Asn Glu Asn Tyr Asn
        180                185                190

AGA CTA ATT AGG CAT ATT GAT GAA TAT GCT GAT CAC TGT GCA AAT ACG          860
Arg Leu Ile Arg His Ile Asp Glu Tyr Ala Asp His Cys Ala Asn Thr
    195                200                205

TAT AAT CGG GGA TTA AAT AAT TTA CCG AAA TCT ACG TAT CAA GAT TGG          908
Tyr Asn Arg Gly Leu Asn Asn Leu Pro Lys Ser Thr Tyr Gln Asp Trp
```

```
                210                    215                     220                       225
ATA ACA TAT AAT CGA TTA CGG AGA GAC TTA ACA TTG ACT GTA TTA GAT           956
Ile Thr Tyr Asn Arg Leu Arg Arg Asp Leu Thr Leu Thr Val Leu Asp
                230                     235                       240

ATC GCC GCT TTC TTT CCA AAC TAT GAC AAT AGG AGA TAT CCA ATT CAG           1004
Ile Ala Ala Phe Phe Pro Asn Tyr Asp Asn Arg Arg Tyr Pro Ile Gln
            245                     250                       255

CCA GTT GGT CAA CTA ACA AGG GAA GTT TAT ACG GAC CCA TTA ATT AAT           1052
Pro Val Gly Gln Leu Thr Arg Glu Val Tyr Thr Asp Pro Leu Ile Asn
                260                     265                       270

TTT AAT CCA CAG TTA CAG TCT GTA GCT CAA TTA CCT ACT TTT AAC GTT           1100
Phe Asn Pro Gln Leu Gln Ser Val Ala Gln Leu Pro Thr Phe Asn Val
            275                     280                       285

ATG GAG AGC AGC GCA ATT AGA AAT CCT CAT TTA TTT GAT ATA TTG AAT           1148
Met Glu Ser Ser Ala Ile Arg Asn Pro His Leu Phe Asp Ile Leu Asn
290                     295                     300                       305

AAT CTT ACA ATC TTT ACG GAT TGG TTT AGT GTT GGA CGC AAT TTT TAT           1196
Asn Leu Thr Ile Phe Thr Asp Trp Phe Ser Val Gly Arg Asn Phe Tyr
                310                     315                       320

TGG GGA GGA CAT CGA GTA ATA TCT AGC CTT ATA GGA GGT GGT AAC ATA           1244
Trp Gly Gly His Arg Val Ile Ser Ser Leu Ile Gly Gly Gly Asn Ile
            325                     330                       335

ACA TCT CCT ATA TAT GGA AGA GAG GCG AAC CAG GAG CCT CCA AGA TCC           1292
Thr Ser Pro Ile Tyr Gly Arg Glu Ala Asn Gln Glu Pro Pro Arg Ser
            340                     345                       350

TTT ACT TTT AAT GGA CCG GTA TTT AGG ACT TTA TCA AAT CCT ACT TTA           1340
Phe Thr Phe Asn Gly Pro Val Phe Arg Thr Leu Ser Asn Pro Thr Leu
        355                     360                       365

CGA TTA TTA CAG CAA CCT TGG CCA GCG CCA CCA TTT AAT TTA CGT GGT           1388
Arg Leu Leu Gln Gln Pro Trp Pro Ala Pro Pro Phe Asn Leu Arg Gly
370                     375                     380                       385

GTT GAA GGA GTA GAA TTT TCT ACA CCT ACA AAT AGC TTT ACG TAT CGA           1436
Val Glu Gly Val Glu Phe Ser Thr Pro Thr Asn Ser Phe Thr Tyr Arg
                390                     395                       400

GGA AGA GGT ACG GTT GAT TCT TTA ACT GAA TTA CCG CCT GAG GAT AAT           1484
Gly Arg Gly Thr Val Asp Ser Leu Thr Glu Leu Pro Pro Glu Asp Asn
            405                     410                       415

AGT GTG CCA CCT CGC GAA GGA TAT AGT CAT CGT TTA TGT CAT GCA ACT           1532
Ser Val Pro Pro Arg Glu Gly Tyr Ser His Arg Leu Cys His Ala Thr
            420                     425                       430

TTT GTT CAA AGA TCT GGA ACA CCT TTT TTA ACA ACT GGT GTA GTA TTT           1580
Phe Val Gln Arg Ser Gly Thr Pro Phe Leu Thr Thr Gly Val Val Phe
        435                     440                       445

TCT TGG ACG CAT CGT AGT GCA ACT CTT ACA AAT ACA ATT GAT CCA GAG           1628
Ser Trp Thr His Arg Ser Ala Thr Leu Thr Asn Thr Ile Asp Pro Glu
450                     455                     460                       465

AGA ATT AAT CAA ATA CCT TTA GTG AAA GGA TTT AGA GTT TGG GGG GGC           1676
Arg Ile Asn Gln Ile Pro Leu Val Lys Gly Phe Arg Val Trp Gly Gly
                470                     475                       480

ACC TCT GTC ATT ACA GGA CCA GGA TTT ACA GGA GGG GAT ATC CTT CGA           1724
Thr Ser Val Ile Thr Gly Pro Gly Phe Thr Gly Gly Asp Ile Leu Arg
            485                     490                       495

AGA AAT ACC TTT GGT GAT TTT GTA TCT CTA CAA GTC AAT ATT AAT TCA           1772
Arg Asn Thr Phe Gly Asp Phe Val Ser Leu Gln Val Asn Ile Asn Ser
            500                     505                       510

CCA ATT ACC CAA AGA TAC CGT TTA AGA TTT CGT TAC GCT TCC AGT AGG           1820
Pro Ile Thr Gln Arg Tyr Arg Leu Arg Phe Arg Tyr Ala Ser Ser Arg
        515                     520                       525

GAT GCA CGA GTT ATA GTA TTA ACA GGA GCG GCA TCC ACA GGA GTG GGA           1868
Asp Ala Arg Val Ile Val Leu Thr Gly Ala Ala Ser Thr Gly Val Gly
```

-continued

| | | | | | | | | | | | | | | | | |
|---|---|---|---|---|---|---|---|---|---|---|---|---|---|---|---|---|
| 530 | | | | | 535 | | | | | 540 | | | | | 545 | |
| GGC | CAA | GTT | AGT | GTA | AAT | ATG | CCT | CTT | CAG | AAA | ACT | ATG | GAA | ATA | GGG | 1916 |
| Gly | Gln | Val | Ser | Val 550 | Asn | Met | Pro | Leu | Gln 555 | Lys | Thr | Met | Glu | Ile 560 | Gly | |
| GAG | AAC | TTA | ACA | TCT | AGA | ACA | TTT | AGA | TAT | ACC | GAT | TTT | AGT | AAT | CCT | 1964 |
| Glu | Asn | Leu | Thr 565 | Ser | Arg | Thr | Phe | Arg 570 | Tyr | Thr | Asp | Phe | Ser 575 | Asn | Pro | |
| TTT | TCA | TTT | AGA | GCT | AAT | CCA | GAT | ATA | ATT | GGG | ATA | AGT | GAA | CAA | CCT | 2012 |
| Phe | Ser | Phe 580 | Arg | Ala | Asn | Pro | Asp 585 | Ile | Ile | Gly | Ile | Ser 590 | Glu | Gln | Pro | |
| CTA | TTT | GGT | GCA | GGT | TCT | ATT | AGT | AGC | GGT | GAA | CTT | TAT | ATA | GAT | AAA | 2060 |
| Leu | Phe 595 | Gly | Ala | Gly | Ser | Ile 600 | Ser | Ser | Gly | Glu | Leu 605 | Tyr | Ile | Asp | Lys | |
| ATT | GAA | ATT | ATT | CTA | GCA | GAT | GCA | ACA | TTT | GAA | GCA | GAA | TCT | GAT | TTA | 2108 |
| Ile 610 | Glu | Ile | Ile | Leu | Ala 615 | Asp | Ala | Thr | Phe | Glu 620 | Ala | Glu | Ser | Asp | Leu 625 | |
| GAA | AGA | GCA | CAA | AAG | GCG | GTG | AAT | GCC | CTG | TTT | ACT | TCT | TCC | AAT | CAA | 2156 |
| Glu | Arg | Ala | Gln | Lys 630 | Ala | Val | Asn | Ala | Leu 635 | Phe | Thr | Ser | Ser | Asn 640 | Gln | |
| ATC | GGG | TTA | AAA | ACC | GAT | GTG | ACG | GAT | TAT | CAT | ATT | GAT | CAA | GTA | TCC | 2204 |
| Ile | Gly | Leu | Lys 645 | Thr | Asp | Val | Thr | Asp 650 | Tyr | His | Ile | Asp | Gln 655 | Val | Ser | |
| AAT | TTA | GTG | GAT | TGT | TTA | TCA | GAT | GAA | TTT | TGT | CTG | GAT | GAA | AAG | CGA | 2252 |
| Asn | Leu | Val 660 | Asp | Cys | Leu | Ser | Asp 665 | Glu | Phe | Cys | Leu | Asp 670 | Glu | Lys | Arg | |
| GAA | TTG | TCC | GAG | AAA | GTC | AAA | CAT | GCG | AAG | CGA | CTC | AGT | GAT | GAG | CGG | 2300 |
| Glu | Leu | Ser 675 | Glu | Lys | Val | Lys 680 | His | Ala | Lys | Arg | Leu 685 | Ser | Asp | Glu | Arg | |
| AAT | TTA | CTT | CAA | GAT | CCA | AAC | TTC | AGA | GGG | ATC | AAT | AGA | CAA | CCA | GAC | 2348 |
| Asn | Leu | Leu | Gln | Asp 695 | Pro | Asn | Phe | Arg | Gly 700 | Ile | Asn | Arg | Gln | Pro 705 | Asp | |
| | | | | | | | | | | | | | | | | |
| | | | 690 | | | | | | | | | | | | | |
| CGT | GGC | TGG | AGA | GGA | AGT | ACA | GAT | ATT | ACC | ATC | CAA | GGA | GGA | GAT | GAC | 2396 |
| Arg | Gly | Trp | Arg | Gly 710 | Ser | Thr | Asp | Ile | Thr 715 | Ile | Gln | Gly | Gly | Asp 720 | Asp | |
| GTA | TTC | AAA | GAG | AAT | TAC | GTC | ACA | CTA | CCG | GGT | ACC | GTT | GAT | GAG | TGC | 2444 |
| Val | Phe | Lys | Glu 725 | Asn | Tyr | Val | Thr | Leu 730 | Pro | Gly | Thr | Val | Asp 735 | Glu | Cys | |
| TAT | CCA | ACG | TAT | TTA | TAT | CAG | AAA | ATA | GAT | GAG | TCG | AAA | TTA | AAA | GCT | 2492 |
| Tyr | Pro | Thr 740 | Tyr | Leu | Tyr | Gln | Lys 745 | Ile | Asp | Glu | Ser | Lys 750 | Leu | Lys | Ala | |
| TAT | ACC | CGT | TAT | GAA | TTA | AGA | GGG | TAT | ATC | GAA | GAT | AGT | CAA | GAC | TTA | 2540 |
| Tyr | Thr 755 | Arg | Tyr | Glu | Leu | Arg 760 | Gly | Tyr | Ile | Glu | Asp 765 | Ser | Gln | Asp | Leu | |
| GAA | ATC | TAT | TTG | ATC | CGT | TAC | AAT | GCA | AAA | CAC | GAA | ATA | GTA | AAT | GTG | 2588 |
| Glu | Ile | Tyr | Leu | Ile | Arg | Tyr | Asn | Ala | Lys | His | Glu | Ile | Val | Asn | Val | |
| 770 | | | | | 775 | | | | | 780 | | | | | 785 | |
| CCA | GGC | ACG | GGT | TCC | TTA | TGG | CCG | CTT | TCA | GCC | CAA | AGT | CCA | ATC | GGA | 2636 |
| Pro | Gly | Thr | Gly | Ser 790 | Leu | Trp | Pro | Leu | Ser 795 | Ala | Gln | Ser | Pro | Ile 800 | Gly | |
| AAG | TGT | GGA | GAA | CCG | AAT | CGA | TGC | GCG | CCA | CAC | CTT | GAA | TGG | AAT | CCT | 2684 |
| Lys | Cys | Gly | Glu 805 | Pro | Asn | Arg | Cys | Ala 810 | Pro | His | Leu | Glu | Trp 815 | Asn | Pro | |
| GAT | CTA | GAT | TGT | TCC | TGC | AGA | GAC | GGG | GAA | AAA | TGT | GCA | CAT | CAT | TCC | 2732 |
| Asp | Leu | Asp 820 | Cys | Ser | Cys | Arg | Asp 825 | Gly | Glu | Lys | Cys | Ala 830 | His | His | Ser | |
| CAT | CAT | TTC | ACC | TTG | GAT | ATT | GAT | GTT | GGA | TGT | ACA | GAC | TTA | AAT | GAG | 2780 |
| His | His | Phe 835 | Thr | Leu | Asp | Ile | Asp 840 | Val | Gly | Cys | Thr | Asp 845 | Leu | Asn | Glu | |
| GAC | TTA | GGT | GTA | TGG | GTG | ATA | TTC | AAG | ATT | AAG | ACG | CAA | GAT | GGC | CAT | 2828 |
| Asp | Leu | Gly | Val | Trp | Val | Ile | Phe | Lys | Ile | Lys | Thr | Gln | Asp | Gly | His | |

-continued

```
         850                          855                          860                          865
GCA AGA CTA GGG AAT CTA GAG TTT CTC GAA GAG AAA CCA TTA TTA GGG        2876
Ala Arg Leu Gly Asn Leu Glu Phe Leu Glu Glu Lys Pro Leu Leu Gly
                870                          875                          880

GAA GCA CTA GCT CGT GTG AAA AGA GCG GAG AAG AAG TGG AGA GAC AAA        2924
Glu Ala Leu Ala Arg Val Lys Arg Ala Glu Lys Lys Trp Arg Asp Lys
                885                          890                          895

CGA GAG AAA CTG CAG TTG GAA ACA AAT ATT GTT TAT AAA GAG GCA AAA        2972
Arg Glu Lys Leu Gln Leu Glu Thr Asn Ile Val Tyr Lys Glu Ala Lys
                900                          905                          910

GAA TCT GTA GAT GCT TTA TTT GTA AAC TCT CAA TAT GAT AGA TTA CAA        3020
Glu Ser Val Asp Ala Leu Phe Val Asn Ser Gln Tyr Asp Arg Leu Gln
        915                          920                          925

GTG GAT ACG AAC ATC GCG ATG ATT CAT GCG GCA GAT AAA CGC GTT CAT        3068
Val Asp Thr Asn Ile Ala Met Ile His Ala Ala Asp Lys Arg Val His
930                          935                          940                          945

AGA ATC CGG GAA GCG TAT CTG CCA GAG TTG TCT GTG ATT CCA GGT GTC        3116
Arg Ile Arg Glu Ala Tyr Leu Pro Glu Leu Ser Val Ile Pro Gly Val
                950                          955                          960

AAT GCG GCC ATT TTC GAA GAA TTA GAG GGA CGT ATT TTT ACA GCG TAT        3164
Asn Ala Ala Ile Phe Glu Glu Leu Glu Gly Arg Ile Phe Thr Ala Tyr
                965                          970                          975

TCC TTA TAT GAT GCG AGA AAT GTC ATT AAA AAT GGC GAT TTC AAT AAT        3212
Ser Leu Tyr Asp Ala Arg Asn Val Ile Lys Asn Gly Asp Phe Asn Asn
                980                          985                          990

GGC TTA TTA TGC TGG AAC GTG AAA GGT CAT GTA GAT GTA GAA GAG CAA        3260
Gly Leu Leu Cys Trp Asn Val Lys Gly His Val Asp Val Glu Glu Gln
        995                          1000                         1005

AAC AAC CAC CGT TCG GTC CTT GTT ATC CCA GAA TGG GAG GCA GAA GTG        3308
Asn Asn His Arg Ser Val Leu Val Ile Pro Glu Trp Glu Ala Glu Val
1010                         1015                         1020                         1025

TCA CAA GAG GTT CGT GTC TGT CCA GGT CGT GGC TAT ATC CTT CGT GTC        3356
Ser Gln Glu Val Arg Val Cys Pro Gly Arg Gly Tyr Ile Leu Arg Val
                1030                         1035                         1040

ACA GCA TAT AAA GAG GGA TAT GGA GAG GGC TGC GTA ACG ATC CAT GAG        3404
Thr Ala Tyr Lys Glu Gly Tyr Gly Glu Gly Cys Val Thr Ile His Glu
                1045                         1050                         1055

ATC GAA GAC AAT ACA GAC GAA CTG AAA TTC AGC AAC TGT GTA GAA GAG        3452
Ile Glu Asp Asn Thr Asp Glu Leu Lys Phe Ser Asn Cys Val Glu Glu
                1060                         1065                         1070

GAA GTA TAT CCA AAC AAC ACA GTA ACG TGT AAT AAT TAT ACT GGG ACT        3500
Glu Val Tyr Pro Asn Asn Thr Val Thr Cys Asn Asn Tyr Thr Gly Thr
        1075                         1080                         1085

CAA GAA GAA TAT GAG GGT ACG TAC ACT TCT CGT AAT CAA GGA TAT GAC        3548
Gln Glu Glu Tyr Glu Gly Thr Tyr Thr Ser Arg Asn Gln Gly Tyr Asp
1090                         1095                         1100                         1105

GAA GCC TAT GGT AAT AAC CCT TCC GTA CCA GCT GAT TAC GCT TCA GTC        3596
Glu Ala Tyr Gly Asn Asn Pro Ser Val Pro Ala Asp Tyr Ala Ser Val
                1110                         1115                         1120

TAT GAA GAA AAA TCG TAT ACA GAT GGA CGA AGA GAG AAT CCT TGT GAA        3644
Tyr Glu Glu Lys Ser Tyr Thr Asp Gly Arg Arg Glu Asn Pro Cys Glu
                1125                         1130                         1135

TCT AAC AGA GGC TAT GGG GAT TAC ACA CCA CTA CCG GCT GGT TAT GTA        3692
Ser Asn Arg Gly Tyr Gly Asp Tyr Thr Pro Leu Pro Ala Gly Tyr Val
                1140                         1145                         1150

ACA AAG GAT TTA GAG TAC TTC CCA GAG ACC GAT AAG GTA TGG ATT GAG        3740
Thr Lys Asp Leu Glu Tyr Phe Pro Glu Thr Asp Lys Val Trp Ile Glu
        1155                         1160                         1165

ATC GGA GAA ACA GAA GGA ACA TTC ATC GTG GAT AGC GTG GAA TTA CTC        3788
Ile Gly Glu Thr Glu Gly Thr Phe Ile Val Asp Ser Val Glu Leu Leu
```

-continued

```
                1170                    1175                    1180                    1185
CTT ATG GAG GAA TAAGATACGT TATAAAATGT AACGTATGCA AATAAAGAAT                                    3840
Leu Met Glu Glu
                119

GATTACTGAC CTATATTAAC AGATAAATAA GAAAATTTTT ATACGAATAA AAAACGGACA                              3900

TCACTCTTAA GAGAATGATG TCC                                                                     3923
```